(12) United States Patent
Choubey et al.

(10) Patent No.: US 8,268,340 B2
(45) Date of Patent: Sep. 18, 2012

(54) IMPLANTABLE MATERIALS HAVING ENGINEERED SURFACES AND METHOD OF MAKING SAME

(75) Inventors: Animesh Choubey, Fremont, CA (US); Julio C. Palmaz, Napa, CA (US)

(73) Assignee: Advanced Bio Prosthetic Surfaces, Ltd., Dallas, TX (US)

( * ) Notice: Subject to any disclaimer, the term of this patent is extended or adjusted under 35 U.S.C. 154(b) by 145 days.

(21) Appl. No.: 12/428,981

(22) Filed: Apr. 23, 2009

(65) Prior Publication Data

US 2009/0304772 A1 Dec. 10, 2009

Related U.S. Application Data

(63) Continuation-in-part of application No. 11/091,669, filed as application No. PCT/US03/30383 on Sep. 26, 2003, now Pat. No. 8,147,859.

(60) Provisional application No. 60/414,031, filed on Sep. 26, 2002.

(51) Int. Cl.
*A61F 2/02* (2006.01)
*A61F 2/06* (2006.01)
(52) U.S. Cl. ........................ 424/423; 623/1.15
(58) Field of Classification Search ............... 424/423; 623/1.15
See application file for complete search history.

(56) References Cited

U.S. PATENT DOCUMENTS

| | | | |
|---|---|---|---|
| 4,657,544 A | 4/1987 | Pinchuk | 623/1 |
| 5,133,845 A | 7/1992 | Vallana et al. | 204/192.15 |
| 5,207,709 A | 5/1993 | Picha | 623/11 |
| 5,278,063 A | 1/1994 | Hubbell et al. | 435/240 |
| 5,370,684 A | 12/1994 | Vallana et al. | 623/1 |
| 5,387,247 A | 2/1995 | Vallana et al. | 623/2.42 |
| 5,423,885 A | 6/1995 | Williams | 623/1 |
| 5,510,628 A | 4/1996 | Georger, Jr. et al. | 257/32 |
| 5,607,463 A | 3/1997 | Schwartz et al. | 623/1.44 |
| 5,649,951 A | 7/1997 | Davidson | 606/198 |
| 5,690,670 A | 11/1997 | Davidson | 606/198 |
| 5,725,573 A | 3/1998 | Dearnaley et al. | 427/2.25 |
| 5,733,303 A | 3/1998 | Israel et al. | 606/198 |
| 5,735,896 A | 4/1998 | Amon et al. | 623/11 |
| 5,782,908 A | 7/1998 | Cahalan et al. | 623/1.13 |
| 5,843,289 A | 12/1998 | Lee et al. | 204/192.3 |
| 5,891,507 A | 4/1999 | Jayaraman | 427/2.25 |
| 5,895,419 A | 4/1999 | Tweden et al. | 623/2 |
| 5,897,911 A | 4/1999 | Loeffler | 427/2.25 |
| 5,932,299 A | 8/1999 | Katoot | 427/508 |
| 5,955,588 A | 9/1999 | Tsang et al. | 536/21 |
| 6,001,622 A | 12/1999 | Dedhar et al. | 435/194 |

(Continued)

FOREIGN PATENT DOCUMENTS

EP 0603959 6/1994

(Continued)

OTHER PUBLICATIONS

International Search Report from PCT/US2010/032029, pp. 1-5 (Feb. 2011).

(Continued)

*Primary Examiner* — Rosanne Kosson
(74) *Attorney, Agent, or Firm* — J. Peter Paredes; Rosenbaum & Silvert, P.C.

(57) ABSTRACT

Implantable materials having engineered surfaces and method of making same comprising geometric features on at least one surface of the material having at least one of chemical, physiochemical and electrochemical activity different than regions of the at least one surface without the features.

11 Claims, 36 Drawing Sheets

U.S. PATENT DOCUMENTS

| | | | | |
|---|---|---|---|---|
| 6,027,526 | A | 2/2000 | Limon et al. | 623/1 |
| 6,077,413 | A | 6/2000 | Hafeli et al. | 205/170 |
| 6,086,773 | A | 7/2000 | Dufresne et al. | 216/8 |
| 6,103,320 | A | 8/2000 | Matsumoto et al. | 427/535 |
| 6,140,127 | A | 10/2000 | Sprague | 435/395 |
| 6,143,370 | A | 11/2000 | Panagiotou | 427/422 |
| RE36,991 | E | 12/2000 | Yamamoto et al. | 204/403 |
| 6,183,255 | B1 | 2/2001 | Oshida | 433/201.1 |
| 6,190,404 | B1 | 2/2001 | Palmaz et al. | 623/1.15 |
| 6,192,944 | B1 | 2/2001 | Greenhalgh | 139/425 |
| 6,207,536 | B1 | 3/2001 | Matsumoto et al. | 438/478 |
| 6,253,441 | B1 | 7/2001 | Wheat et al. | 29/527.2 |
| 6,258,121 | B1 | 7/2001 | Yang et al. | 623/1.46 |
| 6,274,014 | B1 | 8/2001 | Matsumoto et al. | 204/298 |
| 6,280,467 | B1 | 8/2001 | Leonhardt | 623/1.16 |
| 6,325,825 | B1 | 12/2001 | Kula et al. | 623/1.3 |
| 6,334,868 | B1 | 1/2002 | Ham | 623/1.13 |
| 6,379,383 | B1 | 4/2002 | Palmaz et al. | 623/1.49 |
| 6,432,128 | B1 | 8/2002 | Wallace et al. | 623/1.11 |
| 6,514,261 | B1 | 2/2003 | Randall et al. | 606/108 |
| 6,520,923 | B1 | 2/2003 | Jalisi | 600/585 |
| 6,527,919 | B1 | 3/2003 | Roth | 204/192 |
| 6,527,938 | B2 | 3/2003 | Bales et al. | 205/229 |
| 6,533,905 | B2 | 3/2003 | Johnson et al. | 204/192 |
| 6,537,310 | B1 | 3/2003 | Palmaz et al. | 623/1.13 |
| 6,652,579 | B1 | 11/2003 | Cox et al. | 623/1.34 |
| 6,689,473 | B2 | 2/2004 | Guire et al. | 428/412 |
| 6,849,085 | B2 | 2/2005 | Marton | 623/1.13 |
| 2001/0001834 | A1 | 5/2001 | Palmaz et al. | 623/1.12 |
| 2001/0039454 | A1 | 11/2001 | Ricci et al. | 623/23.5 |
| 2002/0016623 | A1 | 2/2002 | Kula et al. | 623/1.11 |
| 2002/0017503 | A1 | 2/2002 | Banas et al. | 219/69.11 |
| 2002/0156522 | A1 | 10/2002 | Ivancev et al. | 623/1.13 |
| 2003/0028246 | A1 | 2/2003 | Palmaz et al. | 623/1.49 |
| 2003/0130718 | A1 | 7/2003 | Palmas et al. | 623/1.12 |
| 2004/0014253 | A1 | 1/2004 | Gupta et al. | 438/48 |
| 2005/0055085 | A1 | 3/2005 | Rivron et al. | 623/1.39 |
| 2005/0102036 | A1 | 5/2005 | Bartee et al. | 623/23.76 |
| 2005/0119723 | A1 | 6/2005 | Peacock, III | 623/1.15 |
| 2006/0178751 | A1 | 8/2006 | Despres, III et al. | 623/23.5 |
| 2007/0225823 | A1 | 9/2007 | Hawkins et al. | 623/23.51 |
| 2008/0183276 | A1 | 7/2008 | Melder | 623/1.15 |

FOREIGN PATENT DOCUMENTS

| | | |
|---|---|---|
| EP | 0701803 | 3/1996 |
| EP | 0815806 | 1/1998 |
| EP | 0850604 | 1/1998 |
| WO | WO 95/12472 | 5/1995 |
| WO | WO 98/45506 | 10/1998 |
| WO | WO 99/23977 | 5/1999 |
| WO | WO 01/35865 | 5/2001 |
| WO | WO 01/68158 | 9/2001 |
| WO | WO 01/74274 | 10/2001 |
| WO | WO 01/76525 | 10/2001 |
| WO | WO 01/87371 | 11/2001 |

OTHER PUBLICATIONS

Written Opinion from PCT/US2010/032029, pp. 1-4 (Feb. 2011).

Chen C., et al., "Reports: Geometric Control of Cell Life and Death", *Science*, vol. 276, No. 5317, pp. 1425-1428 (May 1997), Abstract only.

Davies, PF., et al., "Endothelial Cell Adhesion in Real Time", *The Journal of Clinical Investigation*, vol. 91, pp. 2640-2652 (Jun. 1993).

Davies, PF., et al., "Quantitative Studies of Endothelial Cell Adhesion", *The Journal of Clinical Investigation*, vol. 93, pp. 2031-2038 (May 1994).

Den Braber, ET., et al., "Effects of Parallel Surface Microgrooves and Surface Energy on Cell Growth", *Journal of Biomedical Materials Research*, vol. 29, pp. 511-518 (1995).

European Supplementary Search Report, pp. 1-3 (Jan. 12, 2009).

Giancotti, FG., et al., "Review Integrin Signaling", *Science*, vol. 285, No. 5430, pp. 1028-1032 (Aug. 13, 1999), Abstract only.

Hehrlein, C., et al., "Therapy and Prevention: Influence of Surface Texture and Charge on the Biocompatibility of Endovascular Stents", University of Heidelberg, Germany; Department of Cardiology, Anatomy and Physical Chemistry, pp. 581-585 (1995).

Holleck, H., et al., "Multilayer PVD Coatings for Wear Protection", *Surface and Coatings Technology*, vol. 76-77, Part 1, pp. 328-336 (1997). Abstract Only.

Matsuda, T., "Control of Cell Adhesion, Migration, and Orientation on Photochemically Microporocessed Surfaces", *Journal of Biomedical Materials Research*, vol. 32, pp. 165-173 (1996).

Palmaz, JC., "New Advances in Endovascular Technology", *Texas Heart Institute Journal*, vol. 24, No. 3, pp. 156-159 (1997).

van der Giessen, WJ., et al., "Marked Inflammatory Sequel to Implantation of Biodegradable and Nonbiodegradable Polymers in Porcine Coronary Arteries", *Circulation*, vol. 94, No. 7, pp. 1690-1697 (1996).

Zarbakhsh, A., "Characterization of Photon-Controlled Titanium Ocide Surfaces", *ISIS Experimental Report*, Rutherford Appelton Laboratory, www.isis.rl.ac.uk/isis2001/reports/11144.pdf, (May 16, 2000).

FIG. 7
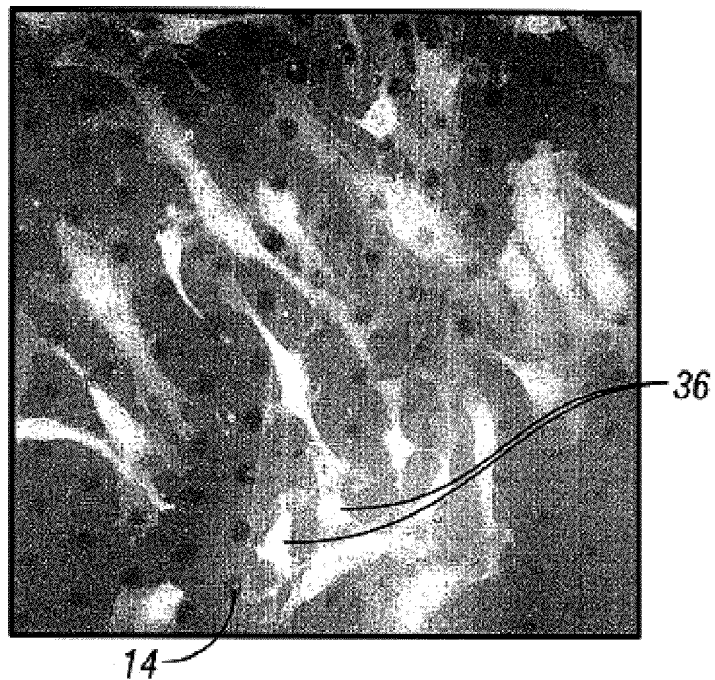
FIG. 8A

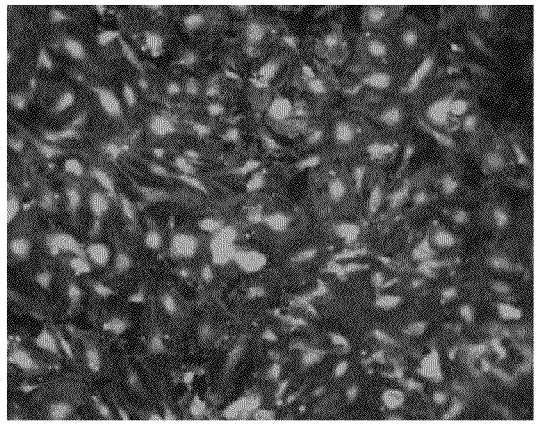 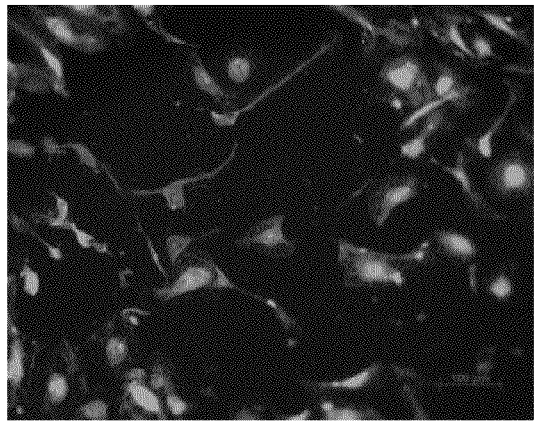
FIG. 17A         FIG. 17B
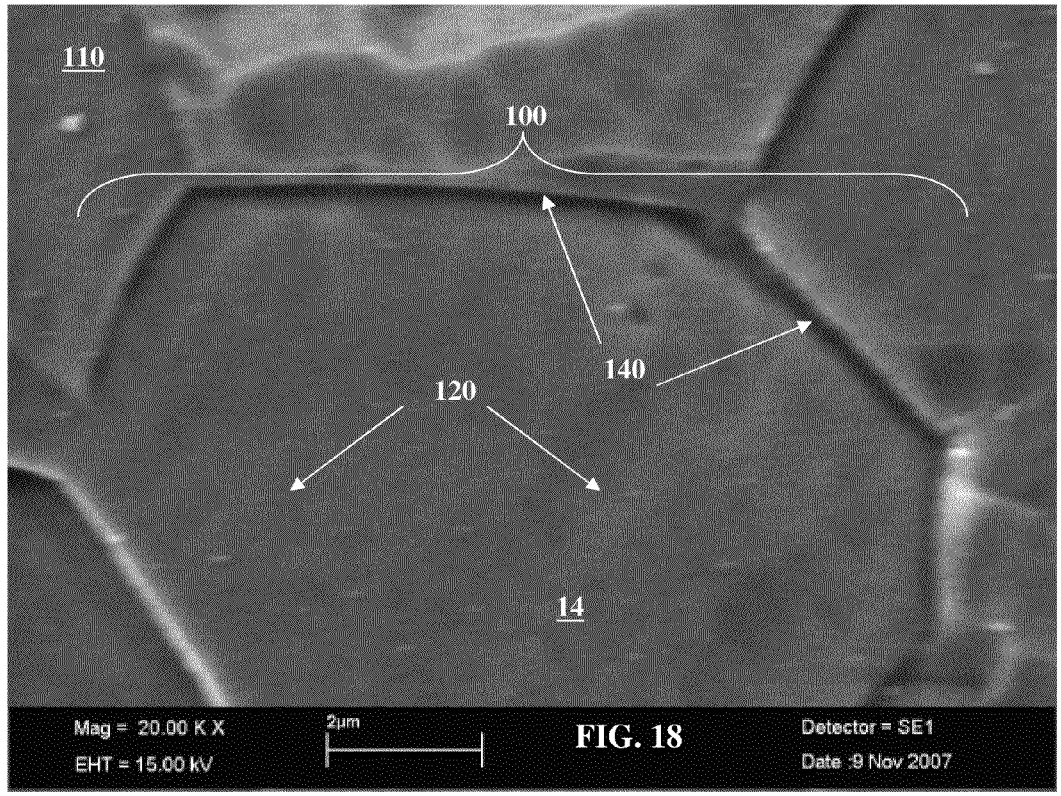
FIG. 18

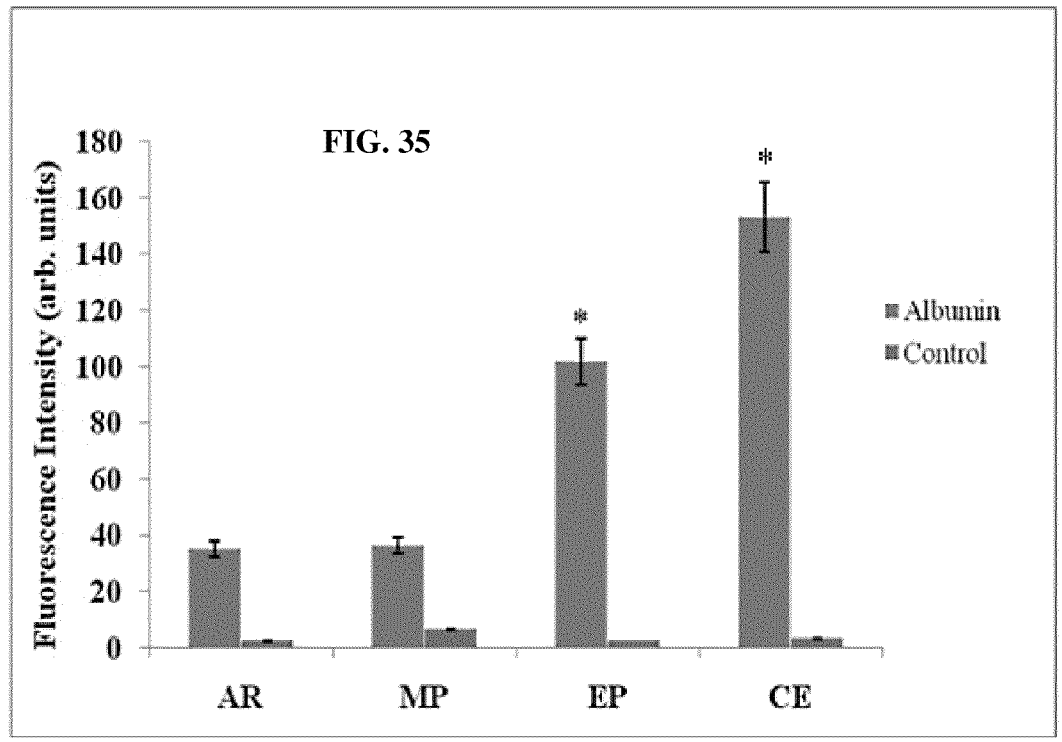
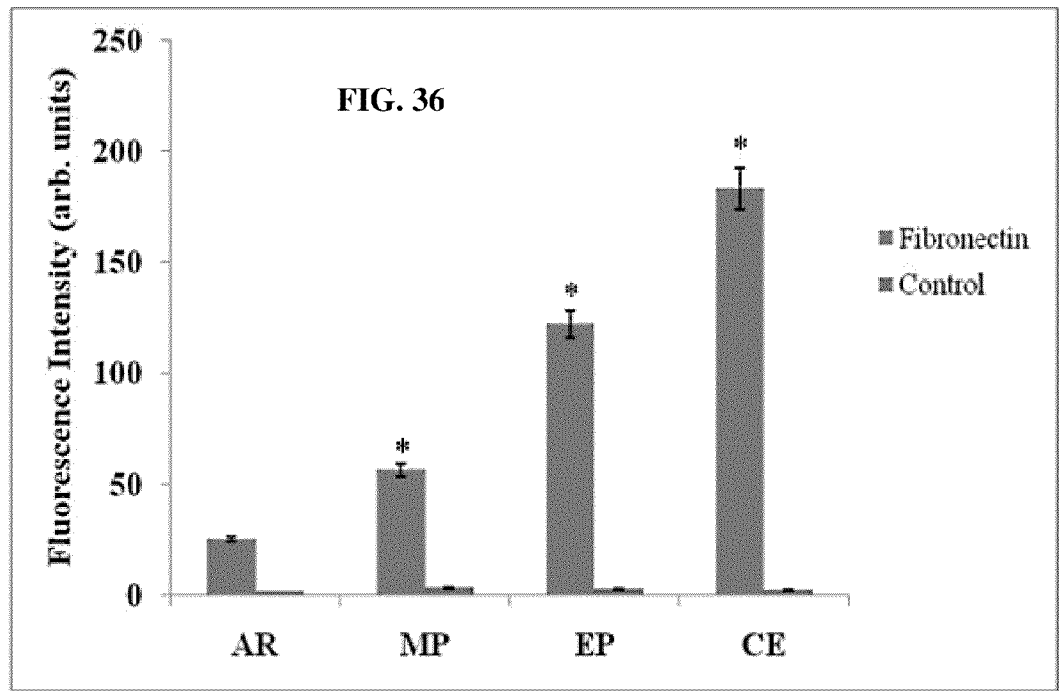

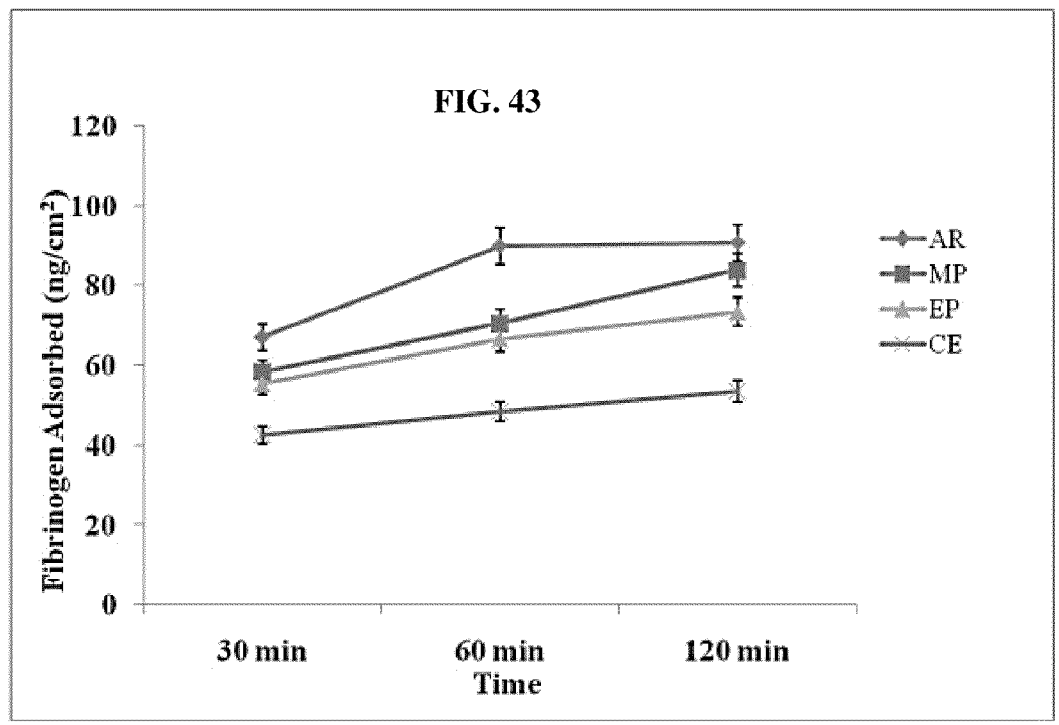
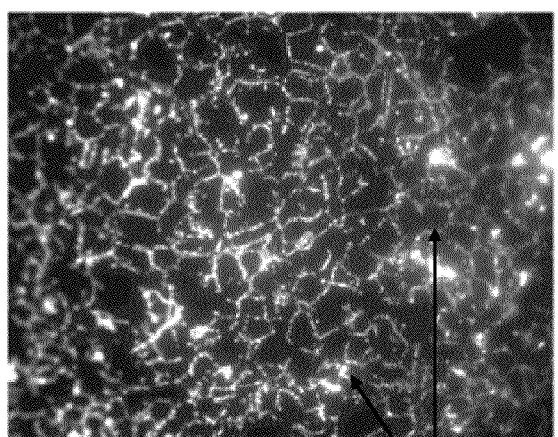
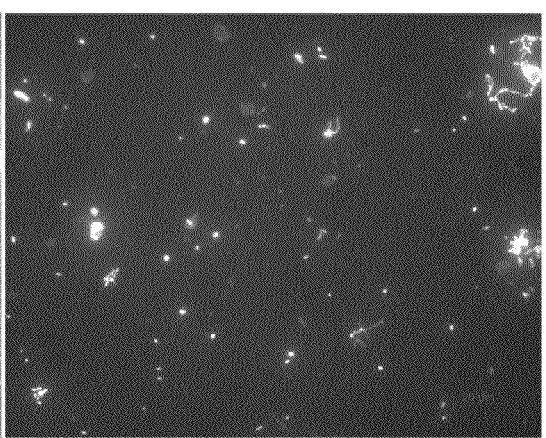
FIG. 44
FIG. 45
140

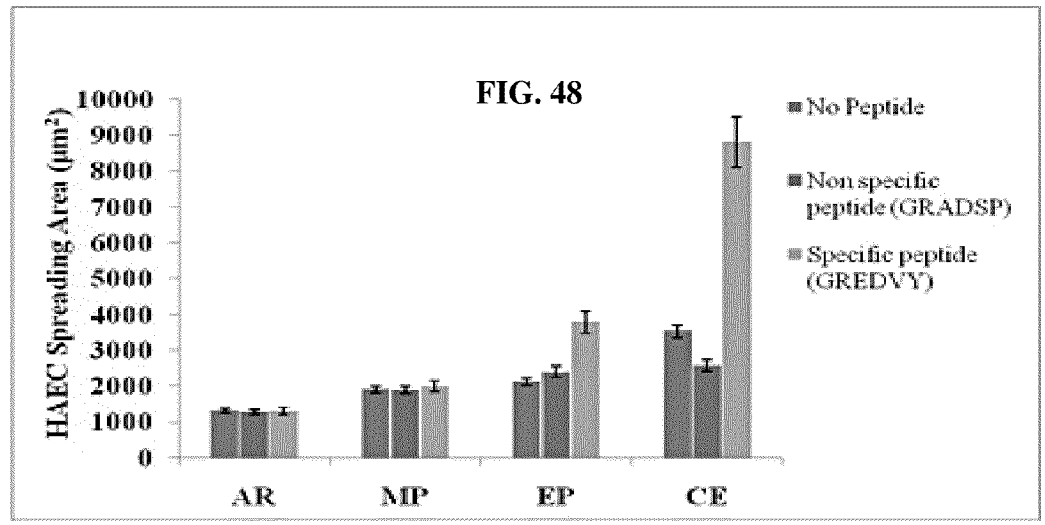
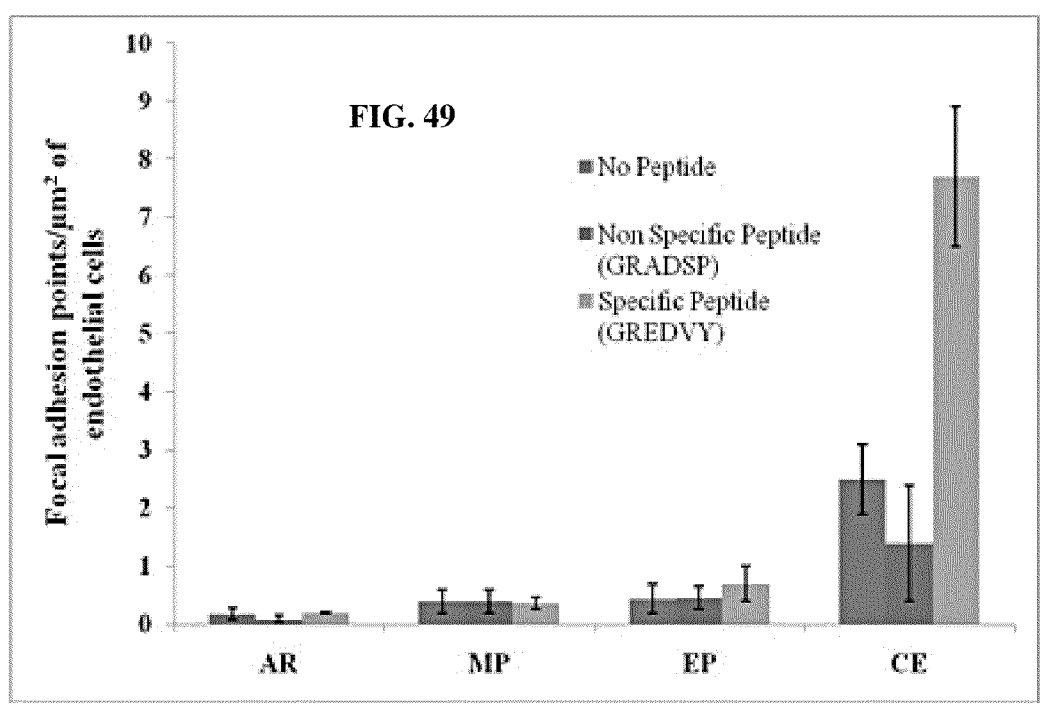

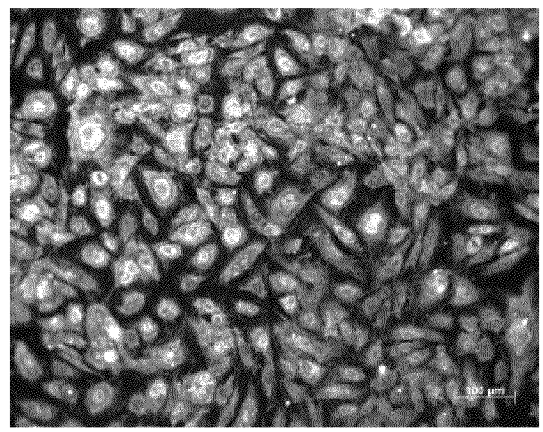
FIG. 50
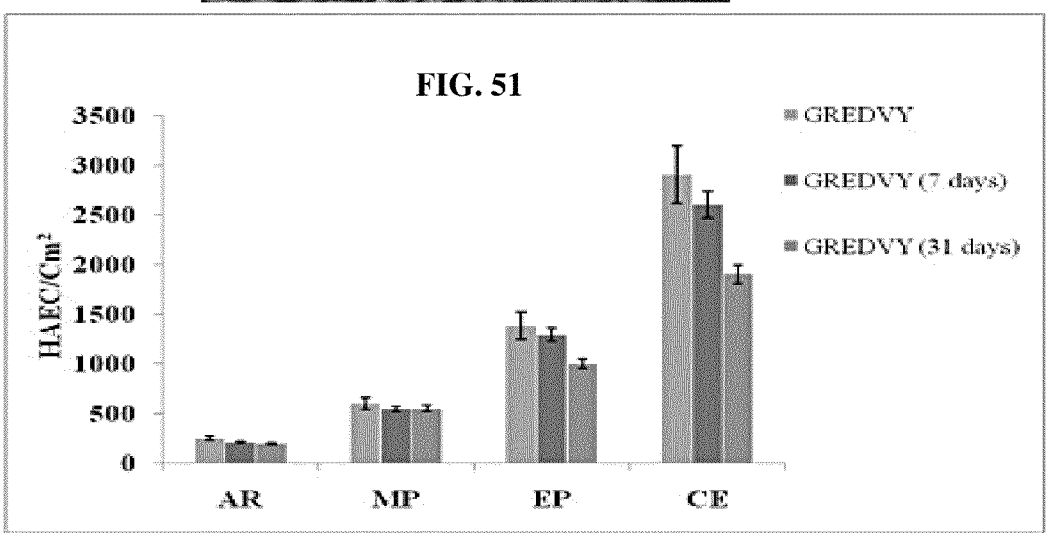
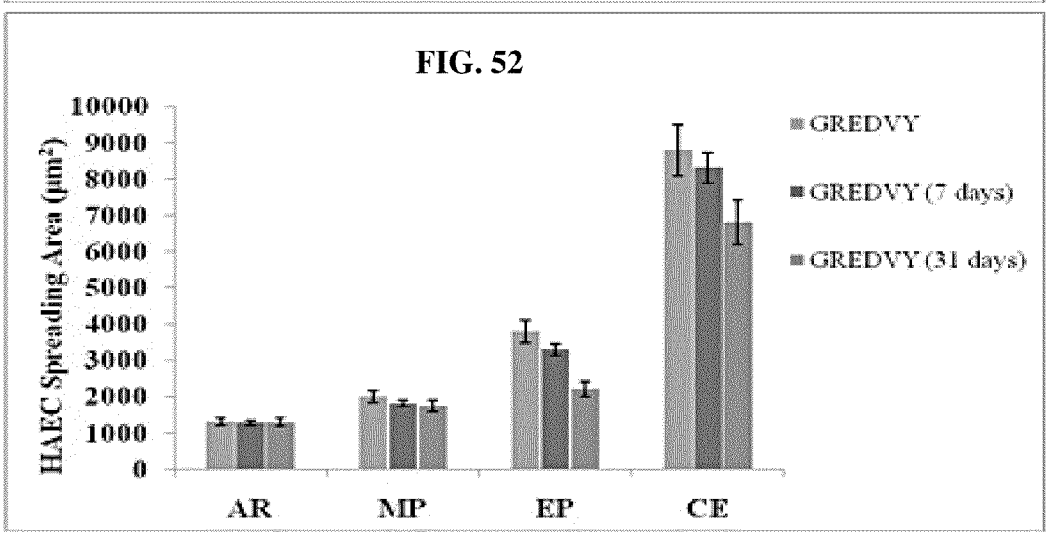

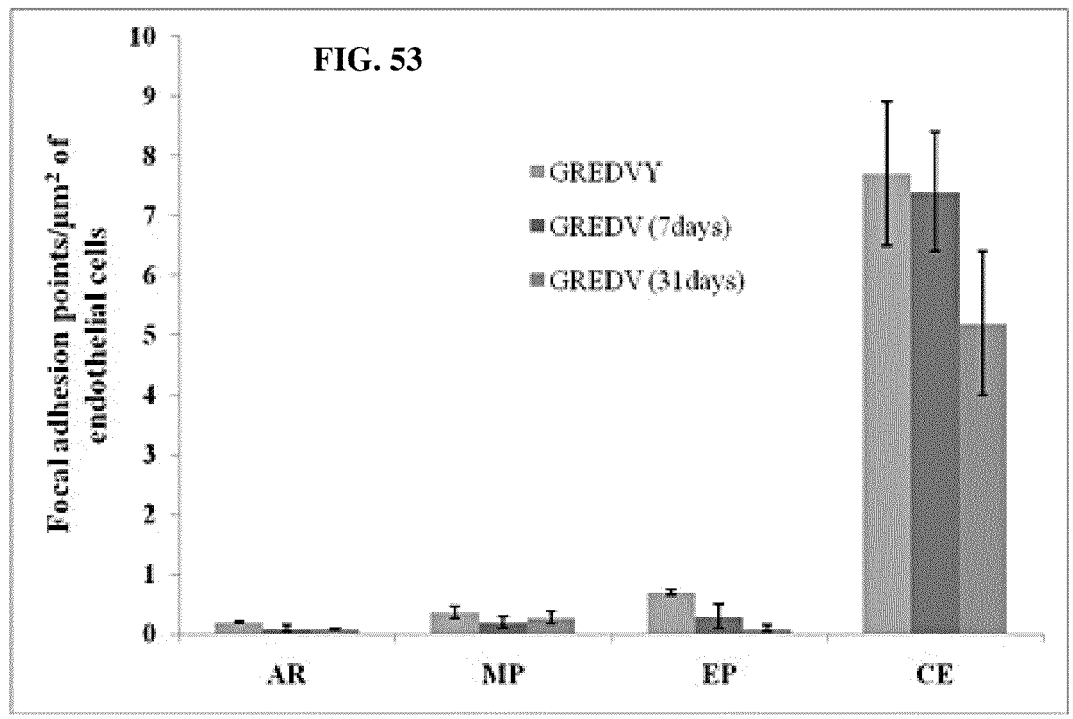
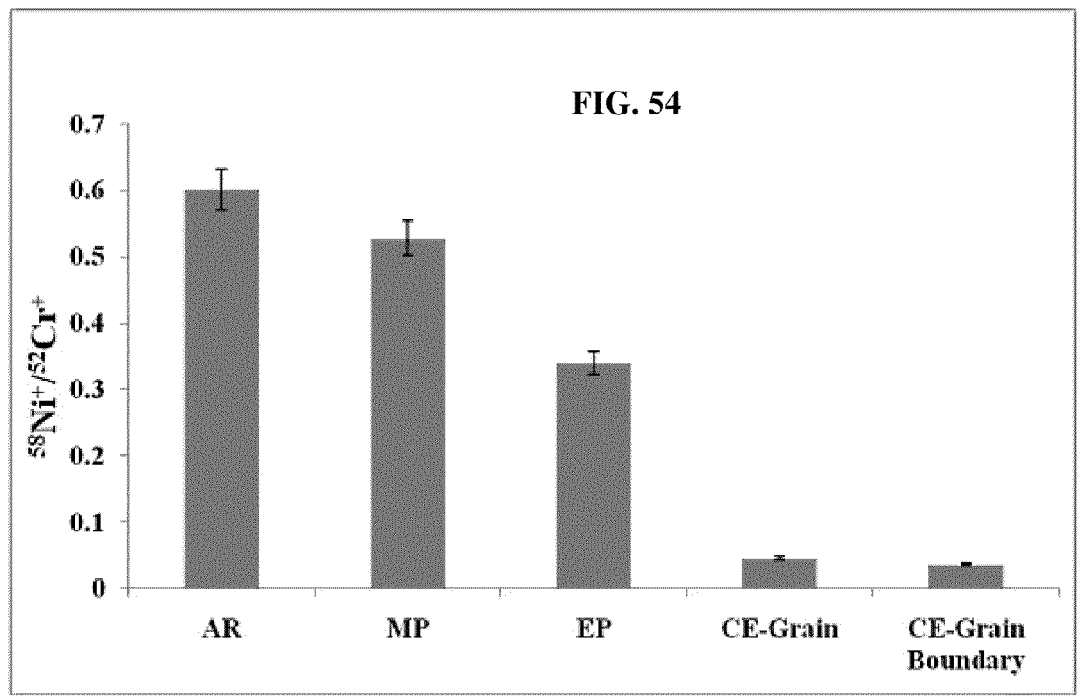

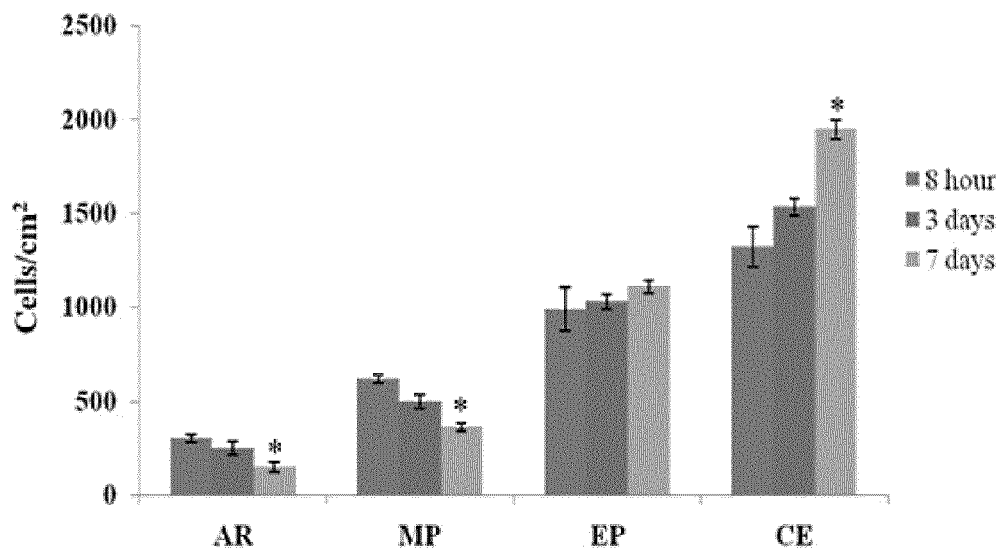
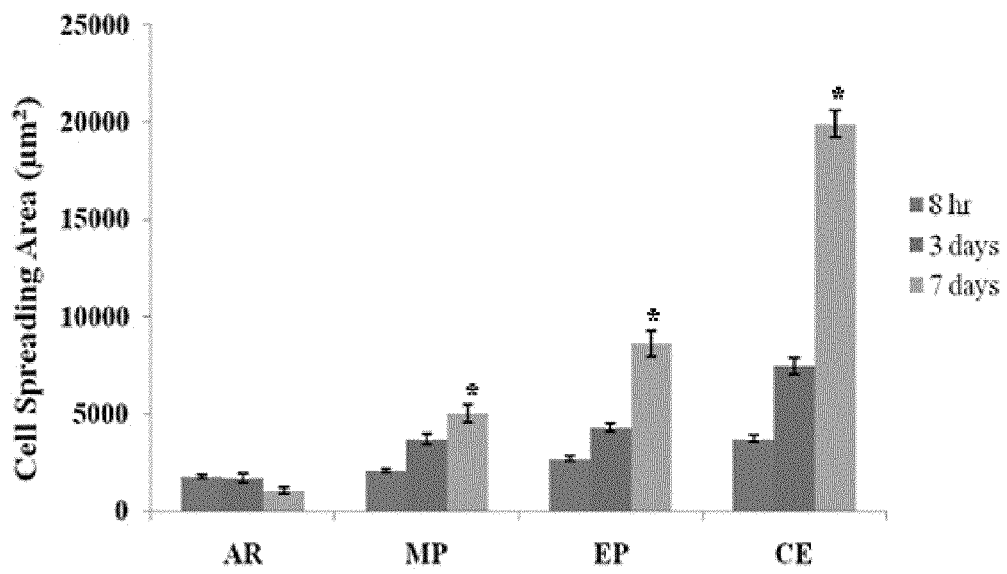

IMPLANTABLE MATERIALS HAVING ENGINEERED SURFACES AND METHOD OF MAKING SAME

CROSS-RELATED APPLICATIONS

This application is a continuation-in-part and claims priority to U.S. patent application Ser. No. 11/091,669, filed Mar. 28, 2005, which claims priority to PCT International Application No. PCT/US03/030383, filed Sep. 26, 2003, which claims priority to U.S. Provisional Application Ser. No. 60/414,031, filed Sep. 26, 2002, all of which are incorporated by reference herein.

BACKGROUND OF THE INVENTION

The present invention relates generally to implantable medical devices and more particularly to controlling surface properties of implantable biocompatible materials suitable for fabrication of implantable medical devices.

Various materials have been used for the purpose of substituting or supporting organic functions of the human body, ranging from metals to ceramics to polymers. Almost all materials currently used are still being optimized in terms of composition and processing. In recent times, the focus has been aiming more and more toward the surface properties of the materials. Since body tissue normally interacts only with the top few nanometers of an implanted material, the chemical and topographic properties often determine the success or failure of an implantation process. Depending on the intended use of an implant, various topographies may be required. The desired surface may be very smooth as in the case of implants directly in contact with the blood flow (e.g. artificial heart valves), a structured surface with very high roughness as in the case of permanent implants where good adhesion and quick cell ingrowth are important (e.g. shafts of hip implants) or surface structures with intermediate roughness. In the case of vascular implants, it has been found that an optimum surface roughness may be beneficial to promote endothelial cell monolayer coverage.

Commonly used techniques for modifying surfaces include chemical treatments, laser structuring as well as mechanical surface treatments. A simple, widespread surface modification technique, with which an increase in surface roughness can be achieved, is grit blasting. An increased roughness may provide both improved adhesion properties and a favored basis for cell growth. Accordingly, grit blasting is applied for permanent implants which require a consolidated ingrowth, e.g. shafts of hip implants and dental implants. The technique is comparatively easy to perform and applicable for large quantities. However, for grit blasted implants it is known that a risk of remaining particles exists. Another limitation results from the fact that mechanical stresses are imposed on the material. When applied to sensitive structures, grit blasting carries the risk of deforming the workpiece. For titanium implants chemical and plasma chemical surface modifications are subject of current research with promising results. In this case highly reactive, mostly fluorine containing chemicals are used in order to etch the surfaces. Similar to grit blasting, with this method the surface roughness can be increased resulting in promoted cell ingrowth.

Another microstructuring method is offered by laser ablation. Using this method three dimensional structures can be created. These structures may be used to promote cell ingrowth; however an even more important feature offered by these structures is the possibility to load the surface with therapeutic substances. This way drugs can be applied directly into the affected location, resulting in a high therapeutic efficacy at small amounts of drugs needed. Examples for drug coatings are antibiotics, antithrombotic agents as well as cell growth stimulants. Other microstructuring techniques that give the possibility to create three dimensional structures originate mainly from the field of microchip fabrication. Photo and laser-lithographic techniques are employed by depositing a protection layer of lacquer on the substrate. Subsequently the features are etched electrochemically into the material. The technique may be time consuming and very difficult to apply for complex geometries like cardiovascular stents.

Accordingly, there is a need for a microstructuring technique that combines the advantages of a selective three dimensional structuring with the convenience of a chemical method for implantable medical devices.

SUMMARY OF THE INVENTION

Provided herein are methods and compositions for implantable materials having engineered surfaces and method of making same. The methods and compositions are set forth in part in the description which follows, and in part will be obvious from the description, or can be learned by practice of the methods, compositions, and systems. In one embodiment, the surface an implantable medical device is chemically etched to provide an engineered surface that promotes endothelialization and improves drug loading/delivery capacity.

BRIEF DESCRIPTION OF THE DRAWINGS

FIG. 7 is a photomicrograph showing the stained focal adhesion points close to the geometric features.

FIGS. 8A-8B are photomicrographs showing the formation of multiple focal adhesion points of a migrating cell and its attachment to the inventive geometric features.

FIGS. 17A-B are fluorescent images of the morphology of human aortic endothelial cells on 316L SS CE surface 110 etched with (7A) Glycergia, (7B) $HNO_3$+HCl.

FIG. 18 is an Scanning electron micrograph (SEM) of a 316L SS CE surface 110 etched with Glycergia depicting smooth grains and grain boundary.

FIG. 35 is a bar graph showing the fluorescent intensity of adsorbed albumin after 120 min on (a) as received (AR), (b) mechanically polished (MP), (c) electrochemically polished (EP) and (d) CE surface 110 (CE) 316L stainless steel substrates (n=15,*p<0.01).

FIG. 36 is a bar graph showing the fluorescent intensity of adsorbed fibronectin after 120 min on (a) as received (AR), (b) mechanically polished (MP), (c) electrochemically polished (EP) and (d) CE surface 110 (CE) 316L stainless steel substrates (n=15,*p<0.01).

FIG. 43 is a bar graph of radiolabeled ($^{125}$I) fibrinogen adsorption on (a) as received (AR), (b) mechanically polished (MP), (c) electrochemically polished (EP) and (d) CE surface 110 (CE) 316L stainless steel substrates.

FIG. 44 is a fluorescence image of anionic dye adsorption on CE surface 110 (CE) 316L stainless steel substrates, where the bright areas indicate more concentration of anionic dye (bar-20 μm).

FIG. 45 is a fluorescence image of cationic dye adsorption on CE surface 110 (CE) 316L stainless steel substrates, where the bright areas indicate more concentration of cationic dye (bar-20 μm).

FIG. 48 is a bar graph showing endothelial cell spreading area after 24 hrs on (a) as received (AR), (b) mechanically polished (MP), (c) electrochemically polished (EP) and (d) CE surface 110 (CE) 316L stainless steel substrates with no peptide and non specific (GRADSP) and specific (GREDVY) peptides adsorbed on the surfaces.

FIG. 49 is a bar graph showing number of focal adhesion contacts per μm$^2$ of endothelial cells after 24 hrs on (a) as received (AR), (b) mechanically polished (MP), (c) electrochemically polished (EP) and (d) CE surface 110 (CE) 316L stainless steel substrates with no peptide and non specific (GRADSP) and specific (GREDVY) peptides adsorbed on the surfaces.

FIG. 50 is a fluorescence image of the morphology of endothelial cells after 24 hrs on CE surface 110 (CE) 316L stainless steel substrates with GREDVY peptide adsorbed on the surface.

FIG. 51 is a bar graph showing endothelial cell density after 24 hrs on (a) as received (AR), (b) mechanically polished (MP), (c) electrochemically polished (EP) and (d) CE surface 110 (CE) 316L stainless steel substrates with GREDVY peptide adsorbed (0 day, 7 days and 31 days shelf life of samples).

FIG. 52 is a bar graph showing endothelial cell spreading area after 24 hrs on (a) as received (AR), (b) mechanically polished (MP), (c) electrochemically polished (EP) and (d) CE surface 110 (CE) 316L stainless steel substrates with GREDVY peptide adsorbed (0 day, 7 days and 31 days shelf life of samples).

FIG. 53 is a bar graph showing number of focal adhesion contacts per μm$^2$ of endothelial cells after 24 hrs on (a) as received (AR), (b) mechanically polished (MP), (c) electrochemically polished (EP) and (d) CE surface 110 (CE) 316L stainless steel substrates with GREDVY peptide adsorbed (0 day, 7 days and 31 days shelf life of samples).

FIG. 54 is a bar graph of nickel-chromium ratio measured as an index of biocompatibility on differently finished 316L stainless steel substrates, assuming that the ion yields of Ni$^+$ and Cr$^+$ are substantially the same in all these similar SS oxide matrices, the ion intensity ratio is a good predictor of the abundance of Ni at the SS surface.

FIG. 55 is a bar graph of the endothelial cell density on (a) as received (AR), (b) mechanically polished (MP), (c) electrochemically polished (EP) and (d) chemically etched 316L stainless steel CE surface 110 (CE) substrates after 8 hrs, 3 days and 7 days (n=25).

FIG. 56 is a bar graph of the endothelial cell spreading area (μm$^2$) on (a) as received (AR), (b) mechanically polished (MP), (c) electrochemically polished (EP) and (d) chemically etched 316L stainless steel CE surface 110 (CE) substrates after 8 hrs, 3 days and 7 days (n=25,* p<0.01).

DETAILED DESCRIPTION OF THE PREFERRED EMBODIMENTS

Figure 1:
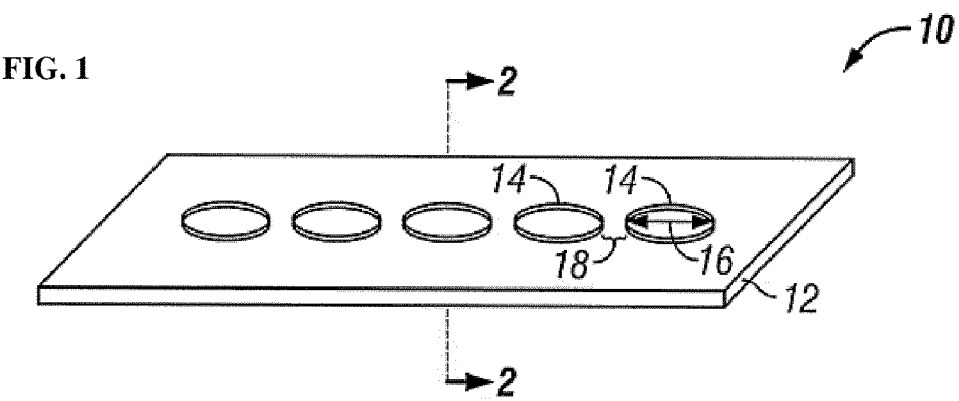
FIG. 1 is a perspective view of an embodiment including evenly distributed elevated geometric features on the surface of an implantable material.

In one embodiment, there is provided an implantable material having at least one blood contact surface comprising an evenly distributed or randomly distributed geometric feature for cell attachment. The evenly or randomly distributed geometric feature on the blood contact surface of the medical device includes: circle dots, square dots, rectangular dots, triangle dots, parallel lines and intersecting lines, or any combination thereof. Additionally, another embodiment provides methods of making a device that has evenly distributed geometric features on the blood contact surface or random distributed geometric features on the blood contact surface.

The relationship between chemically or physiochemically-active geometric features defined and distributed on a blood contact surface enhances endothelial cell binding, proliferation and migration over the blood contact surface of the implantable material. The focal adhesion point formation during cellular movement and the anchorage dependence allows spreading cells to proliferate faster than non-spreading cells. The addition of a patterned array of ultra-thin features having a hydrophobic, hydrophilic or surface energy difference relative to the surface onto which the ultra-thin features are added, enhances the binding, proliferation and migration of endothelial cells to and between the features and across the surface. Use of the term "ultra-thin" is intended to include material thicknesses between about 0.1 μm and 3 μm. Below about 3 μm, the interactions between endothelial cells and the ultra-thin features is primarily chemical and electrochemical. Geometric features having thicknesses greater than 3 μm and up to about 20 μm may also be employed, where as the thickness of the feature increases, there is a decreasing chemical and/or electrochemical interaction between the feature and the endothelial cells and an increasing physical interaction.

Alternatively, by employing UV irradiation to oxidized titanium or titanium-alloy surfaces, photochemical alteration of the surface titanium oxides alter the hydrophobicity of the exposed titanium oxides and act as affinity binding and migration sites for endothelial cell attachment and proliferation across a titanium or titanium-alloy surface. Where UV irradiation is employed, the thickness of the photochemically altered regions of titanium oxide are, for all practical purposes, 0 μm. Thus, within the context of the present application, the term "geometric features" is intended to include both physical members, photochemically-altered regions having thicknesses having thicknesses down to 0 μm, where 0 μm is between 10 to about 999 nm, and chemically etched regions having a grain structure, a grain boundary, and positive charged grain boundaries.

Alternatively, chemical etching (CE) may be employed to create the geometric features. The CE method creates geometric features 14 with a charge difference on the surface 12 leading to a chemical heterogeneity. As shown in FIG. 18, the geometric features 14 may comprise a CE surface 110 including grain structure or crystal 100 and a plurality of grain boundaries 140 surrounding the grain surface structure area. The grain boundary 140 is the dividing structure between two adjacent grain crystals 100 having a different crystallographic orientation. The grain boundaries include a positively charged characteristic as compared to the grain structure 100. The geometric features include a combined effect grain structure and charge difference, which positively affects the endothelialization of the surface. The positive charge of the grain boundaries 140 aids in initial attachment of endothelial cells and the geometric features 14 of the grain boundaries 140 and grain structure 100 as whole promotes increased migration of endothelial cells ultimately leading to enhanced endothelialization. The grain structure 100 includes a positive charge concentration between about −0.2 to −0.3 nN and the grain boundaries 140 include positive charge concentration between about −0.80 to −1.0 nN. The higher positive charge concentration at the grain boundaries may include the characteristic of higher chromium and molybdenum ions on the grain boundaries 140 compared to the grain structure 100. The grain structure may include a Ni/Cr ratio between about 0.04 to 0.05 and the grain boundary 140 may include a Ni/Cr ratio between about 0.025 to 0.03.

Figure 20A:
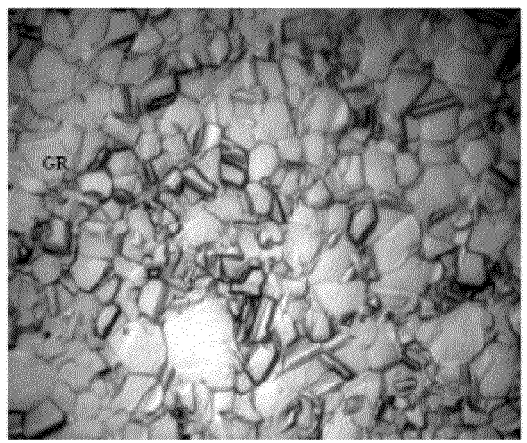
FIGS. 20A-D are optical micrographs of (20A) 16 μm (20B) 31 μm (20C) 47 μm (20D) 66 μm 316L SS substrates showing single phase austenitic (γ) feature and presence of grains (GR), grain boundaries (GB, indicated by arrows) and twin boundaries (TB, indicated by arrows) (bar=20 μm).
Figure 20B:
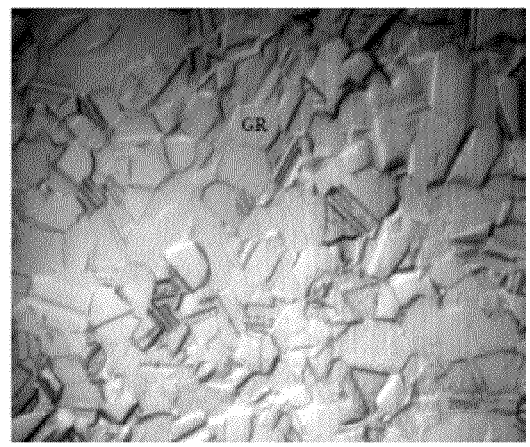
Figure 20C:
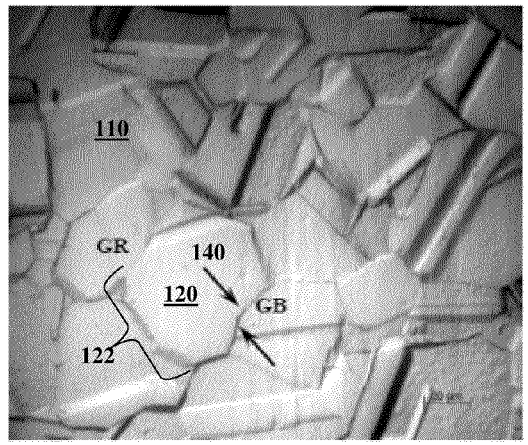

As shown in FIG. 20C, the grain boundary 140 is the dividing surface between two adjacent grain crystals 100 having a different crystallographic orientation. The grain feature 120 and the grain boundaries 140 are three dimensional. The grain boundary 140 includes an abrupt orientation change, occurring over only one or two atomic planes. Because of this, the grain boundary 140 includes atoms that are displaced out of their lattice positions to positions of a lowest energy due to a lattice misfit where the crystals meet. Hence, an increased energy above the normal lattice energy is associated with the displaced atoms at the grain boundary 140, giving rise to a localized grain boundary energy. When the misorientation between the neighboring crystals is small, the displacement of atoms in the boundary from their normal lattice positions is also small, and hence the increase in energy of the boundary above the lattice energy is correspondingly small. The grain boundary energy increases with increasing misorientation between the grains up to a maximum value at relative misorientation of about 10° to 30°.

The CE surface 110 may include an average roughness of about 10-160 μm, a water contact angle of about 10° to about 70°; an adhesion energy between about 0.1343-0.0948 N/m; a grain size surface area of about 10-150 μm; and an approximate width and depth of the grain boundaries between about 1 μm to about 2 μm. The shape of the grain boundaries may include random shapes including, trilateral, quadrilateral, polygonal, pentagonal, hexagonal, heptagonal, octagonal, or any combination thereof. The dimensions of the grain structure may include deep and narrow crevices, protrusions, smooth grains and dividing grain boundaries. Alternatively, the CE surface may be grafted with a peptide Gly-Arg-Glu-Asp-Val-Tyr (GREDVY) to promote endothelialization, or YIGSR (tyr-lle-gly-ser-arg), IKVAV (lle-lys-val-ala-val), REDV (arg-glu-asp-val), LDV (leu-asp-val), DGEA (asp-gly-glu-ala), GRGDY (gly-arg-gly-asp-tyr), YGRGD (tyr-gly-arg-gly-asp), GRGDSP (gly-arg-gly-asp-ser-pro), RGD (Arg-Gly-Asp), or REDV (arg-glu-asp-val).

Alternatively, the CE surface 110 functions as a drug release system 200 including for a drug coating along the grain boundaries 140 and within the grain structure 100 for negatively charged drugs, further explained below. The grain structure 100 may comprise a depth and width ratio in the range of about 0.5 to 1. The grain boundaries 140 act as notches and the grain structure acts as a depot with a rounded base, where a depot of 10 μm depth and 5 μm width, includes a notch radius of 2.5 μm and a ratio of depth to notch radius of 4. Negatively charged drugs may be selected from the group consisting of hydrophobic pharmacologically active agents, hydrophilic pharmacologically active agents, antibiotic drugs, antiviral drugs, neoplastic agents, steroids, fibronectin, anti-clotting drugs, anti-platelet function drugs, drugs which prevent smooth muscle cell growth on inner surface wall of vessel, heparin, heparin fragments, aspirin, coumadin, tissue plasminogen activator, urokinase, hirudin, streptokinase, antiproliferatives, antioxidants, antimetabolites, thromboxane inhibitors, non-steroidal and steroidal anti-inflammatory drugs, immunosuppresents, such as rapomycin, beta and calcium channel blockers, genetic materials including DNA and RNA fragments, complete expression genes, antibodies, lymphokines, growth factors, prostaglandins, leukotrienes, laminin, elastin, collagen, nitric oxide, and integrins.

In FIG. 1, a portion of an implantable material 10 showing the surface material 12 with described elevated geometric features 14 is illustrated. The geometric features are elevated from the surface of the implantable material to a height ranging from about sub-micron to about 20 μm. Preferably, the height of the geometric feature 14 ranges from about sub-micron to about 3 μm. The shape of geometric features can be either circular, square, rectangle, triangle, parallel lines, straight or curvilinear lines or any combination thereof. In one embodiment, the geometric features is from about 10 μm to about 75 μm, alternatively from about 15 μm to 50 μm in feature width 16, or feature diameter if the geometric feature is circular. In one embodiment, a gap distance 18 between each of the geometric features should generally be the same as the feature width 16, i.e., between about 10 μm to about 75 μm edge-to-edge. Alternatively, there is no gap distance 18 between each of the geometric features, as in the geometric features on the CE surface 110.

Figure 2:
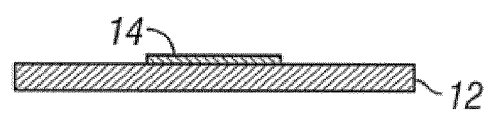
FIG. 2 is cross-sectional view of FIG. 1 along line 2-2.

FIG. 2 is a cross-sectional view along line 2-2 in FIG. 1. One of the elevated geometric features 14 is shown on the surface 12 of the implantable material.

Figure 3:
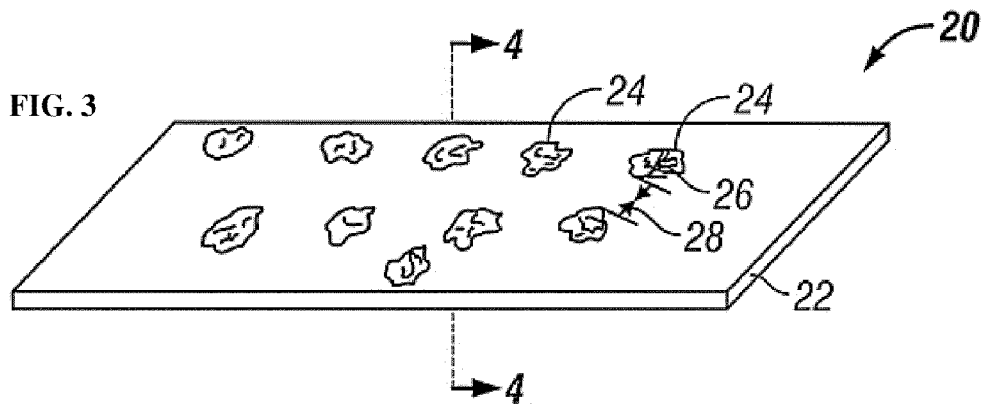
FIG. 3 is a perspective view of an embodiment including evenly distributed chemically defined geometric features on the surface of an implantable material.

In FIG. 3, a titanium or titanium-alloy material 20 is heating to oxidize and form titanium dioxide on the surface of the material 20, and then the geometric features 24 are formed by exposing the material 20 to UV through a pattern mask. UV irradiation alters the titanium oxides in the areas of features 24, thereby chemically altering the geometric features 24 relative to the surrounding the surrounding surface area 22 of material 20. The shape of geometric features can be circular, square, rectangle, triangle, parallel lines, intersecting lines or any combination. In one embodiment, each of the geometric features formed by UV irradiation is from about 10 μm to about 75 μm, alternatively from about 15 μm to 50 μm in feature width 16, or feature diameter if the geometric feature is circular. In one embodiment, the gap distance 28 between each component of the geometric features is in the same magnitude as the feature width 26.

Figure 4:
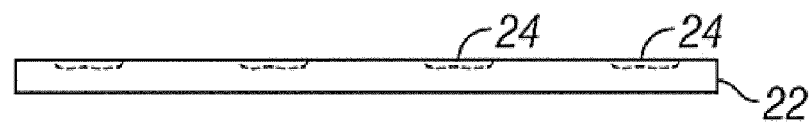
FIG. 4 is a cross-sectional view of FIG. 3 along line 4-4.

FIG. 4 is a cross-sectional view of FIG. 3 along line 4-4. The described geometric features 24 are indicated by the dotted lines, which indicate that the geometric features 24 are at the same level of the surrounding surface 22, in one embodiment.

Figure 5:
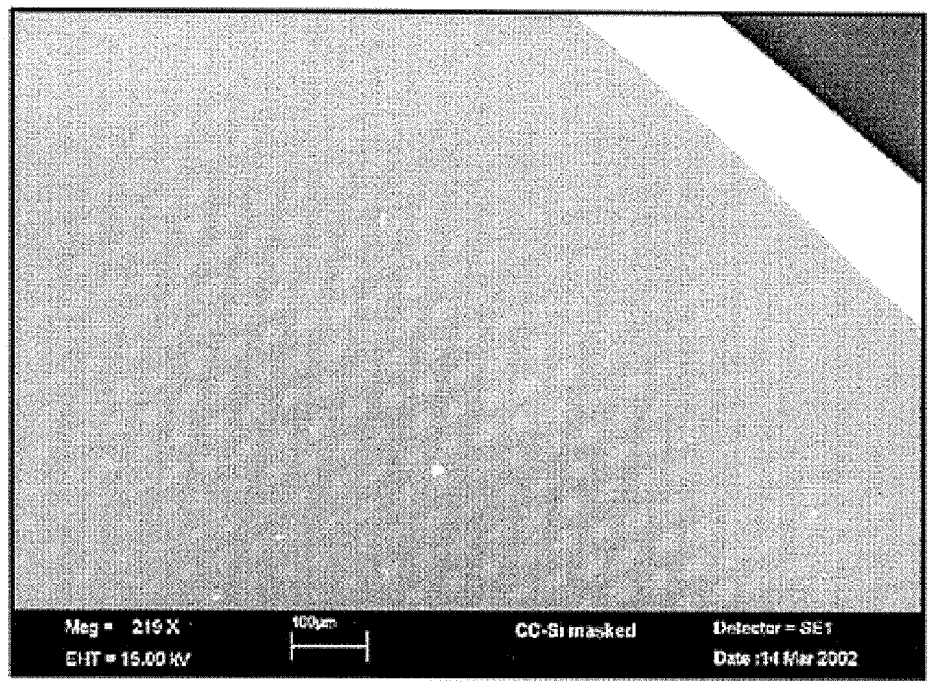
FIG. 5 is a photomicrograph showing an embodiment including geometric features as carbon coated silicon.

FIG. 5 shows geometric features that are evenly distributed across the at least one surface of the implantable material that contacts body fluid, preferably blood. As disclosed in FIG. 1 and FIG. 2, the geometric features are elevated from the rest of the surface to a height ranging from about sub-micron to about 20 micrometer. Preferably, the height of the geometric feature ranges from about sub-micron to about 3 micrometer. The shape of the geometric features is not confined within the shape that is shown. The shape of the chemically defined domain can also be any of circle, square, rectangle, triangle, parallel lines, intersecting lines or any combination of the above.

Figure 6A:
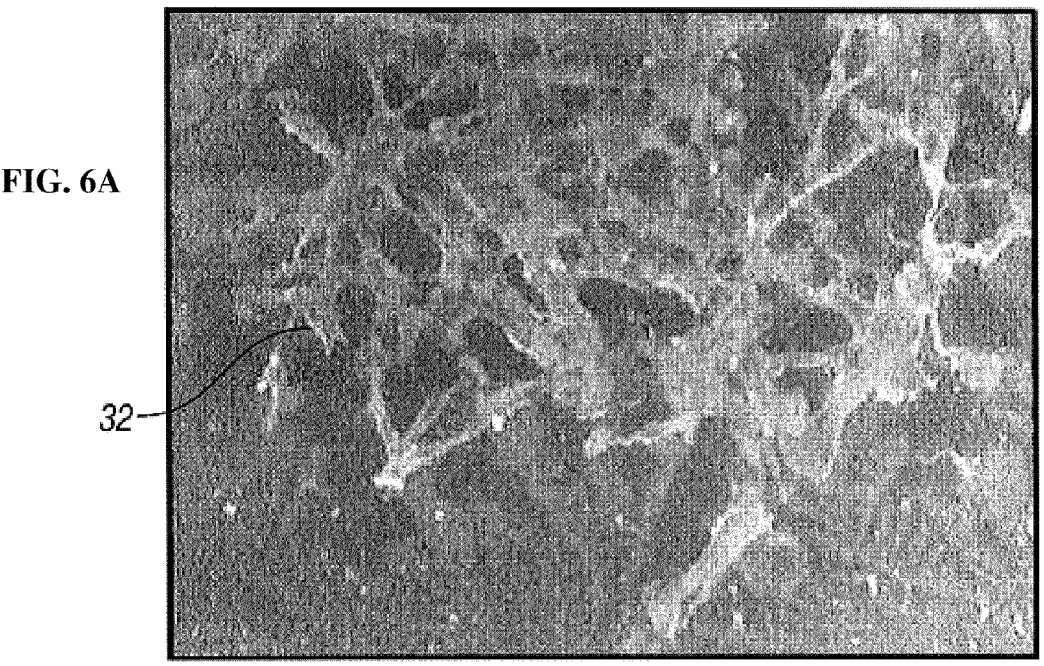
FIGS. 6A-6C are photomicrographs showing cellular migration on the surface with no inventive geometric features versus on the surface with inventive features.
Figure 6B:

FIG. 6A shows the cell 32 spreading on the surface of hydrophilic treated Si. FIG. 6B shows the cell 32 spreading on the surface of hydrophilic treated Si with circular dots that are 15 microns in diameter. Cells in FIG. 6B appear to have much more focal adhesion points 36 than those in FIG. 6A. Because these geometric features provide for cell attachment, acting as affinity domains, the size of each of these affinity domains relative to the size of an endothelial cell determines the availability of affinity domains to the subsequent round of cell movement. According to one embodiment, the preferred size of each of the individual component of the geometric features is about 10 μm to about 75 μm, and preferably from about 15 μm to 50 μm in feature width, or diameter if the geometric feature is circular. As described in the background section, focal adhesion point formation is the critical step in cell movement and cell proliferation; therefore, geometric features such as carbon dots on the hydrophilic Si surface promote cell movement. Promoting cell movement and cell proliferation ultimately accelerates covering of the implanted implantable material with endothelial cells on exposed surfaces having the geometric features. Although the geometric features shown in FIG. 6B are circular, the shape of the geometric features are not limited to this particular embodiment.

Figure 6C:
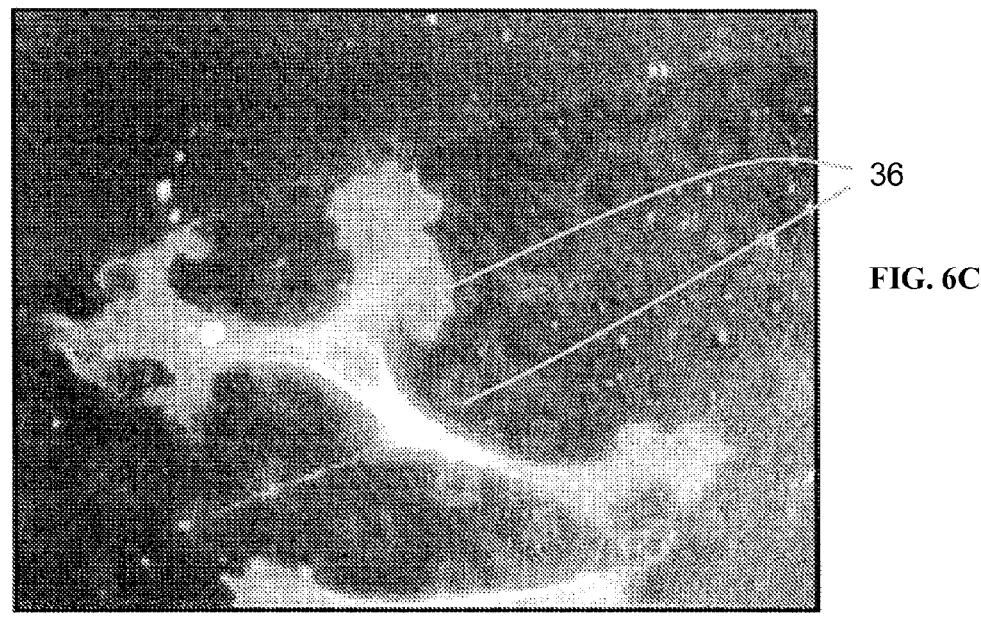

FIG. 6C is a magnification of a portion of the image of FIG. 6B. Multiple focal adhesion points 36 are again shown. Wide spreading of the cell is primarily due to the formation of multiple focal adhesion points on the circular geometric features. Extensive spreading of the cells is beneficial towards endothelialization because it promotes cell movement and cell proliferation.

FIG. 7 shows the stained focal adhesion points 36 of human aortic endothelial cells (HAEC) on the surface of an implantable material with geometric features 14 that are in the form of carbon dots. The focal adhesion points are located at or very close to the geometric features 14. As described in the background section, these focal adhesion points serve as tension points for the cell to contract from the opposite end of the cell and hence promote cell movement.

FIG. 8A shows the wide spreading of cells 32 and focal multiple focal adhesion points 36 on the surface of an implantable material with geometric features that are in the form of NiTi dots of 25 micrometers in diameter. The NiTi dots are invisible due to the weak contrast between the NiTi dots and surrounding Si surface.

Figure 8B:
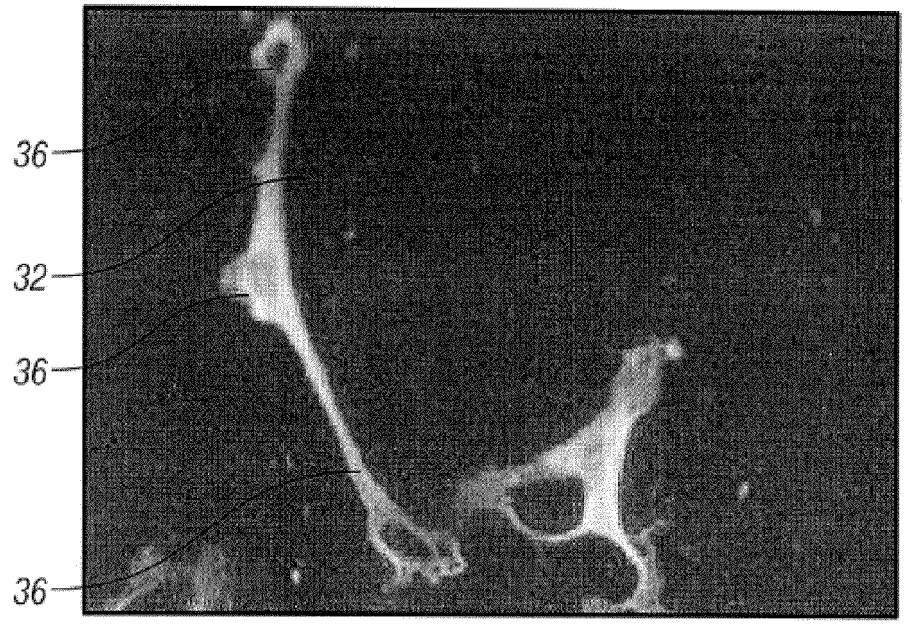

FIG. 8B shows a magnified slide of a human aortic epithelial cell 32, as shown in FIG. 8A. Multiple focal adhesion points 36 are shown to encapsulate the NiTi dots patterned on the hydrophilic Si surface.

Figure 9A:
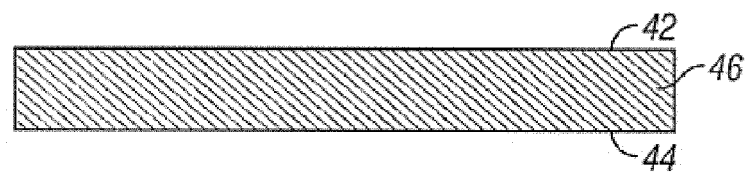
FIGS. 9A-9D are cross-sectional diagrammatic views of an embodiment, the combination of a-d representing the steps to make an inventive implantable material with elevated geometric features.

Referring to FIG. 9A, a portion of an implantable material 46 with surface 42 and 44 is shown.

Figure 9B:
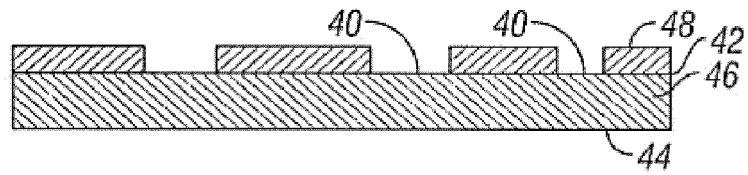

Referring to FIG. 9B, a machined mask 48 having laser-cut holes 40 of defined size ranging from about 10 μm to about 75 μm, and preferably from about 15 μm to 50 μm, patterned throughout coats at least one surface 42 of the implantable material 46 and is tightly adhered to the covered surface 42.

Figure 9C:
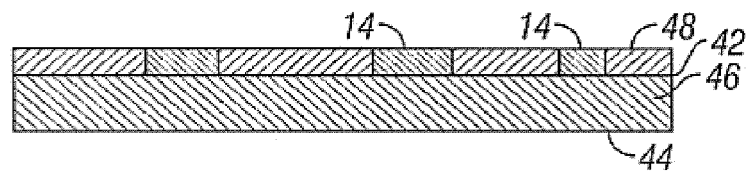

Referring to FIG. 9C, a thin film of material 14 was deposited into the space as defined by the holes 40, as seen in FIG. 9B, in the mask 48 by thin film deposition procedures.

Figure 9D:
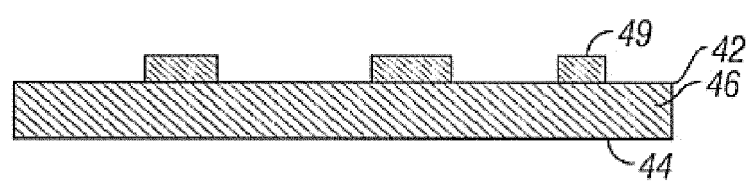

Referring to FIG. 9D, after deposition, the mask is removed to reveal the geometric features 49 patterned across the at least one surface 42 of the implantable material 46.

As described above, the shape of the holes in the mask could be in any of the shapes described for the geometric features including: circle, square, rectangle, triangle, parallel lines and intersecting lines, or any combination thereof. In the thin film deposition embodiment of the manufacturing the geometric features, the geometric features are elevated from the surface of the implantable material. The thickness of the geometric features is based upon the thickness of the holes in the mask, the thickness ranging from about sub-micron to about 20 micrometer. Preferably, the thickness of the holes in the mask range from about sub-micron to about 3 micrometer.

In accordance with an alternate embodiment, the substrate for the implantable medical device is formed of titanium, nickel-titanium alloy or other titanium-rich alloy metals, which is oxidized to convert surface titanium to titanium dioxide, then covered with a pattern-mask and exposed to high intensity UV irradiation. Titanium dioxide ($TiO_2$) absorbs UV radiation and may be used in a variety of applications as a UV inhibitor to prevent UV transmission across a $TiO_2$ barrier layer. Upon exposure to UV irradiation, an originally hydrophobic and oleophilic titanium oxide layer becomes amphiphilic. The effect of UV irradiation on a titanium oxide surface occurs, because of unsymmetrical cleavage of the Ti—O bond to leave $Ti^{3+}$ ions on the surface in some regions. These amphiphilic surfaces may be used in a range of technological applications, such as self-cleaning paints and anti-misting glasses. Zarbakhsh, A., Characterization of photon-controlled titanium oxide surfaces, ISIS Experimental Report, Rutherford Appelton Laboratory, May 16, 2000, herein incorporated by reference.

The amphiphilic state of the UV irradiated titanium oxide may be employed as an alternative to depositing patterned features onto the implantable substrate surface. An implantable substrate fabricated of titanium or a titanium alloy is masked with a pattern mask having a plurality of openings passing there through. As with the above-described embodiment, the plurality of openings preferably have a size and special array selected to define affinity binding domains and cellular migration cites for promoting endothelial cell binding and proliferation across the substrate surface. The open surface area of each of the plurality of openings in the pattern mask is preferably in the range of between about 10 to 75 μm, and with adjacent pairs of openings being in a spaced apart relationship such that a distance of about 10 to about 75 μm exists between the openings, the inter-opening distance corresponding to the size of the opening. By interposing the pattern mask between a UV source and the substrate surface, a pattern of UV irradiated regions is imparted to the substrate surface, thereby altering the titanium dioxides present at the irradiated regions and forming affinity domains at the substrate surface.

Figure 10A:
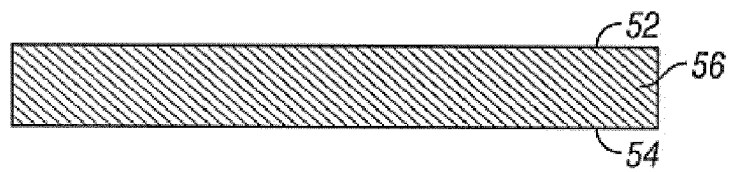
FIGS. 10A-10D are cross-sectional diagrammatic views of an embodiment, the combination of a-d representing the steps to make an inventive implantable material with chemically defined geometric feature.

Referring to FIG. 10A, a portion of an implantable material 56 made of titanium or a titanium-alloy is shown having at least one surface 52 and 54 that is oxidized by heating or an equivalent known by the person skilled in the art.

Figure 10B:
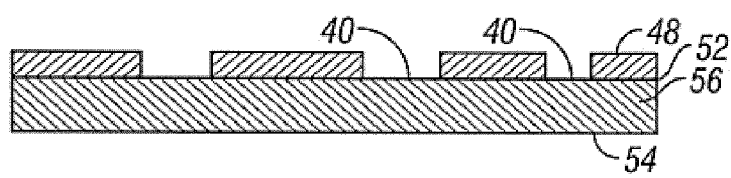

Referring to FIG. 10B, a machined mask 48 that had laser-cut holes 40 of defined size from 10 μm to about 75 μm, and preferably from about 15 μm to 50 μm, patterned throughout to coat the at least one surface 52 of the implantable material 56 and is tightly adhered to the covered surface 52.

Figure 10C:
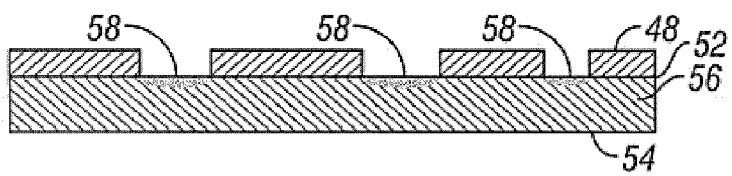

Referring to FIG. 10C, the implantable material 56 covered with the mask 48 is then illuminated by the ultraviolet rays. Because $TiO_2$ is sensitive to ultraviolet, the chemical composition in holes 58 is different from the area that is covered by the mask. In contrast to the geometric features illustrated in FIG. 9C, the geometric features 59 in FIG. 10C is not elevated relative to the surrounding surface of the implantable material.

Figure 10D:
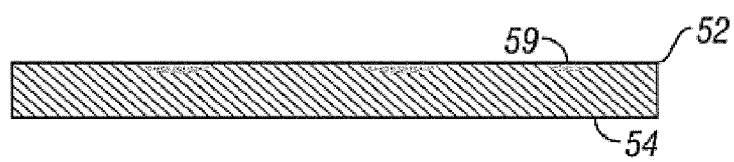

Referring to FIG. 10D, after ultraviolet irradiation, the mask is removed to reveal the surface 52 that surrounds the geometric features 59 formed by ultraviolet irradiation. In one embodiment, because the shape of the holes 58 in the mask 48 could be in any of the shapes described for the geometric features including: circle, square, rectangle, triangle, parallel lines and intersecting lines, and combinations thereof, the geometric features 58 accordingly adopts such shapes also.

EXAMPLE I

UV Irradiated Geometric Feature

Nickel-titanium sheets were heated to oxidize titanium present at the surface of the sheet. Pattern masks fabricated from machined metal were laser drilled a pattern of holes having diameters ranging from 15 μm to 50 μm, with a single diameter of holes on each pattern mask. A single pattern mask was placed over a single nickel-titanium sheet and the assembly was exposed to high intensity ultra-violet irradiation. After UV irradiation, the irradiated nickel-titanium sheet was placed on a fully endothelialized test surface and maintained at 37° C. under simulated in vivo flow conditions and under static flow conditions. Qualitative observations were periodically made and it was found that endothelial cells bound to the pattern of UV irradiated affinity domains and migrated across the nickel-titanium sheet by proliferating across the pattern of affinity domains, eventually fully forming an endothelium on the nickel-titanium sheet.

EXAMPLE II

Geometric Feature CE Surface Microstructure for Enhanced Endothelialization

In an alternative embodiment, the geometric features may be formed by a microstructuring method comprising chemical etching of a biocompatible metal to form a pattern of geometric features 14 on the at least one surface 12 of the biocompatible metal, as shown in FIG. 18. The microstructuring method may be used in the manufacturing of implantable medical devices 10 such as stents, stent-grafts, grafts, valves, shunts and patches, as a method for increasing endothelialization and creating a release system 200 without the use of protective polymers. The geometric features 14 create a charge difference on the surface 12 leading to a chemical heterogeneity. The geometric features 14 may comprise a chemically etched (CE) surface including a grain structure 100 and a plurality of grain boundaries 140 including a positively charged characteristic as compared to the grain structure 100. The geometric features include a combined effect grain structure and charge difference, which positively affects the endothelialization of the surface. The positive charge of the grain boundaries 140 aids in initial attachment of endothelial cells and the geometric features 14 of the grain boundaries 140 and grain structure 100 as whole promotes increased migration of endothelial cells ultimately leading to enhanced endothelialization.

In one embodiment, the geometric features may include an approximate width and depth of the grain boundaries between about 1 μm and 2 μm; an average roughness of about 10-160 μm, a water contact angle of about 10° to about 70°, a density of human aortic endothelial cells of about 400-5000/cm , a HAEC spreading area of about 450-5000 $\mu m^2$, and a focal adhesion points/$\mu m^2$ of HAEC of about 0.5-3.00/$\mu m^2$. The shape of the geometric feature may include random shapes including trilateral, quadrilateral, polygonal, pentagonal, hexagonal, heptagonal, octagonal, circular, or any combination thereof. The dimensions of the geometric features may include deep and narrow crevices, protrusions, smooth grains and dividing grain boundaries.

Alternatively, a release system 200 includes a pattern of geometric features 14 formed from the chemical etching method including a strong adhesion characteristic for a drug coating and, after elution of the drug, serve to promote the endothelialization properties of the surface. The chemical etching method may be used to create randomly distributed geometric features. In contrast to mechanical roughening procedures, the surfaces can be created without mechanical strains. The chemical etching method includes featured implant surfaces as a basis for drug coatings. Endothelial cell attachment is increased and the drug amount on the surface and the adhesion of the drug. The etching method on stents includes grain boundaries with a higher amount of drug on the stent and more human aortic endothelial cell attachment as compared to commercially used electropolished stents. Alternatively, a combination of special etching techniques generates a plurality of micro-depots within the at least one surface of the biocompatible metal to store drugs within the surface.

Biocompatible metals include, but are not limited to, stainless steel, titanium, nitinol, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys.

In one embodiment, the at least one surface 12 of the biocompatible metal is mechanical polished before the chemical etching method. In one embodiment, the biocompatible metal may be polished using abrasive papers of different grit sizes and a final polishing may use a nylon polishing cloth on the grinder/polisher. The final polishing step may be performed for 15-30 minutes. After the polishing, the surface may be cleaned with a detergent and acetone in an ultrasonic cleaner at 60° C. in two different steps of 10 min. The detergent may include Extran™ or other detergents generally known. Finally, the surface is rinsed in double distilled water for 5 min as the final preparation step prior to etching Different etching reagents may be used and include, but are not limited to, Glycergia ($HNO_3+HCl+C_3H_5(OH)_3$), nitric acid ($HNO_3$)+orthophosphoric acid ($H_3PO_4$), nitric acid ($HNO_3$)+hydrochloric acid (HCl), nitric acid ($HNO_3$)+glycerol ($C_3H_5(OH)_3$), nitric acid ($HNO_3$), hydrochloric acid (HCl), and orthophosphoric acid ($H_3PO_4$). The etching reagents can be used in different concentrations. Specific etching reagents may be used for certain biocompatible metals. For example, $HF+HNO_3+H_2O$ may be used for nitinol (nickel titanium) in the ratio 1:4:5. Depending on the surface of the nitinol, the concentration may vary. By etching nitinol with $HF+HNO_3+H_2O$ and optimizing the etching time, the nitinol microstructure will be revealed. Etching time can be varied between 10 seconds to 5 minutes. Increasing the etching time deepens the grain boundaries but it may corrode the surface and affect its biological performance; therefore, an optimized etching time may be used. And the grain structures and different phases that are revealed after etching depends on the processing condition of the material or the route by which the material is manufactured. Nital (1-10 mL $HNO_3$, 90-99 mL ethanol or methanol) may be used as the etchant for Fe, carbon and alloy steels, cast irons to reveals alpha grain boundaries and constituents. The 2% Nital solution may be used by immersion for up to 60 seconds or by swabbing and the 5-10% solution is used for high-alloy steels. Picral (4 g picric acid, $((NO_2)_3C_5H_2OH)$/100 mL ethanol) may be used for structures consisting of ferrite and carbides, and the addition of approximately 0.5-1% zephiran chloride improves etch rate and uniformity. Alkaline sodium picrate (ASP) (2 g picric acid $((NO_2)_3C_6H_2OH)$), immersing sample in solution at 60-70C for 1-3 min. Klemm I (50 mL sat aq. Sodium thiosulfate ($Na_2S_2O_3.5H_2O$) 1 g potassium metabisulfite ($K_2S_2O_5$), immersing sample for 40-100 s. Beraha CdS (240 g aq. Sodium thiosulfate ($Na_2S_2O_3.5H_2O$), 30 g citric acid, 20-25 g cadium chloride ($CdCl_2. 2.5H_2O$), 100 mL distilled water) to tint etch for iron, steel, cast irons, ferritic and martensitic stainless steel. Murakami reagent (10 g potassium ferricyanide ($K_3Fe(CN)_6$), 10 g potassium hydroxide or sodium hydroxide, 100 mL distilled water) tints chromium carbides. Lichtenegger and Bloech I (20 g ammonium bifluoride ($NH_4F.HF$), 0.5 g potassium metabisulfite ($K_2S_2O_5$), 100 mL distilled water) tints austenitic Cr—Ni alloys. $HNO_3+$ HCl, also known as Aqua Regia may also be used for iron based alloys for example, stainless steel for iron based alloys for example, stainless steel.

Figure 11A:
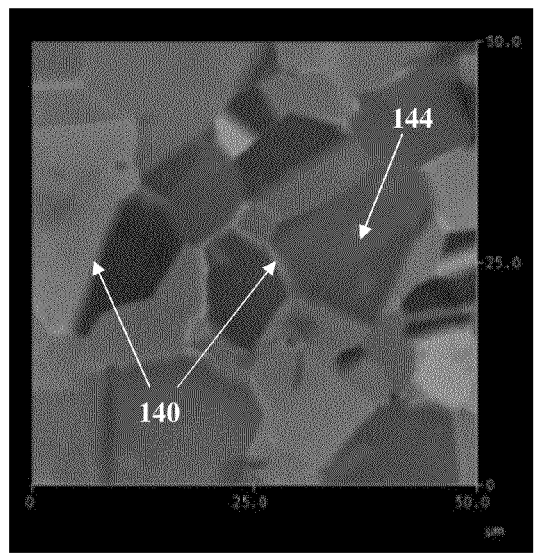
FIGS. 11A-G are AFM pictures showing CE surface 110 substrates treated with different etchants: Glycergia ($HNO_3$+HCl+$C_3H_5(OH)_3$) (FIG. 11A); nitric acid ($HNO_3$)+orthophosphoric acid ($H_3PO_4$) (FIG. 11B); nitric acid ($HNO_3$)+hydrochloric acid (HCl) (FIG. 11C); nitric acid ($HNO_3$)+glycerol ($C_3H_5(OH)_3$) (FIG. 11D); nitric acid ($HNO_3$) (FIG. 11E); hydrochloric acid (HCl) (FIG. 11F); and orthophosphoric acid ($H_3PO_4$) (FIG. 11G).
Figure 11B:
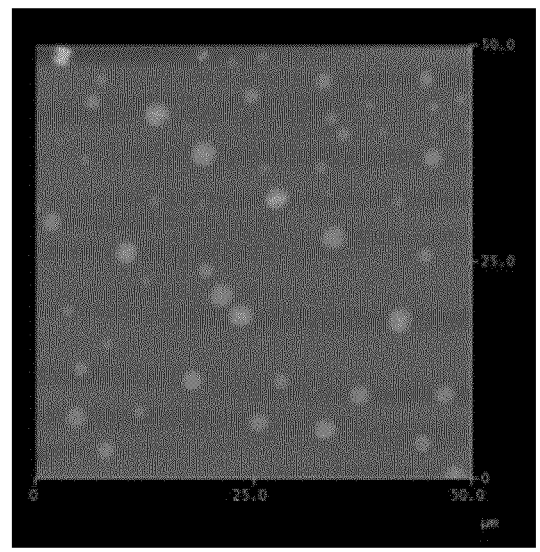
Figure 11C:
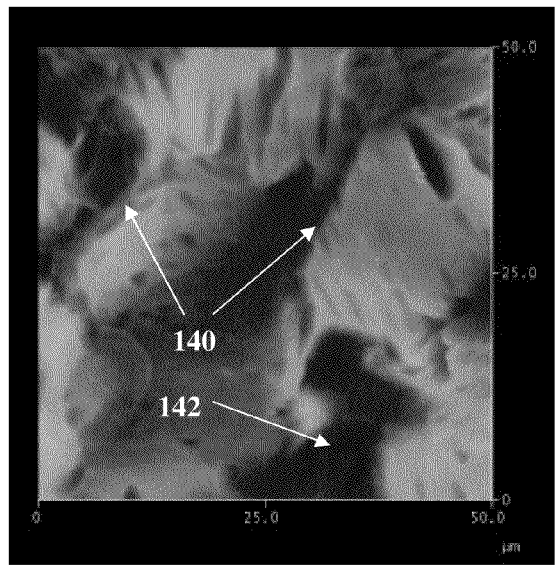
Figure 11D:
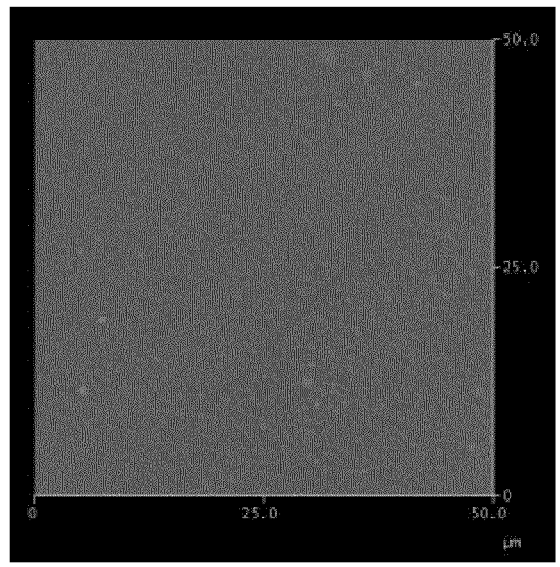
Figure 11E:
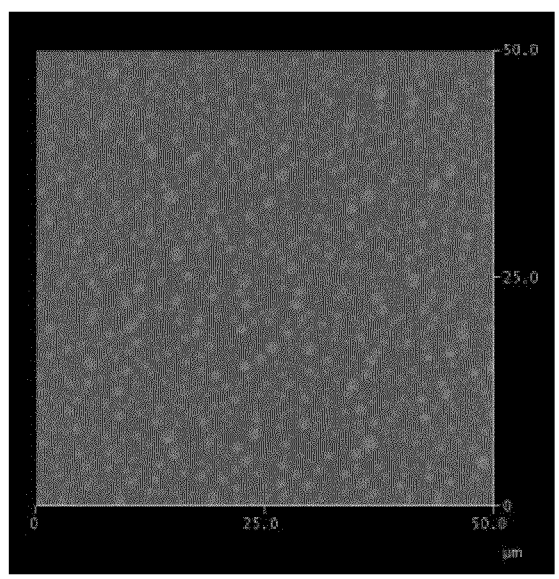
Figure 11F:
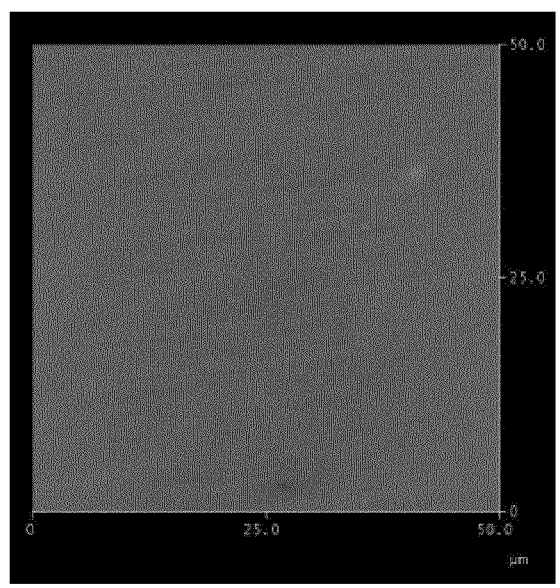
Figure 11G:
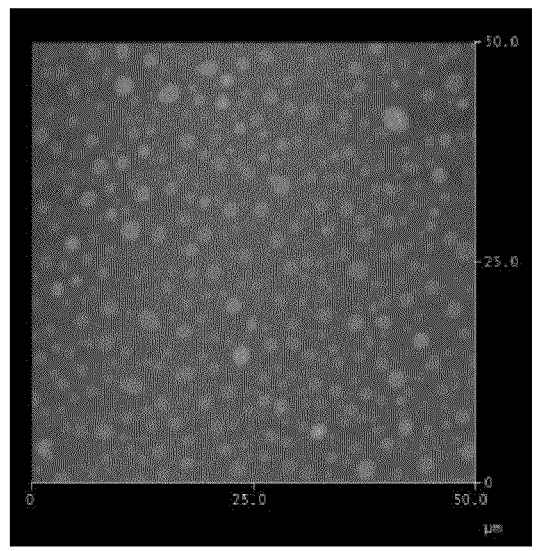

In one embodiment, a small pool of etchant is created on the biocompatible metal surface, the surface is cleaned in double distilled water and acetone in an ultrasonic bath for 20 min to eliminate all acid remains. Etching time and composition for all etchants are optimized. In one example, different etching times from 10 seconds to 5 minutes may be used. In another example, etching times from 5 minutes to 2 hours may be used. Composition of etching reagent and time of etching may be optimized so as to promote maximum endothelial cell attachment, obtain a surface morphology that is free of pits and protrusions, and to avoid over etching Optical microscopy (Zeiss Axioplan 2 Imaging) and Atomic Force Microscope (AFM) may be performed on the etched samples. As shown in FIGS. 11A-G, the AFM pictures show the influence of the different surface treatments on the morphology of the 316L SS surfaces. The etching process may influence the surface morphology of the substrates in different ways depending on the nature of the etchant. FIGS. 11A-G shows substrates treated with different etchants: Glycergia ($HNO_3+HCl+C_3H_5(OH)_3$) (FIG. 11A); nitric acid ($HNO_3$)+orthophosphoric acid ($H_3PO_4$) (FIG. 11B), nitric acid ($HNO_3$)+hydrochloric acid (HCl) (FIG. 11C), nitric acid ($HNO_3$)+glycerol ($C_3H_5(OH)_3$) (FIG. 11D), nitric acid ($HNO_3$) (FIG. 11E), hydrochloric acid (HCl) (FIG. 11F) and orthophosphoric acid ($H_3PO_4$) (FIG. 11G). The different etchants used for etching lead to different surface morphologies as evident from the AFM micrographs.

Surfaces etched with Glycergia ($HNO_3+HCl+C_3H_5(OH)_3$) (FIG. 11A) and nitric acid ($HNO_3$)+hydrochloric acid (HCl) (FIG. 11C) show a grain boundary structure 140. The surfaces etched with nitric acid ($HNO_3$)+hydrochloric acid (HCl) show deep grain-boundary trenches 142, with edges are well visible and grain centers that are rough. Surfaces etched with Glycergia show grains with smooth grain centers 144, separated by grain boundaries 140, which have even but sharp edges with no evidence of pits or holes. Surfaces etched with Glycergia and nitric acid could be used for drug loading and elution. The surface etched with HCl show a completely homogeneous and flat surface. Examination of the surfaces etched with nitric acid ($HNO_3$)+orthophosphoric acid ($H_3PO_4$) (FIG. 1IB), nitric acid ($HNO_3$)+glycerol ($C_3H_5(OH)_3$) (FIG. 11D), nitric acid ($HNO_3$) (FIG. 11E) and orthophosphoric acid ($H_3PO_4$) (FIG. 11G) shows the creation of evenly distributed protrusions that become visible at high magnifications.

Figure 12:
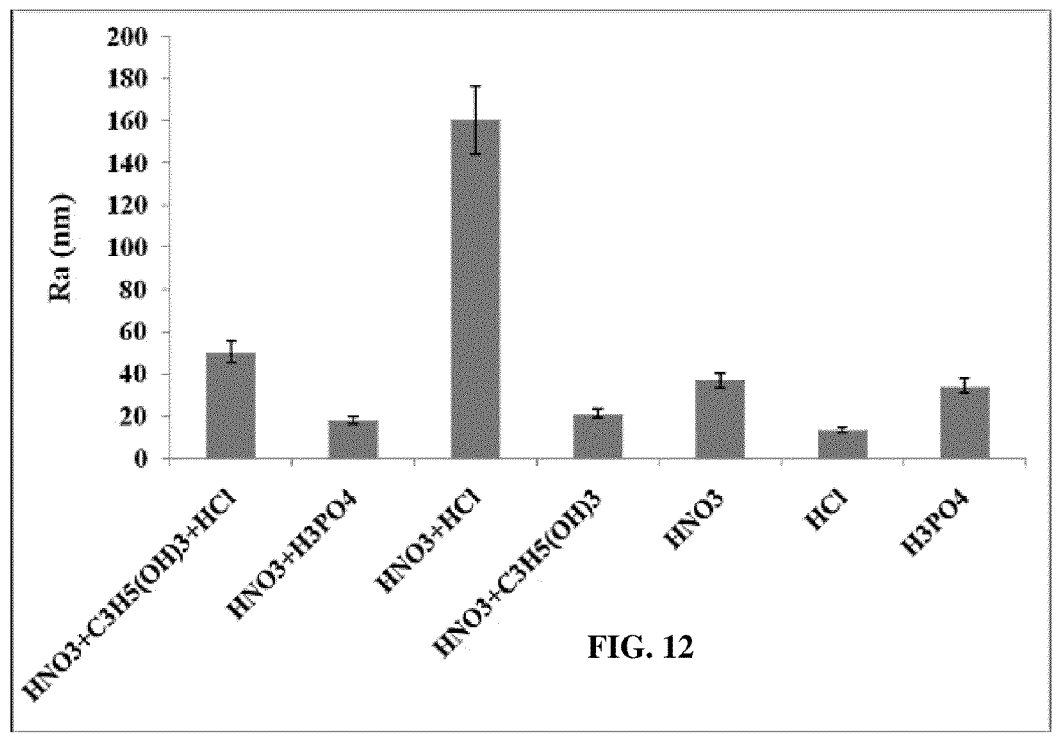
FIG. 12 is a graph of the average roughness (Ra) values of 316L SS CE surface 110 etched with different etching reagents (n=25,*p<0.001).

FIG. 12 shows a comparison of roughness values, as measured by a Veeco Digital Instruments Dimension 3100 AFM, for 316L SS samples etched with different etching reagents based on data similar to those shown in FIGS. 11A-G. Since the etched surfaces showed difference in surface morphology, the average roughness values also varied. Statistically significant differences in the roughness values were observed between the samples etched with Glycergia ($HNO_3+HCl+C_3H_5(OH)_3$), nitric acid ($HNO_3$)+hydrochloric acid (HCl) and nitric acid ($HNO_3$) and also as compared to other substrates. The highest roughness value was measured on sample etched with nitric acid ($HNO_3$)+hydrochloric acid (HCl), whereas, the lowest value was recorded for the sample etched with hydrochloric acid. The roughness values for the etched surfaces were as follows: Glycergia ($HNO_3+HCl+C_3H_5(OH)_3$): ~50 μm; Nitric acid ($HNO_3$)+orthophosphoric acid ($H_3PO_4$): ~19 μm; Nitric acid ($HNO_3$)+hydrochloric acid (HCl): ~160 μm; Nitric acid ($HNO_3$)+glycerol ($C_3H_5(OH)_3$): ~20 μm; Nitric acid ($HNO_3$): ~35 μm; Hydrochloric acid (HCl): ~10μm; and Orthophosphoric acid ($H_3PO_4$): ~30 μm.

Figure 13:
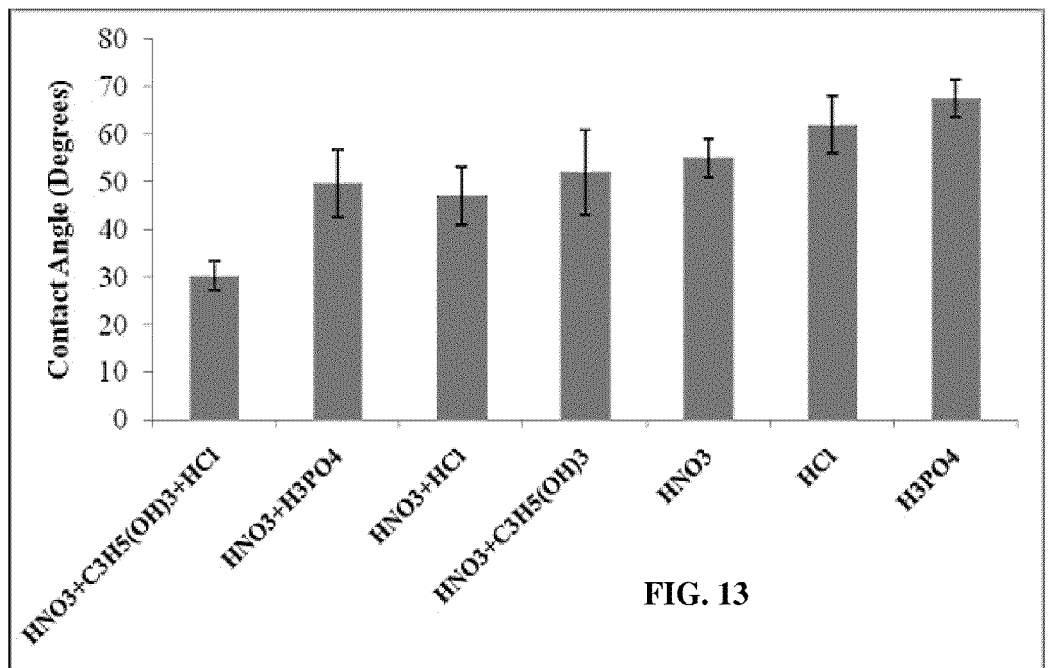
FIG. 13 is a graph of the contact angle measured on 316L SS CE surface 110 etched with different etching reagents (n=30,*p<0.01).

Water contact angles (VCA 2500 XE, Korea) may be used to evaluate the hydrophobicity or hydrophilicity of the chemically etched 316L SS surfaces. Analysis was carried out using VCA version 1.49 software. Water contact angle values for 316L SS samples etched with different etching reagents are presented in FIG. 13. Samples etched with Glycergia exhibited the lowest contact angle of 30.2±3.10, whereas the highest contact angle of 67.5±4.0° was observed on the substrate etched with Orthophosphoric acid ($H_3PO_4$). The contact angles for the other etched surfaces were as follows: Nitric acid ($HNO_3$)+orthophosphoric acid ($H_3PO_4$): ~49°; Nitric acid ($HNO_3$)+hydrochloric acid (HCl): ~46°; Nitric acid ($HNO_3$)+glycerol ($C_3H_5(OH)_3$): ~50°; Nitric acid ($HNO_3$): ~52°; and Hydrochloric acid (HCl): ~60°. The adhesion energy may be calculated from Equation (2) given below, where lowest contact angle of 30.2±3.1° includes an adhesion energy of 0.1341±0.0002 N/m and the highest contact angle of 67.5±4.0° includes an adhesion energy of 0.0995±0.0047 N/m. The CE surface 110 includes an adhesion energy between about 0.1343±0.0948 N/m.

Cell counting on Human aortic endothelial cells (HAECs) cultured on chemically etched samples was carried out using a stratified random sampling method. Numbers of attached cells were counted on 40 different fields using reflective light microscopy. For calculating the cell spreading area, representative images were captured with the use of a CCD camera coupled to a fluorescence/light microscope (Zeiss Axioplan 2 Imaging, Carl Zeiss Microimaging Inc., NY). Images were then analyzed using NIH Image J 1.62 software.

Figure 14:
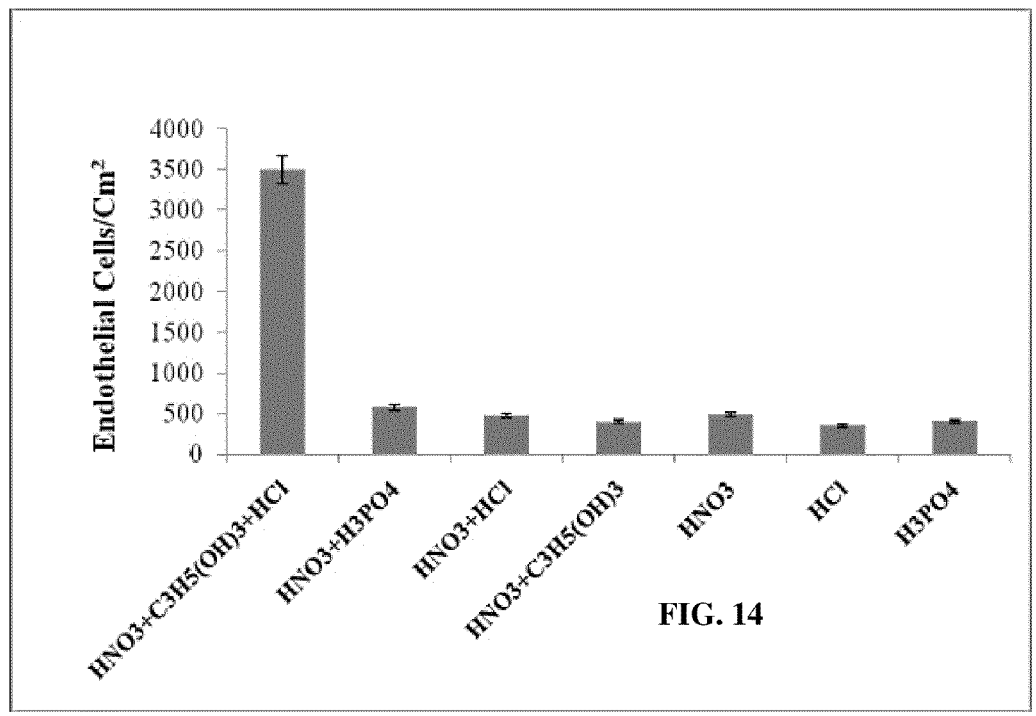
FIG. 14 is a graph of the density of human aortic endothelial cells on 316L SS CE surface 110 etched with different etching reagents (n=40,*p<0.001).
Figure 15:
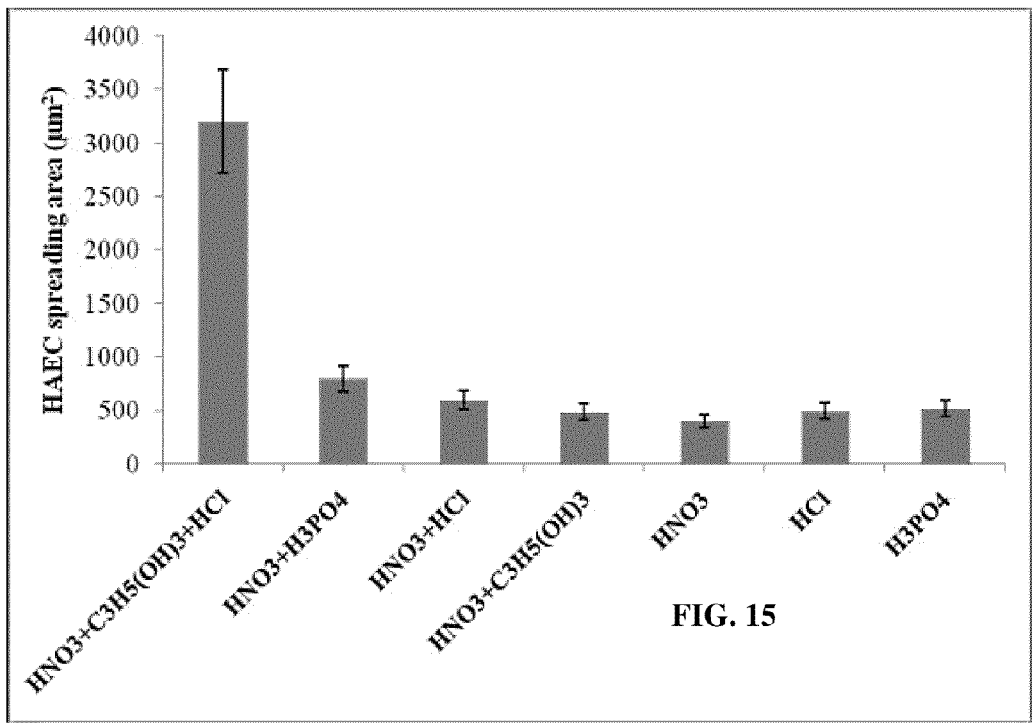
FIG. 15 is a graph of human aortic endothelial cell spreading area on 316L SS CE surface 110 etched with different etching reagents (n=40,*p<0.001).

Number of endothelial cells attached per cm of material substrate is shown in FIG. 14. The number of endothelial cells for the etched surfaces were as follows: Glycergia: ~3500/$cm^2$; Nitric acid ($HNO_3$)+orthophosphoric acid ($H_3PO_4$): ~510/$cm^2$; Nitric acid ($HNO_3$)+hydrochloric acid (HCl): ~500/$cm^2$; Nitric acid ($HNO_3$)+glycerol ($C_3H_5(OH)_3$): ~490/$cm^2$; Nitric acid ($HNO_3$): ~500/$cm^2$; Hydrochloric acid (HCl): ~460/$cm^2$; and Orthophosphoric acid ($H_3PO_4$): ~480/$cm^2$. Endothelial cell density on the sample etched with Glycergia ($HNO_3$+HCl+$C_3H_5(OH)_3$) was significantly higher ($p<0.001$) as compared to that on samples etched with other etching reagents, which suggest that the chemical etching of the 316L SS sample with Glycergia positively affected the endothelial attachment; whereas, specimens etched with other etching reagents were less favorable for endothelial cell attachment. HAEC spreading area (FIG. 15) for samples etched with different etchants. Significant difference ($p<0.001$) in cell spreading area was observed between the samples etched with Glycergia and other etching reagents. The HAEC spreading for the etched surfaces were as follows: Glycergia ($HNO_3$+HCl+$C_3H_5(OH)_3$): ~3200 µm ; Nitric acid ($HNO_3$)+orthophosphoric acid ($H_3PO_4$): ~760 µm ; Nitric acid ($HNO_3$)+hydrochloric acid (HCl): ~650 $µm^2$; Nitric acid ($HNO_3$)+glycerol ($C_3H_5(OH)_3$): ~500 $µm^2$; Nitric acid ($HNO_3$): ~480 µm ; Hydrochloric acid (HCl): ~500 $µm^2$; and Orthophosphoric acid ($H_3PO_4$): ~500 $µm^2$.

To identify activated focal adhesion sites samples were incubated for 1 hr at 37° C. in 200 µl of antibody solution (P-FAK-rabbit) diluted in PBS in the ratio 1:100. After 1 hr the samples were rinsed 3 times with PBS and 2 times with 5% BSA and dried. 200 µl of Fluorochrome (antirabbit Q DOT 655 goat) diluted (1:200) in PBS was added to the samples and incubated for 1 hr at 37° C. Finally, cells were rinsed 3 times with PBS and analyzed using fluorescence microscope and NIH Image J 1.62 software.

Figure 16:
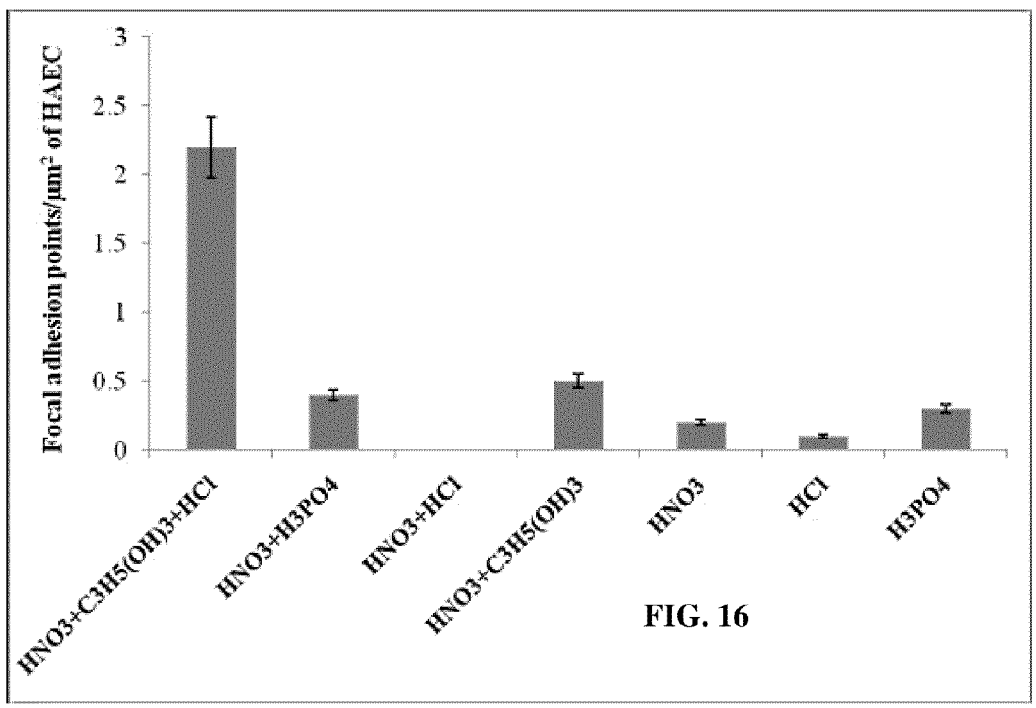
FIG. 16 is a graph of the number of activated focal adhesion contacts formed by human aortic endothelial cells on 316L SS CE surface 110 etched with different etching reagents (n=45,* p<0.001).

Number of activated focal adhesion contacts formed by endothelial cells on samples etched with different etching reagents are presented in FIG. 16. The number of Focal Adhesion Points/$µm^2$ for the etched surfaces were as follows: Glycergia ($HNO_3$+HCl+$C_3H_5(OH)_3$): ~2.25/$µm^2$; Nitric acid ($HNO_3$)+orthophosphoric acid ($H_3PO_4$): ~0.42/$µm^2$; Nitric acid ($HNO_3$)+hydrochloric acid (HCl): 0/$µm^2$; Nitric acid ($HNO_3$)+glycerol ($C_3H_5(OH)_3$): ~0.5/$µm^2$; Nitric acid ($HNO_3$): ~0.20/$µm^2$; Hydrochloric acid (HCl): ~0.10/$µm^2$; and Orthophosphoric acid ($H_3PO_4$): ~0.25/$µm^2$. Significantly higher ($p<0.001$) number of focal adhesion sites were counted on the 316L SS samples etched with Glycergia as compared to the specimens etched with other etchants. Cell morphology on etched samples is shown in FIGS. 17A-B. Bright fluorescence dots in the micrographs represent the focal adhesion contacts formed by the cell with the material substrate. Representative micrographs show that the endothelial cell spreading area is higher on samples etched with Glycergia and significantly less on substrates which were treated with other etchants. Endothelial cell monolayer formation due to cell-cell junctions and cell dividing on the surface was evident on surface etched with Glycergia, whereas, on other substrates rounded endothelial cell morphology was observed and there was no evidence of cell-cell interaction and endothelial cell growth with large uncovered areas and cracks in cell cytoskeleton was noted.

Different etchants for 316L SS surfaces were modified for increasing endothelialization. The selectivity of the etching process depends on the etching time and composition, which is important when finding best suited etching parameters. Selectivity of the etching process refers to the etchants ability to expose grain boundaries on the surface or create a contrast between grains and grain boundaries. When the selectivity of etching is high, deep and narrow crevices develop. When the selectivity is low, the bulk material removal is much higher, resulting in protrusions as observed in case of surfaces etched with other etching reagents. Optimum selectivity is preferred, which is dictated by time and concentration of the etching reagent and also the type of etching reagent used. A selectivity too high would etch the surface and expose deep grain boundaries, which will adversely affect endothelialization, as cells will not be able to form cell-cell contacts and this would decrease the rate of endothelialization. Although having deep grain boundaries may increase the amount of drug loaded on the surface. A selectivity too low would hamper the amount of drug loaded on the surface but may not affect endothelialization.

The geometric feature generated when etched Glycergia included HAEC attachment, spreading and number of focal adhesion contacts formed that were significantly higher on these substrates as compared to the 316L SS specimens etched with other etching reagents. Samples etched with Glycergia showed no evidence of pit formation or deep trenches (i.e. deep grain boundaries). FIG. 18 shows the SEM micrograph of an etched 316L SS substrate by Glycergia, where the geometric feature 10 includes a smooth grains surface 120 and dividing grain boundaries 140. Grain size was calculated using ASTM standard E112 and it was approximately 16 µm, where the approximate width and depth of the grain boundaries are 1 µm and 2 µm, respectively. The selectivity of the etching process is dominated by differences in molecular structures (higher degree of disorder at the grain boundaries) and probably differences in chemical composition. Etched surfaces reveal that, besides grain boundaries, in some cases also twin boundaries and dislocations were affected by the etching attacks.

When the etched surfaces are for stents, the slighter etched surfaces that reveal grain boundaries could be bridged easily by the endothelial cells, and the micro-depots formed might aid in drug loading. Micro-depots were formed when the surfaces were etched with nitric acid ($HNO_3$)+hydrochloric acid (HCl) and other strong etchants, which lead to the formation micro depots and deep furrows that could not be bridged by ECs.

Analysis of the surface morphology has shown that varying the conditions applied for grain-boundary etching of 316L SS stents can produce very different structures. In order to use the surface structure for enhancing endothelial cell attachment, there should be optimum depth and width of the grain boundaries and other microstructural features that can promote the formation of an endothelial cell monolayer. In the heart, a stent is loaded with an oscillating force due to the heart beat; consequently the stent must be fatigue resistant beside the optimal drug elution properties, but if the sharp edges are present in the surface morphology they might lead to early formation of crevices and fatigue failure as the edges act as notches. With the CE method, smooth surfaces are created so that the risk of progressing crevices might be minimized. For example, when using stronger $HNO_3$ etchings the structures were less uniform and the depot volume did not increase noticeably. The other side of the substrate is almost completely spared by the etch effect by having only small features. These small features could promote the proliferation of endothelial cells without the risk of damaging the balloon catheter. Etching with other etchants seems to form morphologies that are not optimally suited for the situation described above; whereas, etching with Glycergia yields better results due to smooth grains and surfaces free of any pits/protrusions.

EXAMPLE III

Grain Size of the CE Surface for Endothelial Attachment

In another embodiment, the geometric feature 12 comprises the CE surface 110 including a smooth grain surface 120. The smooth grain surface 120 includes a grain size 122, a plurality of grain boundaries 140 (GB) surrounding the grain feature, as shown in FIG. 20C. The grain boundary 140 is the dividing surface between two adjacent grain crystals having a different crystallographic orientation. The grain feature 120 and the grain boundaries 140 are three dimensional. The grain boundary includes an abrupt orientation change, occurring over only one or two atomic planes. Because of this, the grain boundary includes atoms that are displaced out of their lattice positions to positions of a lowest energy due to a lattice misfit where the crystals meet. Hence, an increased energy above the normal lattice energy is associated with the displaced atoms at the grain boundary, giving rise to a localized grain boundary energy. When the misorientation between the neighboring crystals is small, the displacement of atoms in the boundary from their normal lattice positions is also small, and hence the increase in energy of the boundary above the lattice energy is correspondingly small. The grain boundary energy increases with increasing misorientation between the grains up to a maximum value at relative misorientation of about 10° to 30°.

Figure 20D:
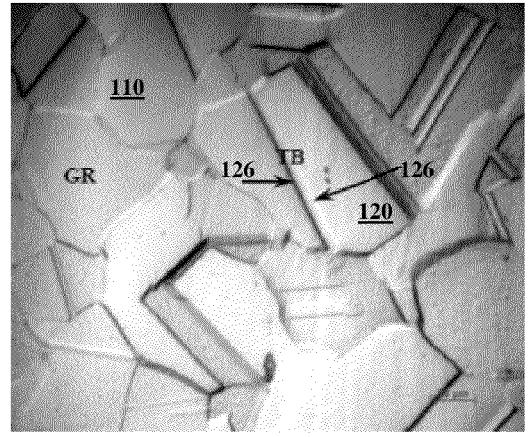

Alternatively, the grain feature may include twin boundaries 126, as shown in FIG. 20D. Twin boundaries 126 separate a pair of twin grain features. A twin grain feature is when the arrangement of atoms in one of the grain feature can be generated from the other by reflection across a common plane. The crystal structure of the two grains 120 is identical and is in different orientations in space. Because twins 126 have such a special orientation relationship, the boundaries separating the twins have a very low energy per unit area; hence they do not contribute significantly towards the surface free energy.

The grain feature may include a variety of random shapes including, but not limited to, trilateral, quadrilateral, polygonal, pentagonal, hexagonal, heptagonal, octagonal, circular, or any combination thereof Alternatively, the grain feature 120 includes a twin boundary 126 (TB), as shown in FIG. 20D.

Varying the grain sizes of 316L SS affects the attachment and spreading of human aortic endothelial cells (HAECs).

FIGS. 20A-D show the different sizes of the grains on the CE surface 110. The grain size may include a width of from about 10 μm to 70μm (ASTM 9.0-4.9). Nanoscale and sub nanoscale grain size may be used to promote endothelialization where endothelial cells do not respond to micron or sub micro scale features. The specimens may be sectioned from sheets/wires/tubes and the grain structure may be revealed by polishing and etching with Glycergia. Contact angle measurement was done to assess the hydrophilicity and hydrophobicity of the substrates. AFM and XPS were used to characterize the roughness and surface chemistry of the specimens. Cells were seeded on mechanically polished and chemically etched specimens followed by identification of activated focal adhesion sites using fluorescently tagged anti-pFAK. The 16 μm grain size etched specimen had significantly ($p<0.01$) higher number of cells attached per $cm^2$ than other specimens, which may be attributed to the greater grain boundary area and associated higher surface free energy. The underlying material feature influences the HAEC behavior and has important implications in endothelialization.

Mechanical polishing of samples may be performed following ASTM E3-95 standard for preparation of metallographic specimens. Fine grinding may be performed on the grinder using a continuous water flow for lubrication. Final polishing may be done using METADI II Diamond compound (Buehler, Lake Bluff, Ill.) and a nylon polishing cloth (Buehler, Lake Bluff, Ill.) on the Buehler grinder/polisher. METADI II diamond abrasive (9 μm and 0.1 μm) may be distributed uniformly over the polishing cloth using the applicator syringes.

Different etching reagents were explored including 1 ml $HCl+1$ ml $HNO_3$, which lead to formation of pits and uneven surface architecture. But the mechanically polished samples were successfully etched using glycergia (3 ml glycerol $(C_3H_5(OH)_3)+1$ ml $HCl+1$ ml $HNO_3$). The details of the optimal etching process for better endothelial cell attachment, where previously discussed above. A small pool of etchant was created on the sample surface and the samples were cleaned after approximately 30 seconds in double distilled water. The grain size of the chemically etched samples was measured using ASTM (American Society for Testing of Materials) E112 standard. Equation (1) was used to calculate the grain size:

$$n=2^{G-1}; \qquad (1)$$

where n=the number of grains per square inch at 100×magnification, and G=the ASTM grain size number.

Figure 19:
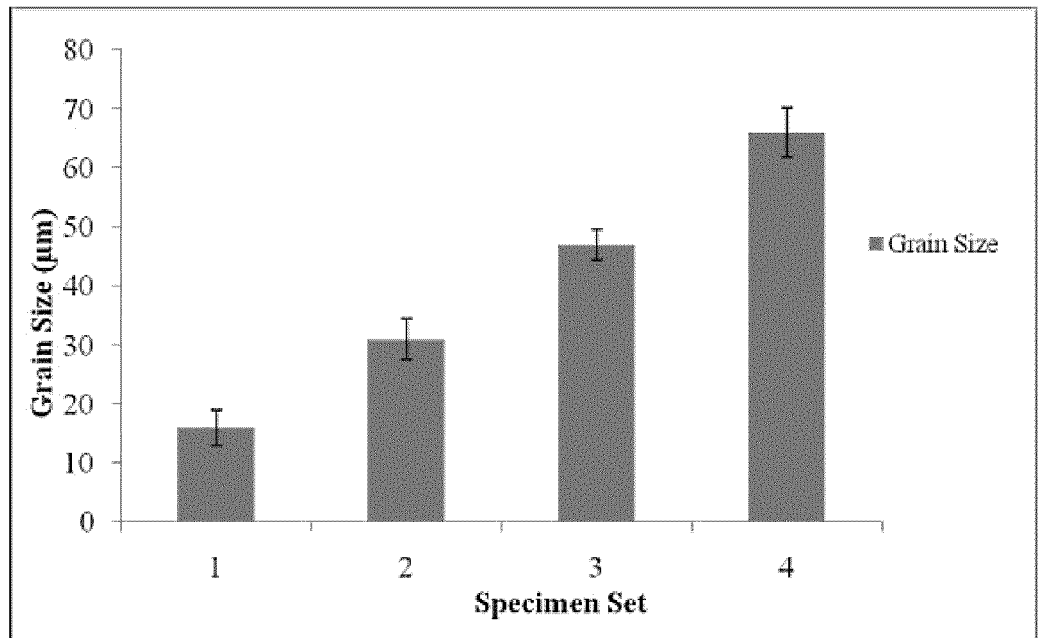
FIG. 19 is a bar graph showing the grain size values in micrometer (μm) on four different set of specimens (n=15, p<0.001).

FIG. 19 shows the result of grain size calculation using ASTM standard E112. One way ANOVA and Student's t test were performed to determine the statistical significance between these sets of samples. All the grain sizes (16±3, 31±4, 47±3, 66±4 μm) estimated from four different Specimen Sets 1-4 were statistically different from each other ($p<0.001$) and the actual size was not different from the nominal size. FIGS. 20A-D are optical micrographs of CE surface 110 of 316L SS samples of 16 μm, 31 μm, 47 μm and 66 μm grain sizes, respectively. The chemical etching of the samples with glycergia (3 ml glycerol $(C_3H_5(OH)_3)+1$ ml $HCl+1$ ml $HNO_3$) resulted in the formation of grain boundary 140 (indicated by GB arrows in FIG. 20C) around the grain 120 (indicated by GR in FIG. 20C), and the orientation of the GB was dependent surface morphology. The surface topography that forms after the chemical etching of the samples is highly dependent on the material feature with protruding grains having a lower dissolution rate as compared to the grain boundaries 140. FIG. 20D shows twin boundaries 126, indicated by TB arrows.

Water contact angles (VCA 2500 XE, Korea) may be used to evaluate the hydrophobicity or hydrophilicity of the mechanically polished and chemically etched 316L SS surfaces. The water contact angle of the samples was measured using the sessile drop method. A video camera is attached to a computer, enabling the image of the drop and the samples to be viewed on the computer screen and the angle the water droplet makes to the surface was measured. Analysis was carried out using VCA version 1.49 software. At equilibrium the contact angle can be used to determine the interfacial energy. According to the Young-Dupre' equation (2):

$$\gamma(1+\cos\theta) = \Delta W_{SL} \quad (2)$$

where $\gamma$=liquid-vapor surface tension; $\theta$=contact angle; $\Delta W_{SL}$=adhesion energy per unit area of the solid and liquid surfaces. $\gamma$ for water-air is 0.07197 N/m at 25° C. Using Equation (2), the adhesion energy may be calculated.

Figure 21A:
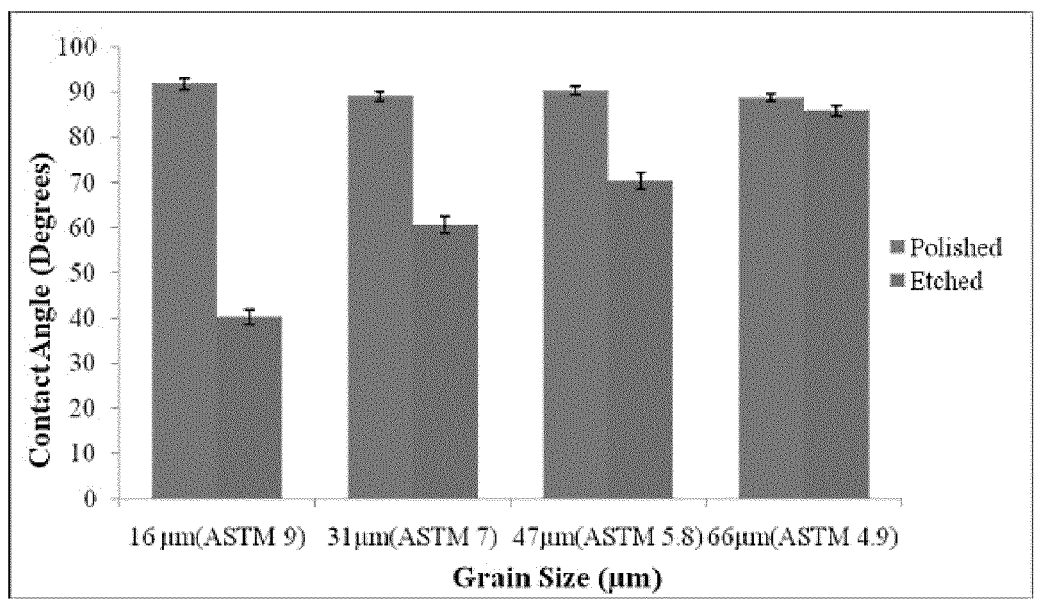
FIG. 21A is a graph of the contact angle in degrees on mechanically polished and chemically etched 316L SS substrates of varying grain sizes (n=20,*p<0.01)
Figure 21B:
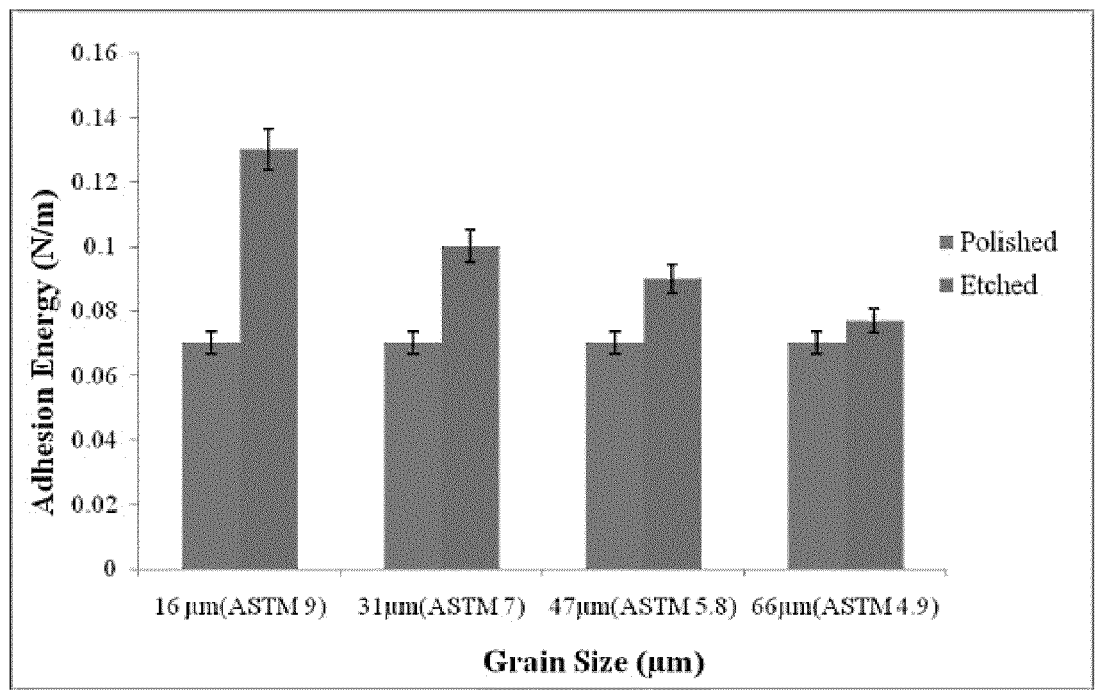
FIG. 21B is a graph of the adhesion energy (N/m) of mechanically polished and CE surface 110 substrates of varying grain sizes (n=20,*p<0.01).

FIGS. 21A-B show the contact angle and adhesion energy, respectively, measured on mechanically polished and CE surface 110 samples. No statistically significant difference in contact angle was observed on mechanically polished samples of different grain sizes. In contrast, CE surfaces of 16 μm grain size samples exhibited the lowest contact angle of 40.215±1.66° (highest adhesion energy of 0.1269±0.0013 N/m, i.e. between about 0.1256-0.1283 N/m) whereas the highest contact angle of 85.99±1.14° (lowest adhesion energy of 0.0770±0.0015N/m, i.e. between about 0.0755-0.0784N/m) was observed on 66 μm grain size substrate.

Figure 22A:
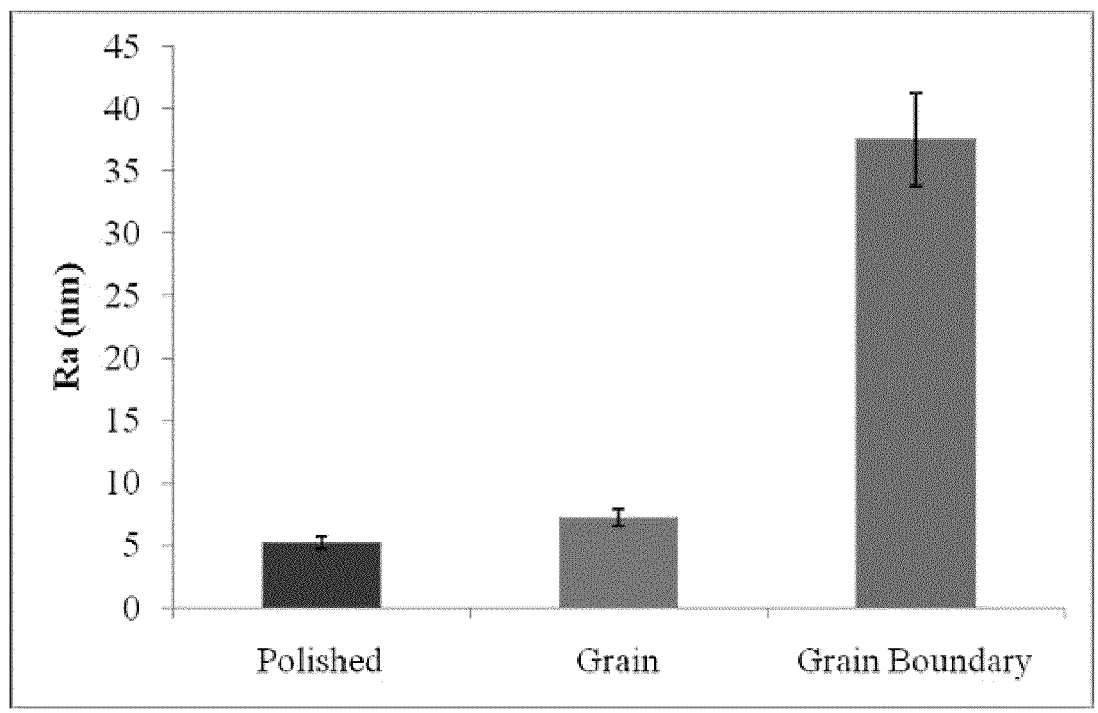
FIG. 22A is a graph of the average roughness value (Ra) measured on mechanically polished samples and CE surface 110 (grain/grain boundaries) samples of all grain sizes using atomic force microscope (n=40,*p<0.001)
Figure 22B:
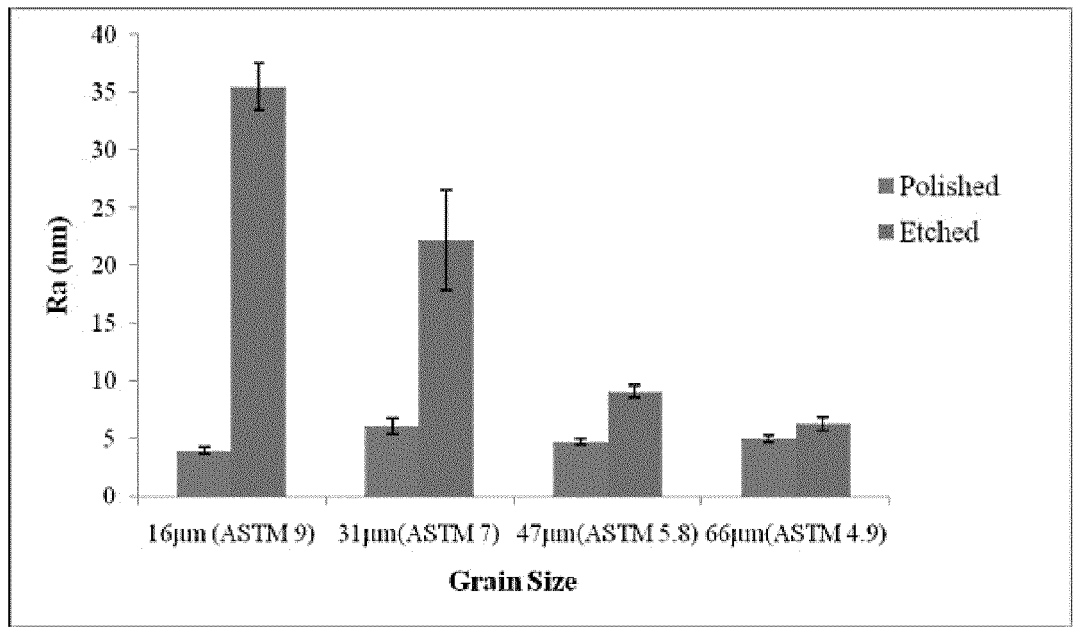
FIG. 22B is a graph of the average roughness value (Ra) measured on mechanically polished and CE surface 110 samples of varying grain sizes using atomic force microscope (n=10, *p<0.01).

The surface roughness of the mechanically polished and chemically etched 316L SS samples was performed as previously indicated. Average/mean roughness (Ra) values for mechanically polished and CE surface 110 samples were measured by atomic force microscopy (AFM). FIG. 22A shows a comparison of roughness values for mechanically polished sample and CE surface 110 sample averaged over all grain sizes. Since the CE surface 110 samples showed different microstructural features, the roughness values may be estimated separately on grains and grain boundaries. Roughness values measured on mechanically polished sample was approximately 5±0.4 nm and on CE surface 110 samples were approximately: 35.5±2.0 nm (16 μm, ASTM 9); 22.1±4.33 nm (31 μm, ASTM 7); 9.11±0.544 nm (47 μm, ASTM 5.8); and 6.28±0.56 nm (66 μm, ASTM 4.9), as shown in FIG. 12B. The average roughness (Ra) of CE surface 110 samples of 16 μm, 31 μm and 47 μm was significantly higher (p<0.01) as compared to their corresponding mechanically polished samples. The roughness values increased after chemically etching of the sample surface.

X-ray photoelectron spectroscopy (XPS) may be used to analyze the surface chemical composition of mechanically polished and CE surface 110 chemically etched 316L SS surfaces. XPS measurements were carried out using a Kratos Axis Ultra spectrometer (Kratos Analytical Inc., GB). A monochromatised X-ray source equipped with an aluminum anode (Al K$\alpha$=1456.6 eV) operating at 210 W (15 kV, 14 mA) and approximately $3\times10^{-7}$ Pa was used. The atomic percentages of the elements present on the analyzed surfaces were calculated using the CasaXPS (version 2.2.68) software and the atomic sensitivity factors included in it.

X-ray photoelectron spectroscopy (XPS) evaluated the surface chemistry of mechanically polished and CE surface 110 samples, as shown in Table 1. Hydrogen is undetectable in XPS and the presence of carbon might be related to surface contamination, which occurs due to the fact that the samples are exposed to air before the XPS measurement, hence, the quantification for these two elements is not shown in the results. The higher Ni concentration in the surface layer is exhibited by mechanically polished samples as compared to CE surface 110 samples. The presence of Ni 2 p peaks and their corresponding binding energies indicate that in all the samples, nickel is present in the elemental form. Atomic concentration of iron was higher on polished samples as compared to CE surface 110 samples. The peaks and their corresponding binding energies indicate the presence of iron in elemental and oxide form in polished samples; whereas, in CE surface 110 samples, iron is predominantly present as oxide. In polished samples chromium was mostly present as oxide with traces of chromium in elemental form on the surface. In CE surface 110 samples, very strong peaks for chromium oxide were observed as compared to elemental chromium peaks that were very weak.

TABLE 1

Surface chemical composition (at. %) measured using XPS on mechanically polished and CE surface 110 on 316L SS substrates (n = 20).

| | Ni (%) | Fe (%) | Cr (%) | O (%) | N (%) | Mo (%) | Cl (%) |
|---|---|---|---|---|---|---|---|
| Polished | 0.9 ± 0.3 | 17.1 ± 3.0 | 13.0 ± 1.5 | 64.4 ± 3.5 | 1.5 ± 0.1 | 2.2 ± 1.2 | 0.7 ± 0.3 |
| Etched | 0.7 ± 0.2 | 14.0 ± 4.2 | 16.0 ± 1.6 | 60.9 ± 3.6 | 1.9 ± 0.2 | 3.9 ± 1.1 | 2.4 ± 1.2 |

Atomic concentration of oxygen was higher on polished samples as compared to CE surface 110 specimens. Presence of metallic oxides with some traces of hydroxides was observed on polished samples. Equally strong peaks for metallic oxides and hydroxides were observed on CE surface 110 samples. Peaks and their corresponding binding energies in polished samples indicate the presence of nitrogen as $NH_3$ or as part of an organic matrix. CE surface 110 samples indicate the presence of nitrogen predominantly as nitrides and traces of nitrogen in organic matrix and as nitrates. Higher atomic concentration of molybdenum was observed on CE surface 110 samples as compared to polished specimens. CE surface 110 samples exhibited peaks that indicated the presence on molybdenum in the elemental and oxidized forms. In polished samples molybdenum was present in elemental form only.

Human aortic endothelial cells (HAECs) cell counting was carried out as previously indicated, using a stratified random sampling method. Numbers of attached cells were counted on 60 different fields using reflective light microscopy. For calculating the cell spreading area, representative images were captured with the use of a CCD camera coupled to a fluorescence/light microscope (Zeiss Axioplan 2 Imaging). Images were then analyzed using NIH Image J 1.62.

Number of activated focal adhesion contacts formed by the cells after 8 hrs on mechanically polished and CE surface 110 samples of varying grain sizes were estimated using NIH Image J 1.62 (National Institute of Health, MD). To prepare the cells for evaluation of the number of focal adhesion points, cells were rinsed with PBS and fixed with 4% formaldehyde in PBS followed by rinsing again in PBS. Fixed cells were permeabilized with 0.2% Triton x-100 in PBS for 6 minutes followed by rinsing briefly 3 times with PBS and 2 times with 5% BSA in PBS. To identify active (phosphorylated) focal adhesion sites samples were incubated for 1 hr at 37° C. in 200 µl of antibody solution (P-FAK-rabbit) diluted in PBS in the ratio 1:100. After 1 hr the samples were rinsed 3 times with PBS and 2 times with 5% BSA and dried. 200 µl of Fluorochrome (antirabbit Q DOT 655 goat) diluted (1:200) in PBS was added to the samples and incubated for 1 hr at 37° C. Finally, cells were rinsed 3 times with PBS and analyzed using fluorescence microscope and NIH Image J 1.62.

Figure 23A:
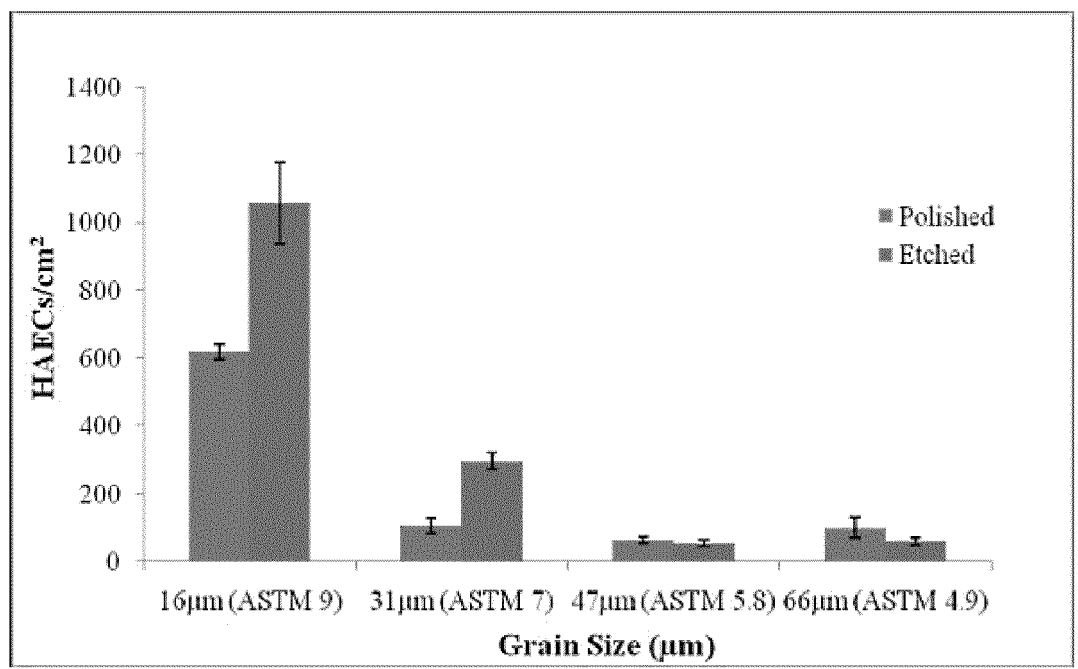
FIG. 23A is a bar graph showing the density (cells/$cm^2$) of endothelial cells attached to mechanically polished and chemically etched 316L SS substrates of different grain sizes (n=20,* p<0.01)

Human aortic endothelial cells were seeded on polished and CE surface 110 samples of varying grain sizes (16 µm, 31 µm, 47 µm, 66 µm). The density of cells in the culture media was 2000 cells/ml and each sample was incubated in 4 ml of cell suspension. Number of endothelial cells attached per $cm^2$ of material substrate is shown in FIG. 23A. The CE surface 110 samples included the following results: 16 µm: 1050 HAEC's/$cm^2$; 31 µm: 300 HAEC's/$cm^2$; 47 µm: 52 HAEC's/$cm^2$; and 66 µm: 50 HAEC's/$cm^2$. One way ANOVA and student's t test were performed to determine the statistical significance of the data. No statistically significant difference in cell density was observed between mechanically polished and CE surface 110 samples of 47 µm and 66 µm grain sizes, whereas samples of 16 µm and 31 µm grain sizes showed statistically significant ($p<0.01$) difference in number of cells attached on polished and CE surface 110 substrates. Cell density on 16 µm CE surface 110 samples was significantly higher ($p<0.01$) as compared to that on mechanically polished/CE surface 110 samples of 31 µm, 47 µm and 66 µm grain sizes. Hence, the 16 µm chemically etched samples positively affected the endothelial attachment; whereas, mechanically polished and chemically etched samples of 31 µm, 47 µm and 66 µm grain sizes were less favorable for endothelial cell attachment.

Figure 23B:
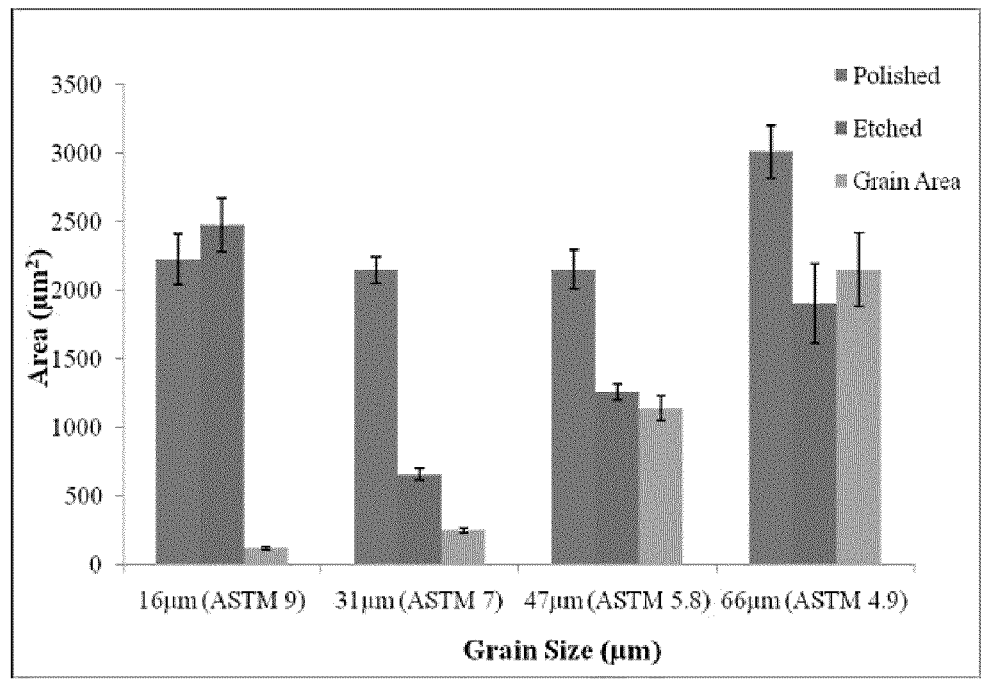
FIG. 23B is a bar graph showing the comparison of grain area (μm2) and endothelial cell spreading area ($\mu m^2$) on mechanically polished and 316L SS CE surface 110 substrates of different grain sizes (n=10).

Endothelial cell spreading area (FIG. 23B) was estimated using NIH Image J 1.62 software for mechanically polished and CE surface 110 samples of different grain sizes (16µm, 31 µm, 47 µm, 66 µm). The CE surface 110 samples included the following: 16 µm: 2490 area of $\mu m^2$; 31 µm: 690 area of $\mu m^2$; 47 µm: 1250 area of $\mu m^2$; and 66 µm: 1800 area of $\mu m^2$. The grain area samples including the following: 16 µm: 150 area of $m^2$; 31 µm: 200 area of $\mu m^2$; 47 µm: 1200 area of $\mu m^2$; and 66 µm: 2000 area of $\mu m^2$. Statistically significant difference in cell spreading area between mechanically polished and CE surface 110 samples was observed for 31 µm ($p<0.001$), 47 µm ($p<0.01$) and 66 µm ($p<0.01$) grain size samples; whereas, no significant difference was noted for 16 µm grain size specimen. The endothelial cell spreading area on CE surface 110 specimens of 31, 47, and 66 µm grain sizes is less as compared to their corresponding mechanically polished samples, but cell spreading on 16 µm CE surface 110 specimen matches up with that of its corresponding polished specimen. FIG. 23B also compares the grain area of CE surface 110 for 316L SS material feature of varying grain sizes with the endothelial cell spreading area. Cell spreading area and grain area are comparable for CE surface 110 of 47 µm and 66 µm grain size samples, whereas, for 16 µm ($p<0.001$) and 31 µm ($p<0.01$) grain size samples the difference in significant. Grain area refers to the entire area of the grain, for example, area of the circle calculated using the formula $\pi r^2$, and calculated using computer software. Grain area and grain size are different parameters calculated using different standard methods.

Figure 24A:
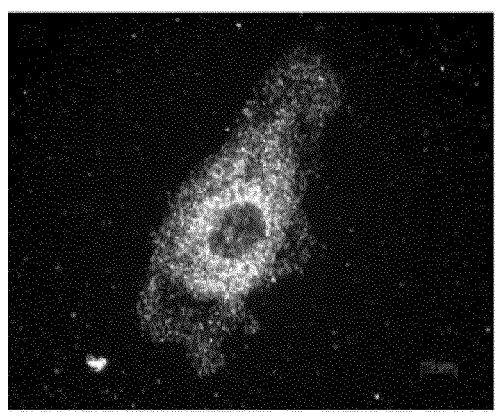
FIGS. 24A-D are fluorescent images of the morphology of human aortic endothelial cells on (FIG. 24A) 16 μm, (FIG. 24B) 31 μm, (FIG. 24B) 47 μm, (FIG. 24D) 66 μm are 316L SS CE surface 110 substrates (mag: 630×, bar: 10 μm), where the bright dots on the cells indicate activated focal adhesion contacts.
Figure 24B:
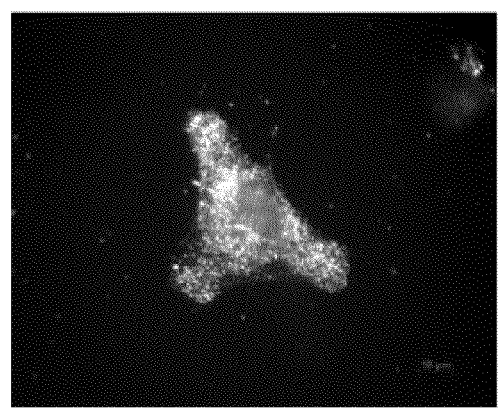
Figure 24C:
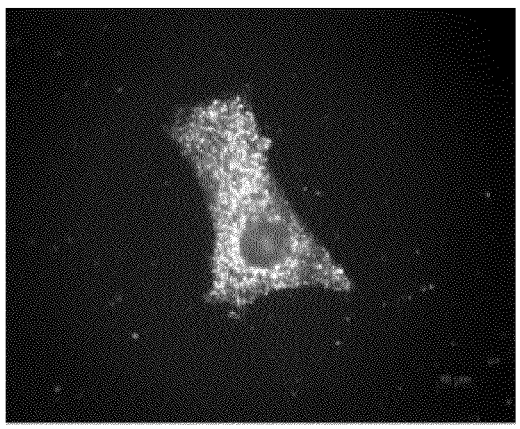
Figure 24D:
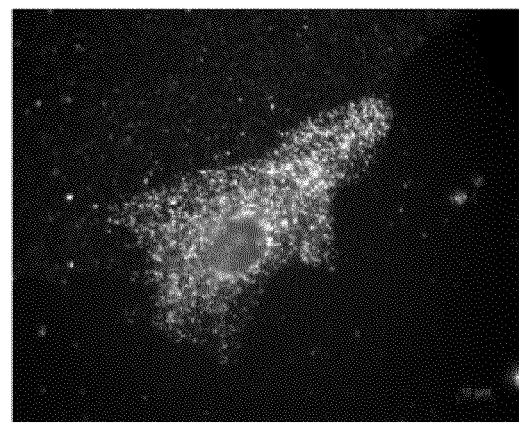
Figure 25A:
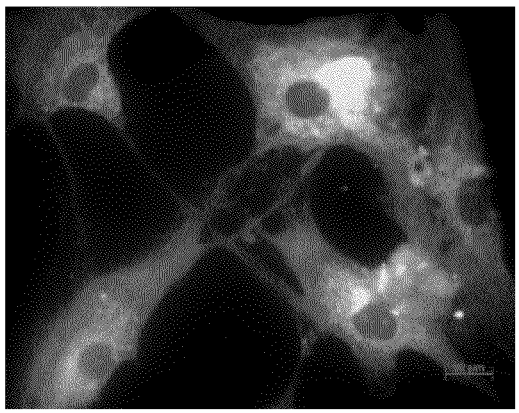
FIGS. 25A-B are fluorescence micrographs showing morphology of the endothelial cells attached to 316L SS CE surface 110 substrates of 16 μm (FIG. 15A) and 66 μm (FIG. 15B) grain sizes after 8 hrs of cell culture.
Figure 25B:
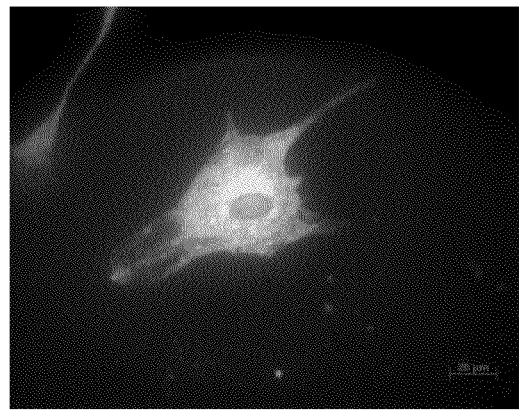

Endothelial cell morphology on polished and CE surface 110 samples of different grain sizes is shown in FIGS. 24A-D. Bright fluorescence dots in the micrographs represent the focal adhesion contacts formed by the cell with the material substrate. Representative micrographs show that the endothelial cell spreading area on CE surface 110 samples of 31 µm (FIG. 24B), 47 µm (FIG. 24C), and 66 µm (FIG. 24D). On 16 µm grain size polished/CE surface 110 samples the endothelial cell spreading area is shown in FIG. 24A. The focal adhesion contacts are more concentrated near the nucleus than the periphery of the cell in the chemically etched sample (FIG. 24A. The nucleus-concentrated focal adhesion points favorably affect endothelial cell migration on CE surface 110 samples. Random endothelial cell shapes were observed on both specimen types of all grain sizes, which can be attributed to random shapes of grains in the inherent material feature. FIGS. 25A-B compares the morphology of endothelial cells on CE surface 110 for 16 µm and 66 µm grain size samples at lower magnification. 16 µm CE surface 110 samples showed evidence of higher cell spreading area, formation of cell-cell junctions and cell dividing on the surface (FIG. 25A); whereas, on 66 µm grain size samples rounded endothelial cell morphology was observed and there was no evidence of cell-cell interaction or extracellular matrix formation (FIGS. 25B). Cell density on 16 µm CE surface 110 samples was higher as compared to 66 µm grain size samples (FIG. 23A). Overall, endothelial cells on 16 µm CE surface 110 surfaces appeared to have spread on the grains and bridged across the grain boundaries and a homogenous covering of cells without any special orientation was also noted. In contrast, on other sample types, irregular endothelial cell growth with large uncovered areas and cracks in cell cytoskeleton was observed. No evidence of foreign body giant cells (FBGCs) was observed on the samples, but relatively more fields on mechanically polished and 66 µm grain size CE surface 110 samples showed signs of dead endothelial cells/debris.

Figure 26:
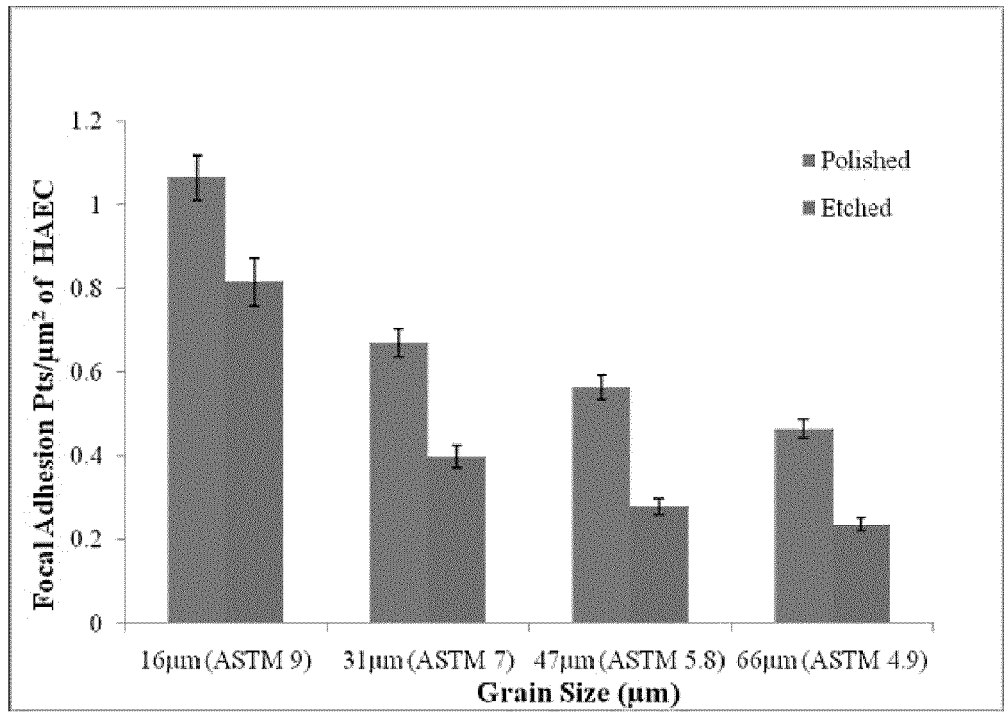
FIG. 26 is a bar graph showing the number of activated focal adhesion sites per $\mu m^2$ of endothelial cell on mechanically polished and 316L SS CE surface 110 substrates of different grain sizes (n=20, p<0.01).

Focal adhesion kinase (FAK) is a non-receptor tyrosine kinase that plays an important role in normal cellular processes such as adhesion, spreading, migration, proliferation and survival. In cultured cells it is localized to focal adhesion contacts and becomes phosphorylated and activated in response to integrin-mediated binding of cells to the extra-cellular matrix, suggesting an important role in cell adhesion and/or migration. FIG. 26 shows the number of activated focal adhesion contacts formed by endothelial cells on polished and CE surface 110 samples of varying grain sizes. The CE surface 110 samples included the following: 16 µm: approximately 0.80 focal adhesion points/$\mu m^2$ of HAEC; 31 µm: approximately 0.39 focal adhesion points/$\mu m^2$ of HAEC; 47 µm: approximately 0.27 focal adhesion points/µm of HAEC; and 66 µm: approximately 0.22 focal adhesion points/µm of HAEC. Statistically significant difference was observed between polished and CE surface 110 sample groups of all grain sizes ($p<0.01$). Maximum number of focal adhesion contacts was observed for 16 µm and minimum for 66 µm grain size CE surface 110 samples. Similar trend of decrease in number of focal adhesion contacts from 16 µm to 66 µm was observed for CE surface 110 samples.

16 µm CE surface 110 sample showed significantly higher endothelial cell density and spreading area as compared to CE surface 110 samples of other grain sizes. Number of focal adhesion sites was also higher on 16 µm grain size 316L SS CE surface 110 as compared to 31 µm, 47 µm and 66 µm CE surface 110 samples.

The characteristics and composition of 316L SS cause HAECs to respond differently to CE surface 110 samples of different grain sizes. 316L stainless steel (ASTM F138, F139) may be used as cardiovascular implant material. The "L" in the designation denotes low carbon content (<0.03 wt. %), which reduces the possibility of in-vivo corrosion. The 316L SS alloy is predominantly iron (60-65 wt. %) alloyed to major amounts of chromium (17-19 wt. %) and nickel (12-14 wt. %), plus minor amounts of nitrogen, manganese, molybdenum, phosphorous, silicon and sulfur. Since 316L SS has a lower % of carbon (<0.03 wt %), the possibility of carbide precipitation at the grain boundaries or chromium depletion from the adjacent regions is significantly reduced. 316L SS is covered with a strongly adherent oxide layer that consists mostly of $Cr_2O_3$ oxide. This oxide layer is partially removed in the process of chemically etching and grains and grain boundaries 140 that differ in chemical composition or charge concentration are exposed on the CE surface 110.

316L SS feature is of a single phase austenite (FCC) grains of grain size ASTM 6 or finer, separated by grain boundaries and free from ferritic (BCC) or carbide phases and inclusions such as sulfide stringers. When examined under a microscope after chemical etching grain boundaries in a polycrystalline material like 316L SS, the grain boundaries 140 show up as lines and different constituents reflect the light in different ways, as shown in FIGS. 20A-D. FIGS. 20A-D exhibited a single phase austenitic (γ) structure with annealing twin boundaries 26 (indicated by arrows in FIG. 20D).

FIGS. 21A-B represent the contact angle and adhesion energy measurement on mechanically polished and chemically etched 316L SS CE surface 110 samples of different grain sizes. Such large differences in contact angles are not likely due to surface roughness differences between these samples, where the surface chemistry or surface charge may cause such effects. The presence or absence of the grain boundary 140 has an effect on contact angle and subsequent adhesion energy measured on CE surface 110 substrates. As the grain size 122 decreases, the relative area occupied by the grain boundary 140 increases, and the surface free energy increases and the contact angle decreases. A comparison was made between the contact angle values measured on mechanically polished and CE surface 110 samples, as shown in FIG. 21A. Mechanically polished samples showed significantly higher contact angle and greater hydrophobicity as compared to CE surface 110 samples (p<0.01). The low contact angle, higher adhesion energy measured on 16 μm grain size 316L SS CE surface 110 sample in contrast to chemically etched and mechanically polished samples of other grain sizes are attributed to more grain boundary area and associated higher surface energy. A smooth mechanically polished surface with relatively thick amorphous and polycrystalline oxide suppresses the microstructural features of the material and hence exhibits lower adhesion energy.

A 15 μm groove size 316L SS specimen may exhibit the maximum number of endothelial cells per $mm^2$. The typical size of endothelial cells is 10-20 μm, which is comparable to 16 μm grain size in the chemically etched sample surface. As discussed above, small grain size sample has more adhesion energy (low contact angle) and greater roughness as compared to higher grain size specimens. Hence, more interaction of the endothelial cell with the grain boundary on 16 μm grain size CE surface 110 samples explains the increased endothelial cell density and cell spreading on these samples. The 16 μm grain size CE surface 110 specimen has a significant impact on initial attachment phase of endothelial cells and subsequent spreading. Endothelial cell behavior on mechanically polished samples and CE surface 110 samples indicate that initially cells adhered to the surfaces and their distribution was regular, but once the cells entered the active adhesion phase they were probing for intercellular and surface contacts. Cells that see limited or no adhesion zones, as in case of CE surface 110 and mechanically polished samples of larger grain sizes, can hardly extend anymore to less adhesive sur-rounding and enter in apoptosis and release apoptosis signal to the surrounding cells. On 16 μm grain size CE surface 110 specimens, cells with good focal adhesion complexes have grown uniformly over the surface and cells are in proliferation phase with some cells migrating towards uncovered surface. The grain boundary 140 is acting as a stimulus for cell adhesion and spreading on CE surface 110 samples. FIG. 22A shows that in CE surface 110 samples, the presence of grain boundaries 140 causes the increase in roughness values, which is due to the chemistry or surface charge difference between the grains and grain boundary, or simply due to the topography. The presence of more grain boundary area in the 16 μm and 31 μm CE surface 110 samples is the cause of large increase in roughness value, because lower roughness values were measured on 66 μm grain size samples, which have comparatively less grain boundary area.

Nickel is present in elemental form in polished and etched specimens, the % difference between mechanically polished and CE surface 110 sample is of 0.2%. The toxic effects of nickel have been linked to increased levels of oxidative stress found within endothelial cells exposed to nickel ions. The permeability of the endothelium increases and its barrier function impaired by generation of intracellular oxygen radicals e.g. OH. Surface nickel species therefore influence the biocompatibility of the alloy. The predominant effect of nickel on the endothelial cells is on the expression of VE-cadherin and F-actin within endothelial cells grown to confluence following the 72 hours of culture on NiTi alloy. In contrast, the maximum % of chromium as oxide might enhance the HAEC attachment and spreading on the surface of CE surface 110 samples, but the surface of mechanically polished and CE surface 110 samples consisted of trace amounts of other elements and predominantly chromium oxide of varying thickness, which may have affected the probability of interaction of endothelial cells with material feature. A more detailed analysis of any difference in chemistry of grains and grain boundary may be accomplished, which is discussed below.

EXAMPLE IV

Human Blood Plasma Protein Adsorption on the CE Surface

Interaction of human blood plasma proteins with the vascular biomaterial surfaces is the initial step in the chain of events leading to tissue incorporation of endovascular devices. The adsorption of plasma proteins: albumin, fibronectin, vitronectin and fibrinogen onto four distinctive 316L, stainless steel CE surfaces 110, Specifically, protein adherence to as-received (AR) mechanically polished (MP) electrochemically polished (EP) and CE surface 110 (CE) 316L stainless steel (SS) substrates was examined. These surfaces were characterized using AFM and ToF SIMS. Adsorbed plasma protein distribution was detected using primary and secondary antibodies. Quantitative assessment was carried out by measuring the adsorption of radiolabeled ($^{125}I$) plasma proteins on the surfaces Albumin, fibronectin and vitronectin were observed to adsorb preferentially at the grain boundaries on chemically etched samples. Quantitative analysis revealed significantly higher total amounts of albumin, fibronectin and vitronectin adsorption on CE surface 110 specimens as compared to other sample types. Fibrinogen adsorption was lowest on CE surface 110 samples relative to other surfaces. AFM measurements performed in a low saline aqueous medium at physiological pH and ToF SIMS measurements revealed a relatively high positive charge distribution at the grain boundaries on CE surface 110 specimens. The CE surfaces 110 grain boundaries 140 include an increased binding and concentration of albumin, fibronectin and vitronectin, which is related to the presence of positive charges at the grain boundaries 140 and the highly negatively charged plasma protein adsorption on these CE surfaces 110 with the exception of fibrinogen.

Samples were sectioned into 1 $cm^2$ pieces and cleaned with Extran™ detergent and acetone in an ultrasonic cleaner at 60° C. in two different steps of 10 min and finally rinsed in double distilled water for 5 min. Mechanical polishing, electrochemical polishing and chemical etching of the mechanically polished samples with Glycergia was done, as indicated previously. Electrochemical polishing of mechanically polished samples was done in a 50 ml tube which was dipped in a bath kept at 70±5° C. temperature. A DC in voltage regulated mode was used for power supply. As received 316L SS strips (2.5 inches×0.5 inches) were connected to the anodic terminal and graphite was used as a cathode. Both anodic and cathodic terminals were submerged in an electrolyte ($H_3PO_4$ and $H_2SO_4$ in the ratio of 3:2), forming a complete electrical circuit. Electrochemical polishing was done at 3.5±0.1 volts and 1.6±0.2 amperes current for 5 min. Mechanically polished samples were etched with glycergia, as indicated previously.

Figure 27:
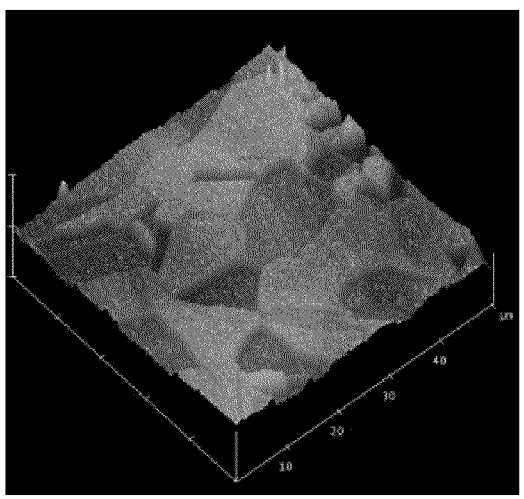
FIG. 27 is an AFM surface topography image of CE surface 110 (CE) 316L stainless steel substrates.

The AFM surface topography image of an as-received 316L SS sample included the presence of grooves of 3-5 µm. Smooth surface was achieved after the mechanical polishing of the samples with some evidence of scratches on the surfaces less than a micron in width. After electrochemical polishing (EP) smooth surface was revealed. No signs of microstructural features (e.g. grains and grain boundaries) were observed on MP and EP samples. FIG. 27 represents the AFM surface topography image of chemically etched 316L SS CE surface 110 sample. The chemical etching of the samples with glycergia resulted in the formation of grain boundary orientation dependent surface morphology, which shows that surface of all the grains and grain boundaries 140 are not in the same plane, i.e. the grains and grain boundaries are three dimensional. The surface topography that forms after the chemical etching of the samples is highly dependent on the material microstructure with protruding grains having a lower dissolution rate as compared to the grain boundaries. FIG. 27 exhibits a single phase austenitic (γ) structure. Grain size calculation using ASTM standard E112 reveals that the CE surface 110 samples has a grain size of 16 µm i.e. ASTM 9.

Figure 28:
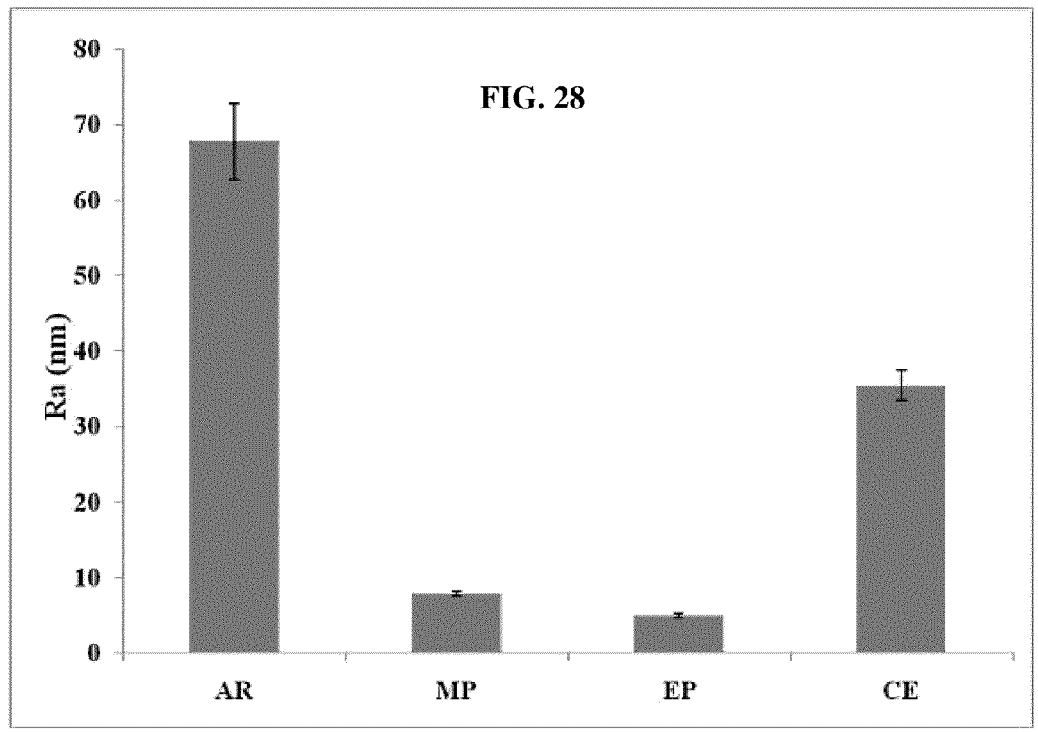
FIG. 28 is a bar graph of the average roughness value (Ra) measured on differently finished 316L SS surfaces using atomic force microscope (n=20, p<0.001).

AFM was used to measure the surface roughness of the AR, MP, EP and CE 316L SS samples, as previously indicated. Micro rough surfaces of metallic biomaterials show higher levels of cellular attachment; therefore, in order to estimate the influence of surface roughness of differently finished 316L SS on the behavior of endothelial cells, Ra values of these substrates were evaluated. Average roughness (Ra) values are shown in FIG. 28. The Ra value for AR samples is significantly higher ($p<0.001$) as compared to MP, EP and CE surface 110 samples. The roughness values measured on these substrates were: 67.8±5.1 nm, 7.9±0.27 nm, 5±0.3 nm and 35.5±2 nm for AR, MP, EP and CE respectively. The roughness values measured for AR substrates were about 2 times higher as compared to CE surface 110 specimens and about 14 times higher as compared to MP and EP samples.

Force volume imaging with the atomic force microscope (AFM) combines force measurement and topographic imaging capabilities. A force volume data set can be used to map the interaction forces between a sample and the AFM tip and correlate the force data with topographic information. Force volume measurements were obtained using a Nanoscope IIIa controller coupled with a multimode atomic force microscope. Force volume measurements were performed in fluid using a standard fluid cell that allows for the simple exchange of electrolyte solutions. Measurements were performed in 0.01 M NaCl as the fluid medium. The choice of the medium is based on the rationale of employing a low electrolyte concentration to reduce the instability of measurement performed under pure water and at the same time avoid the decrease in sensitivity that is well documented as salt concentration increases. The controls for collecting the force volume image were as follows: Set point ranged from 1 to 5 V with drive amplitude between 1 and 3 V. Drive frequency was between 28 and 34 kHz. Data were collected in tapping mode.

Figure 29:
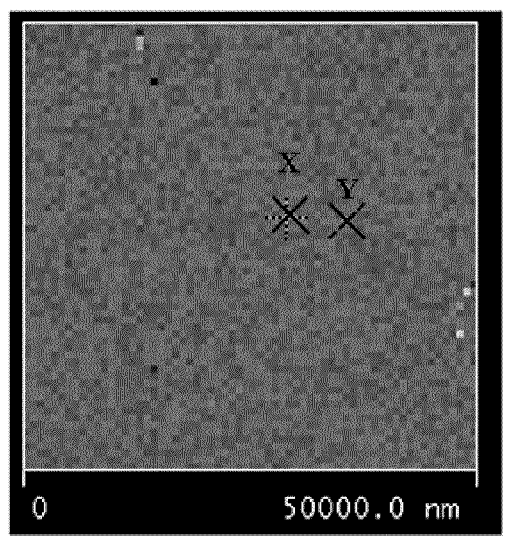
FIG. 29 is an are AFM image of force volume measurements across 50×50 μm areas on the surface of CE surface 110 (CE) 316L stainless steel substrates, where each image represents the composite of a 64×64 array of individual force curves taken in the presence of a 0.01 NaCl aqueous medium.

To maximize sensitivity, measurements were performed in a dilute saline solution at pH 7.0. Under these conditions, the silicon nitride tip on the end of the flexible cantilever bears a net negative charge. As a consequence, as the tip is brought into proximity of a similarly charged surface, the tip should be deflected away from the sample surface proportionate to the amount of charge. The possible site to site variability of charge was accounted for by examining 25 sites selected randomly across each surface. The electrostatic heterogeneity of the surfaces was more thoroughly examined by obtaining force volume arrays. In brief, this method scans a defined area of the surface by taking multiple force curves; in this case, 64 curves/line with 64 lines per area scanned, assigning a relative height by color to the electrostatic force level at each measurement taken. The result is a mosaic that depicts both the overall level of electrostatic force as well as map of the surface charge variability within that given area. AFM force volume image for CE surface 110 samples is shown in FIG. 29. When examining the force volume images of these surfaces, an array of light and dark colored pixels was displayed. A light colored pixel represents a repulsive force; whereas, a dark colored pixel represents an attractive force which is confirmed by force curves. Surface charge on CE surface 110 (CE) sample is positive (FIG. 29), because of higher concentration of dark colored pixels.

Figure 30A:
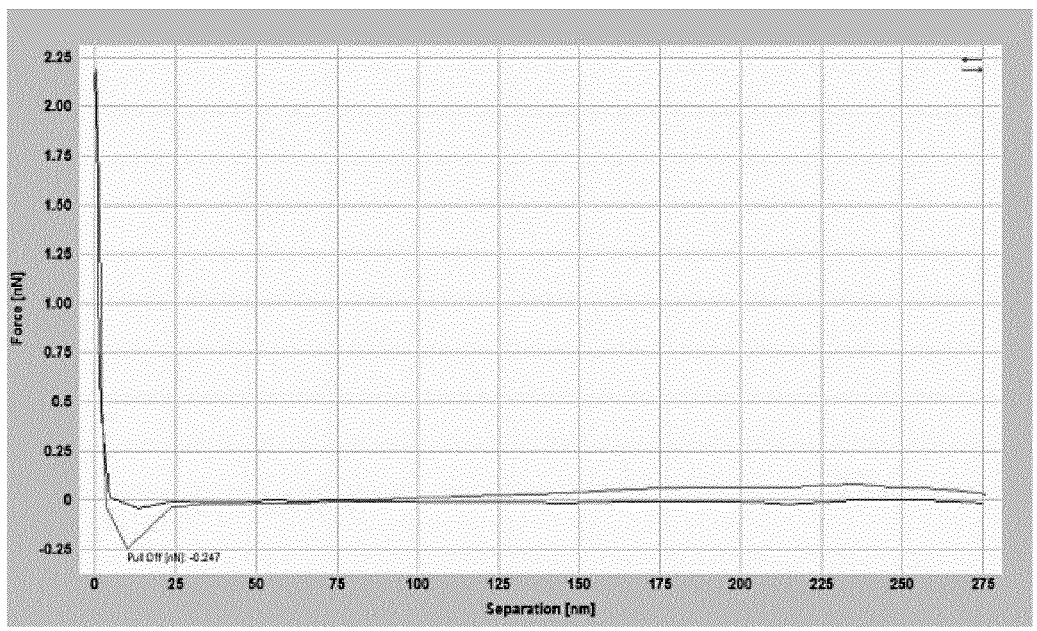
FIGS. 30A-B, are graphs of the representative force curves of (30A) CE surface 110 (CE) sample on the grain at X, FIG. 29, and (30B) of the chemically etched (CE) sample on the grain boundary at Y of FIG. 29.
Figure 30B:
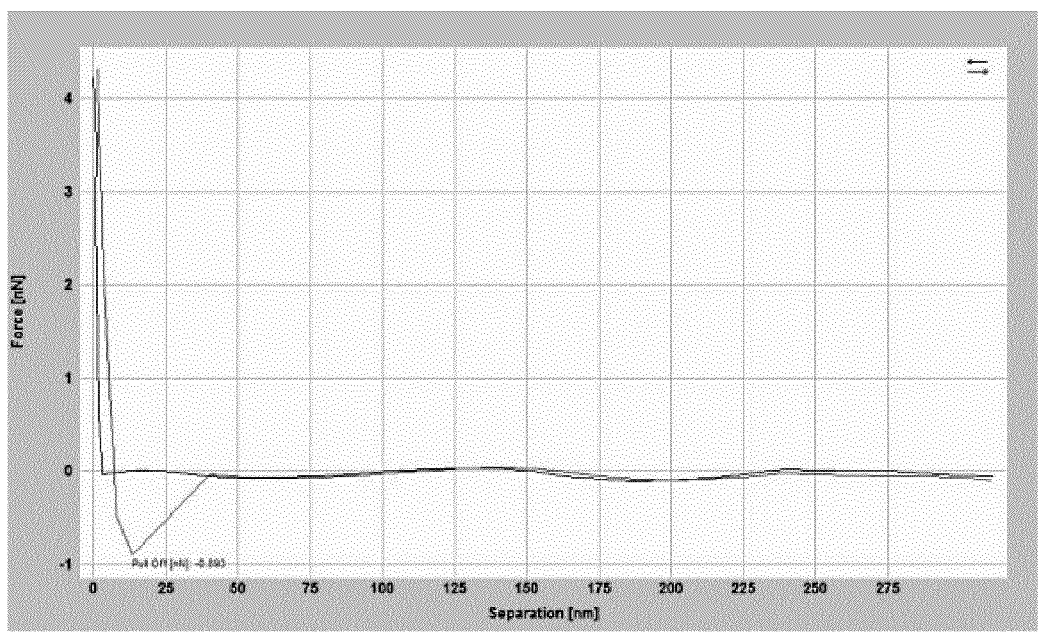

Force curve data were collected from force volume images. The curves were analyzed using SPIP 4.3.2.0 (scanning probe image processor) software, which generated the force of adhesion or the pull off force (as measured from the withdrawing part of the corresponding force-distance curves) values in nano newtons (nN). Force curves exhibiting either repulsive or attractive forces are illustrated in FIGS. 30A-B. As described above, as the negatively charged silicon nitride tip is brought close to a negatively charged surface, double layer forces cause the tip to bend away from the surface and depart from a linear pattern of descent to the surface. It is that departure that is measured as repulsive force. If the surface exhibits a positive charge relative to the tip, an attractive force is present that causes the tip to bend towards the surface and again depart from linear descent to the surface. Using this information to examine the individual metal surface curves presented in FIGS. 30A-B. Separate force curves were taken for grains and grain boundaries, to estimate the charge concentration.

Figure 31:
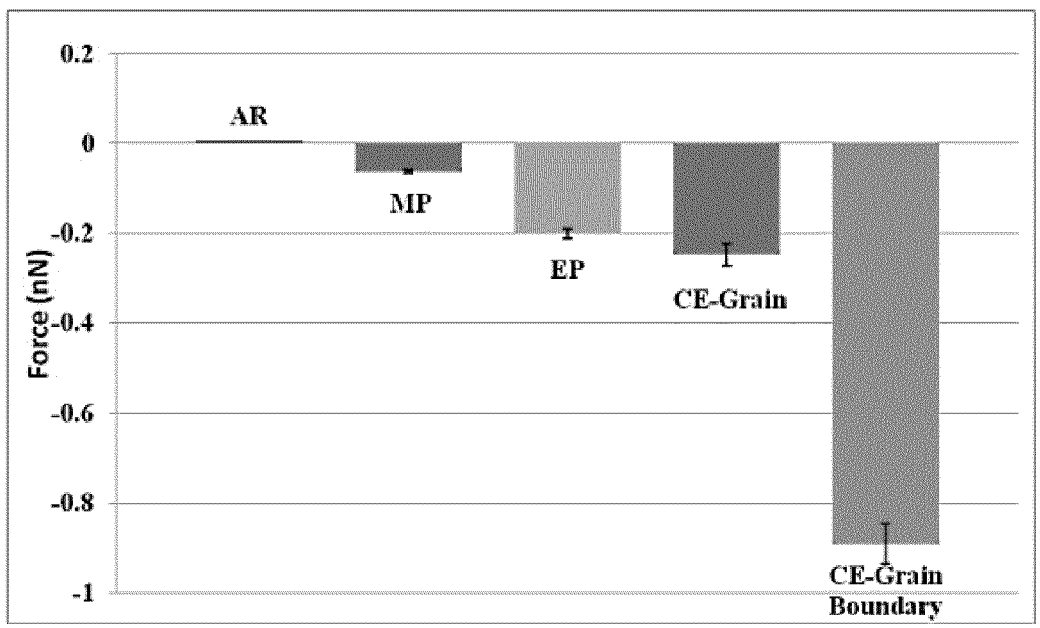
FIG. 31 is a graph of the average electrostatic force measurements on the surface of four different 316L stainless steel substrates, where the measurements were performed using a 5 nm silicon nitride tip in the presence of a 0.01M NaCl medium pH 7.4, and the force measurement value for each substrate represents the mean data from 35 different samples on which 10 sites were analyzed using 10 measurements at each site.

From FIG. 30A, the force curves taken on grains of the CE surface 110 (CE) exhibited positive charge concentration between about −0.2 to −0.3 nN. But the force curve on the CE-grain boundaries 140 on the CE surface 110 showed a high positive charge concentration (FIG. 30B) between about −0.80 to −1.0 nN. The average electrostatic force values measured on differently finished 316L SS surfaces are shown in FIG. 31. As illustrated, significantly higher electrostatic force relative to other surfaces was measured on CE surface 110 grain boundaries 140.

Figure 32:
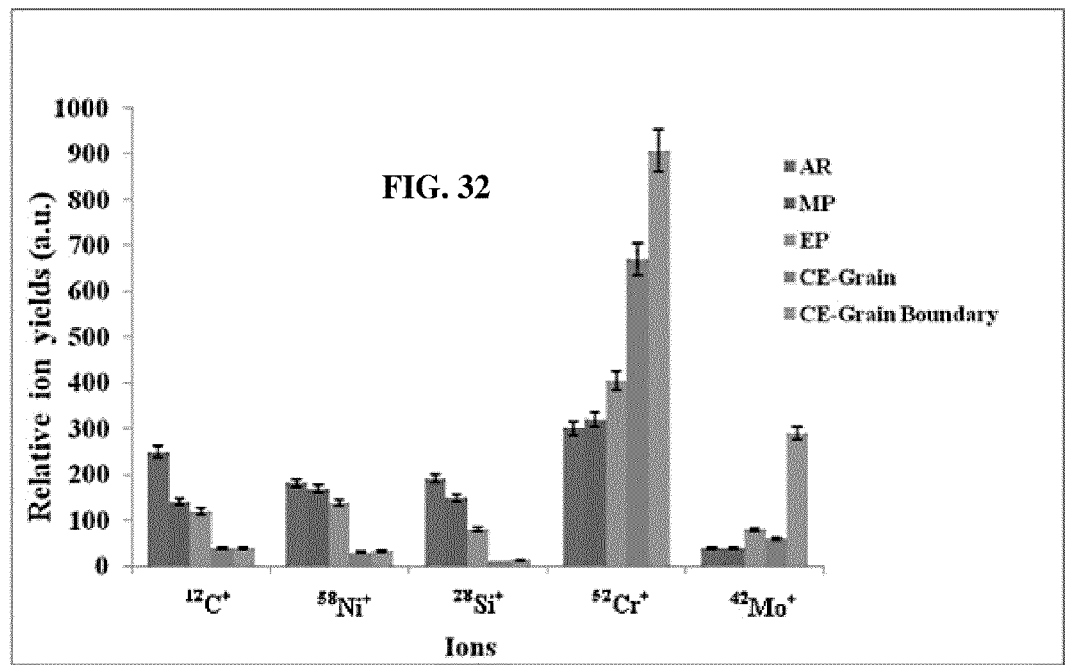
FIG. 32 is a bar graph representing relative concentration of positive ions on differently finished 316L stainless steel substrates obtained using time of fight SIMS, where the data has been normalized with respect to $^{56}Fe^+$.
Figure 33:
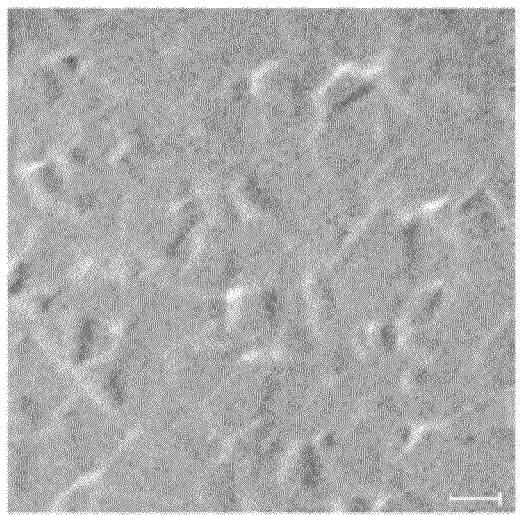
FIG. 33 is a time of flight SIMS image representing positive ion concentration on 316L stainless steel CE surface 110 substrates, where the bright areas indicate more concentration of positive ions (bar-10 μm).

Static ToF SIMS generates mass spectrum from the outer 1-2 nm of the sample. ToF-SIMS data were acquired using a Trift II time of flight secondary ion mass spectrometer with a 22 keV $Au_3^+$ primary ion source. The total primary ion flux was maintained below $10^{12}$ ions/cm$^2$ to ensure static conditions. High mass resolution spectra were acquired with a raster size of 100×100 μm. At least ten spectra were recorded on each sample. Positive and negative ion spectra and images were separately acquired and analyzed, and, to visualize the distribution of these ions on the surface of differently finished 316L SS, their corresponding ToF SIMS images were taken. An image is generated by rastering a finely focused ion beam across the sample surface. Due to the parallel detection nature of ToF SIMS, the entire mass spectrum is acquired from every pixel in the image. The mass spectrum and the secondary ion images are then used to determine the composition and distribution of sample surface constituents. Positive and negative ion spectra for grains 100 and grain boundaries 140 were acquired by selecting the region of interest (ROI) from the total ion image. FIG. 32 shows peak intensities of various elemental ions in the positive ion spectra for surfaces under investigation. The intensities have been normalized with respect to $^{56}Fe^+$ peak. The results included the following: Cr ion: 650 relative ion yield a.u. ("arbitrary unit") for grain) and 890 (grain boundary); Mo ion: 50 (grain)/290 (grain boundary); for the carbon, nickel, and silicon ions the values are same for GR and GB roughly 44 a.u., 25 a.u., and 10 a.u., respectively. Results indicate high concentrations of chromium and molybdenum ions on CE surface 110 samples at the grain boundaries 140. Also, within grains on the CE surface 110, the chromium ion concentration was higher as compared to AR, MP and EP. Low concentrations of carbon, nickel and silicon were also observed on the CE surface 110 samples. FIG. 33 represents the total positive ion image for differently finished 316L SS samples. Total positive ion image for CE surface 110 (CE) samples reveals high concentration of positive ions on the grain boundaries 140 as compared to that on grains and supports the data obtained from AFM force volume curves that also indicate high positive charge concentration on grain boundaries 140.

For protein adsorption, all studies were performed with single protein solution at physiological concentrations. Single protein solutions provide more defined information, for example, the increased affinity of a particular type of protein to AR, MP, EP or CE 316L SS surface. The proteins evaluated were: albumin, fibronectin, vitronectin and fibrinogen.

For fluorescent labeling of proteins, a phosphate buffer saline solution (PBS) was used to prepare the protein solution. Concentration of human albumin, fibronectin, vitronectin and fibrinogen proteins in the PBS solution will be; 60 mg/mL, 1 mg/mL, 1 mg/mL, 2.5 mg/mL respectively. One milliliters of protein solution was pipetted onto the samples placed in tissue culture wells. Tissue culture wells were placed in a sterile humidified incubator at 37° C. for 1 hr. This was followed by the injection (200 μl per sample) of the primary antibody solution. After 60 min incubation time at 37° C. the samples were rinsed with PBS and the secondary antibody (fluorochrome, 200 μl per sample) solution will introduced in the ratio of 1:200 for 60 min at 37° C.

The microscopy and intensity analysis of the fluorescent images of the protein-adsorbed samples, labeled with the appropriate fluorescent antibody, was obtained for all the samples under similar conditions (acquisition time, brightness, contrast) using a fluorescence microscope NIH Image J 1.62 was be used to estimate the fluorescence intensity of the images. Particular attention was paid to keeping samples wet during the measurements since drying of the samples was found to deteriorate the image quality and reproducibility of the results. For each sample the average fluorescence signal in the two different pattern regions was measured over a minimum area of 0.01 mm$^2$. For a quantitative measurement of protein contrast, a common background intensity level was defined (dark signal). Regions of interest were photobleached completely (area: 80×25 μm$^2$) and the remaining intensity was subsequently subtracted as background from all measured fluorescence signals.

Figure 34:
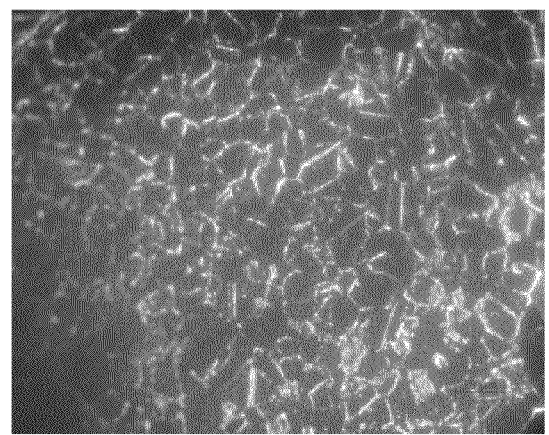
FIG. 34 is a fluorescent micrograph of albumin adsorption after 120 min on CE surface 110 (CE) 316L stainless steel substrates, where the bright areas indicate more concentration of protein (bar-20 μm), where the specific adsorption of albumin on the grain boundaries on CE surface 110.
Figure 38:
FIG. 38 is a fluorescent micrograph of fibrinogen adsorption after 120 min on CE surface 110 (CE) 316L stainless steel substrates, where the bright areas indicate more concentration of protein (bar-20 μm), where there is no protein adsorption on CE surface 110 (CE) sample.

Similar fluorescence images were observed for albumin, fibronectin and vitronectin for AR, EP, and MP samples; therefore, only fluorescence images for albumin and fibrinogen adsorption on the CE surface 110, as presented in FIG. 34 and FIG. 38. As a control for non specific adsorption of antibody, samples were exposed to anti human albumin primary antibody and secondary antibody (fluorochrome). There was no observed fluorescence intensity on control samples. It was observed that on CE surface 110 (CE) samples, albumin, fibronectin and vitronectin adsorption was specifically on grain boundaries; whereas, no such adsorption pattern was observed on AR, MP and EP substrates. The specificity of protein adsorption on the grain boundaries for CE surface 110 samples can be related to the higher adhesion force and more concentration of positive ions on the grain boundary 140. As shown in FIG. 38, there was no evidence of fibrinogen adsorption on the grain boundaries or grains on chemically etched samples after 120 min.

Figure 37:
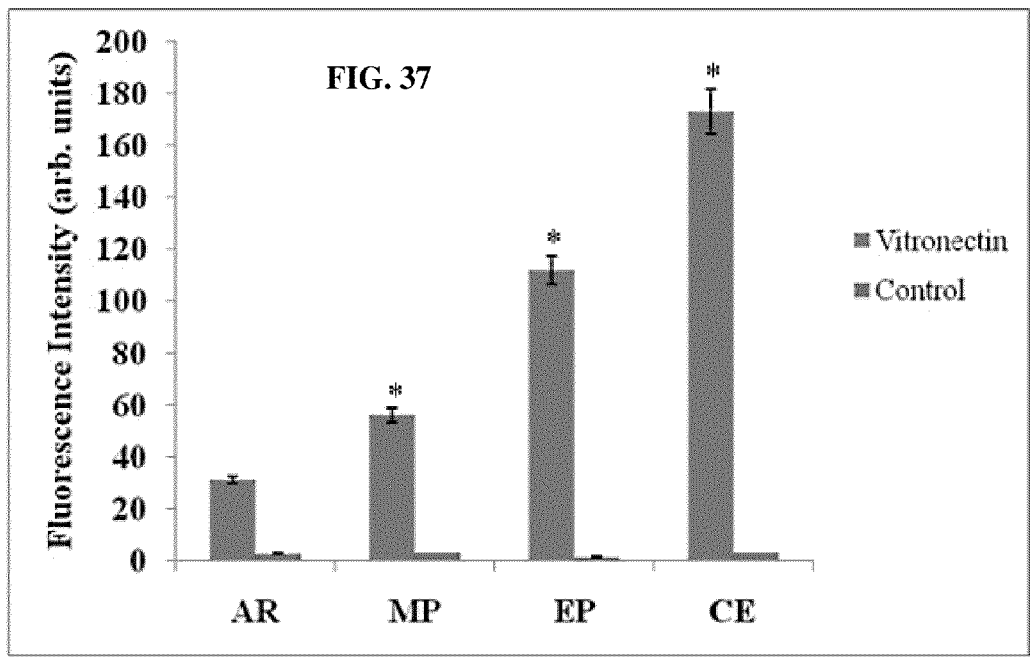
FIG. 37 is a bar graph showing the fluorescent intensity of adsorbed vitronectin after 120 min on (a) as received (AR), (b) mechanically polished (MP), (c) electrochemically polished (EP) and (d) CE surface 110 (CE) 316L stainless steel substrates (n=15,*p<0.01).
Figure 39:
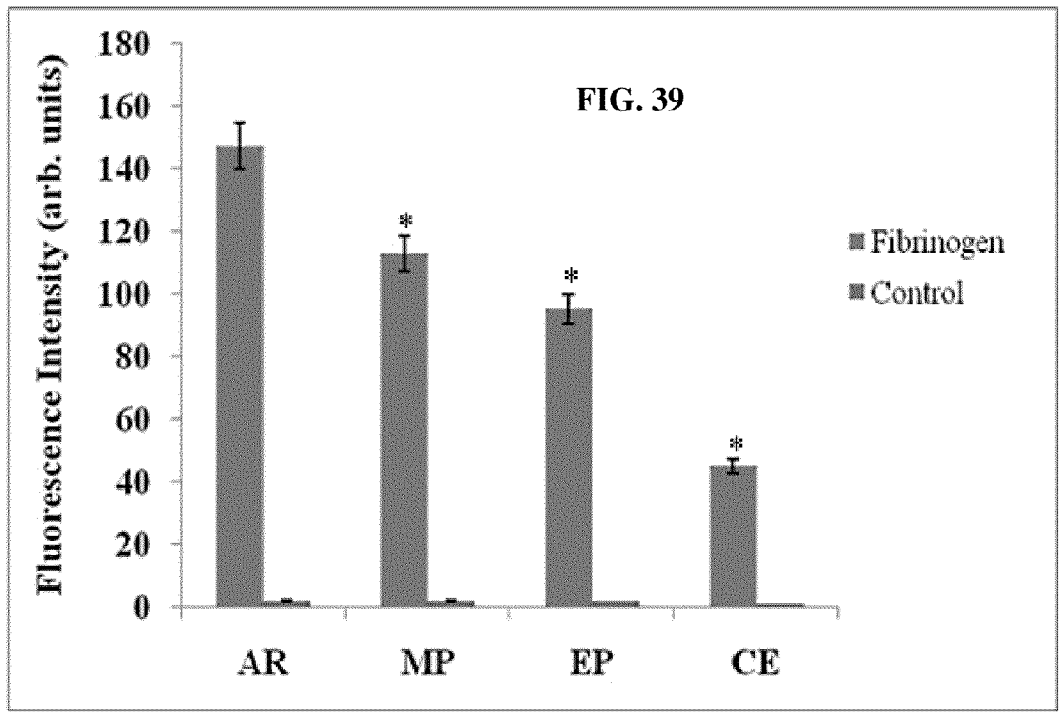
FIG. 39 is a bar graph showing the fluorescent intensity of adsorbed fibrinogen after 120 min on (a) as received (AR), (b) mechanically polished (MP), (c) electrochemically polished (EP) and (d) CE surface 110 (CE) 316L stainless steel substrates (n=15,*p<0.01).
Figure 40:
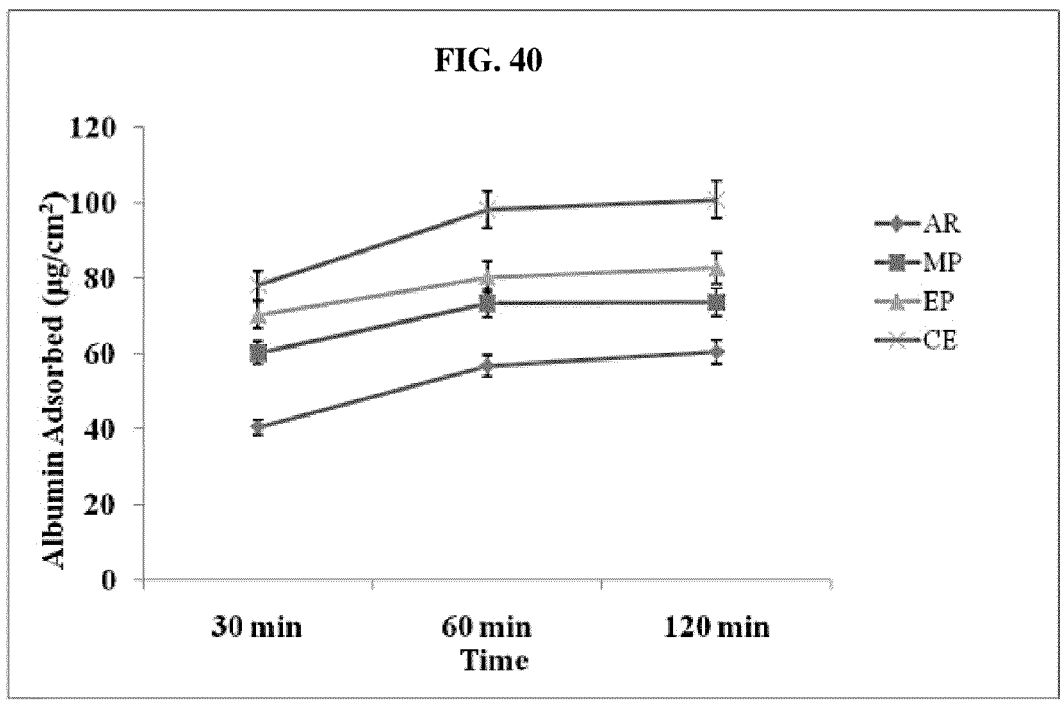
FIG. 40 is a bar graph of radiolabeled ($^{125}I$) albumin adsorption on (a) as received (AR), (b) mechanically polished (MP), (c) electrochemically polished (EP) and (d) CE surface 110 (CE) 316L stainless steel substrates.
Figure 41:
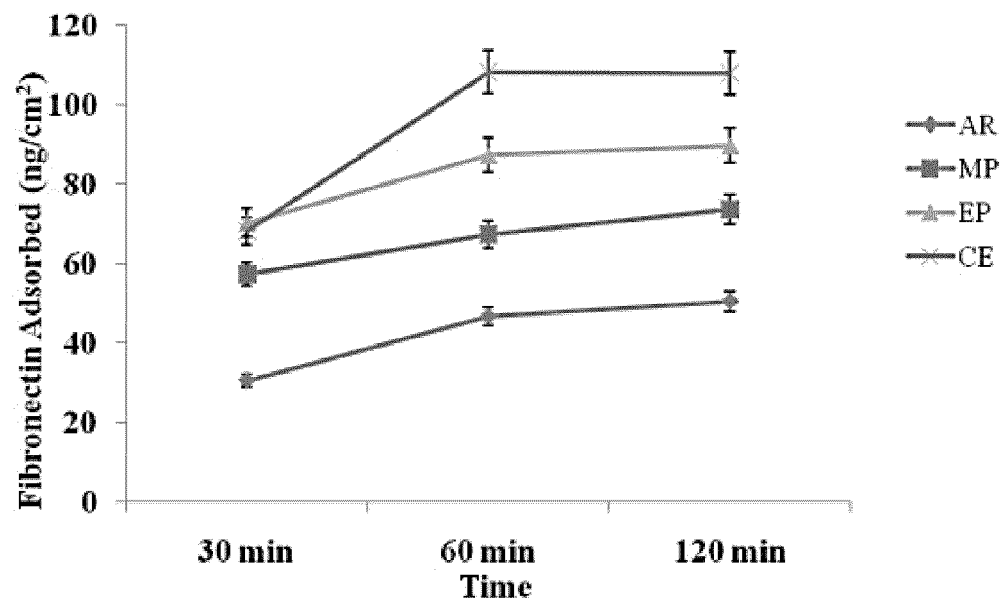
FIG. 41 is a bar graph of radiolabeled ($^{125}I$) fibronectin adsorption on (a) as received (AR), (b) mechanically polished (MP), (c) electrochemically polished (EP) and (d) CE surface 110 (CE) 316L stainless steel substrates.

Quantification of the fluorescence intensity of adsorbed proteins on the samples was done, where FIG. 35 shows the CE surface 110 (CE) sample with 150 fluorescence intensity a.u. (arbitrary units); FIG. 36, shows the CE surface 110 samples with 180 fluorescence intensity a.u; FIG. 37 shows the CE surface 110 samples with 177 fluorescence intensity a.u; and FIG. 39 shows the CE surface 110 samples with 45 fluorescence intensity a.u. Statistical analysis suggests that albumin, fibronectin and vitronectin adsorption on CE surface 110 samples was significantly higher (p<0.01) as compared to AR, MP and EP samples. In contrast, fibrinogen adsorption was higher on as received (AR) samples in comparison to MP, EP and CE specimens. CE surface 110 (CE) samples showed lowest fibrinogen adsorption. As a control for any contribution of non specific adsorption of antibodies, the surfaces were also exposed to anti-protein primary antibody and secondary fluorescence. The observed fluorescence intensity were very small compared to signal from specific antibody against the serum proteins, implying that non-specific binding makes typically less than 5% contribution in comparison to the specific signals observed in case of albumin, fibronectin, vitronectin and fibrinogen.

Albumin, fibronectin, vitronectin and fibrinogen were labeled with $^{125}I$ using Bolton and Hunters reagent (N-succinimidyl 3-(4-hydroxy,5-[$^{125}I$]iodophenyl)-propionate) to estimate the amount of protein adsorbed on different 316L SS surfaces. Standard protocol (Perkin Elmer Life Sciences, MA) used for radiolabeling of proteins using Bolton and Hunters solution. Each protein solution was spiked with a low concentration of corresponding radiolabeled protein. The estimated overall activity of the solutions was 0.64×10$^6$ dpm/ml. Each dynamic protein adsorption study was done by immersing the material pieces in the spiked single protein solution for 30 min, 60 min and 120 min at 37° C. After removal from the solution, the activity on the specimens was assessed in an automated gamma counter. Total bound protein was calculated using the known specific activity of the radiolabeled protein, normalizing the final amount of labeled bound concentration based on its proportion of the total protein.

Figure 42:
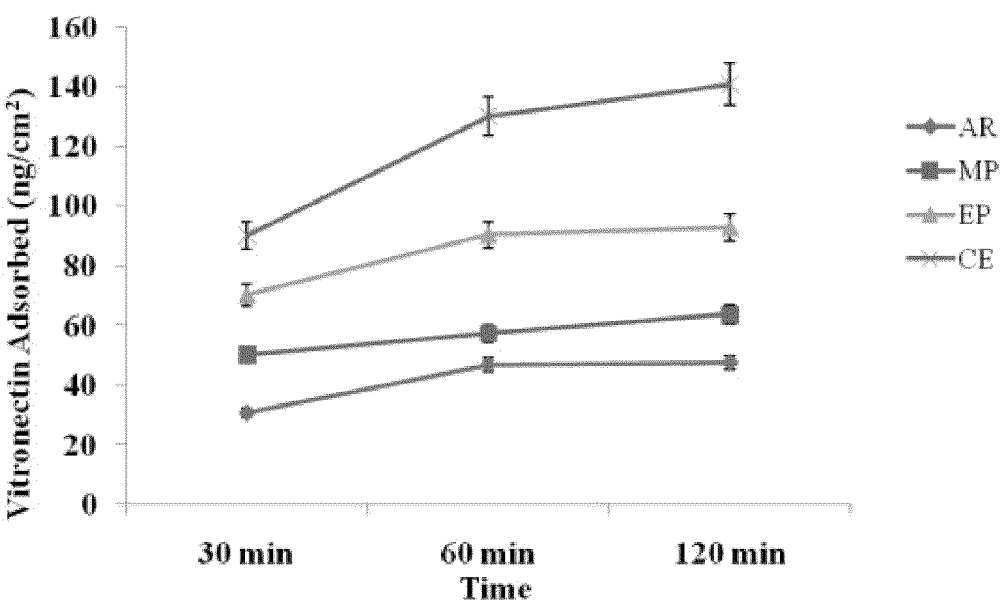
FIG. 42 is a bar graph of radiolabeled ($^{125}$I) vitronectin adsorption on (a) as received (AR), (b) mechanically polished (MP), (c) electrochemically polished (EP) and (d) CE surface 110 (CE) 316L stainless steel substrates.

Results of radiolabeled ($^{125}$I) protein adsorption on AR, MP, EP and CE surface 110 (CE) samples are shown in FIG. 40, FIG. 41, FIG. 42 and FIG. 43. Albumin adsorption (µg/cm$^2$) on CE surface 110 (CE) sample was higher as compared AR, MP and EP samples at all time points (30, 60 and 120 min). Statistically significant difference in albumin adsorption between CE surface 110 and AR ($p<0.001$)/MP ($p<0.01$) were observed after 30 min, and between CE and AR ($p<0.001$)/MP ($p<0.01$)/EP ($p<0.01$) after 60 and 120 min. Radiolabeled fibronectin adsorption (ng/cm$^2$) shown in FIGS. 41 reveals that the amount of protein adsorbed was higher for CE surface 110 (CE) specimens as compared to AR and MP samples after 30 min, and AR, MP and EP samples after 60 and 120 min. The CE surface 110 specimens included 69, 132 and 131 ng/cm$^2$ of fibronectin absorbed for 30, 60 and 120 min, respectively. Statistically significant difference between CE and AR ($p<0.001$)/MP ($p<0.01$) after 30 min, and CE and AR ($p<0.0001$)/MP ($p<0.001$)/EP ($p<0.01$) after 60 and 120 min was observed. Amount of vitronectin adsorbed (ng/cm$^2$) on differently finished 316L SS surfaces is shown in FIGS. 42. The CE surface 110 specimens included 69, 131 and 139 ng/cm$^2$ of vitronectin absorbed for 30, 60 and 120 min, respectively. Protein adsorbed is higher for chemically etched samples after all time periods. Statistically significant difference in vitronectin adsorption was observed between CE and AR ($p<0.0001$)/MP ($p<0.001$)/EP ($p<0.01$) specimens after 30, 60 and 120 min. Fibrinogen adsorbed (ng/cm$^2$) AR, MP, EP and CE is illustrated in FIGS. 43. The amount of fibrinogen adsorbed is lowest for chemically etched after all time periods. Statistically significant difference between CE and AR ($p<0.001$)/MP ($p<0.01$)/EP ($p<0.01$) were observed after 30, 60 and 120 min. Higher radiolabeled albumin, fibronectin and vitronectin adsorption and lower fibrinogen adsorption on CE surface 110 samples as compared to other samples types, supports the fluorescence results discussed above. Higher fibrinogen adsorption leads to more blood clotting and thrombus formation, which is bad for cardiovascular materials. This graph shows that CE surfaces 110 are less likely to cause thrombus formation.

The interaction between proteins and the surface of a material is a fundamental phenomenon with important implications in a number of biological processes. For example the irreversible binding and subsequent denaturation of albumin to hydrophobic surfaces is thought to be the reason for the poor attachment of cells to many polymers. Chemically micropatterned surfaces, which have functionalized (polar) and unfunctionalised (non-polar) domains, and which consequently promote cell attachment, provide a useful means of directing cell growth to specific regions of device surfaces. Since interactions between surfaces and proteins occur in aqueous solutions, an electrostatic double layer will exist either charged surface functional groups and/or through the adsorption of ions from solution. The surface charge is balanced by the accumulation of an equal number of oppositely charged counter ions that are either bound to the surface to a form the Stem layer or present in an atmosphere above the surface to form an electrostatic double layer. Since proteins are usually charged molecules in aqueous solution the presence of this electrostatic double layer with its associated electric field will have an important influence on the interaction between biomaterial surfaces and proteins.

The surface of a biomaterial is the most important part determining the acceptance by and compatibility with the environment. In many cases, the surface of bulk materials may require to be modified and engineered in the desired direction. This is especially important for materials used in biological media, since the surface charge, hydophilicity and wettability are important for thrombosis formation, cell attachment or cell proliferation. Albumin, fibronectin, vitronectin and fibrinogen adsorption on as-received (AR), mechanically polished (MP), electrochemically polished (EP) and CE surface 110 (CE) 316L SS samples have been compared. AR samples had a small net negative charge on the surface and low concentration of positive ions. In contrast, CE surface 110 specimens showed a very high concentration of positive ions on the grain boundaries 140. The overall concentration of positive ions on the CE surfaces 110 was much higher as compared to other specimens. AFM force volume data also confirms that CE surface 110 samples had a net positive charge, which was much higher as compared to AR, MP and EP specimens.

Electrostatic forces are among the key factors governing biomolecular interactions involved in vascular physiologic processes such as cell-cell, cell-substrate, and receptor-ligand interactions as well as pathophysiologic processes such as thrombosis. This electrostatic interaction also plays a significant role in limiting interaction between endothelial lining, which is highly electronegative, and majority of plasma proteins and blood borne cells, which similarly bear a net negative charge. Higher albumin, fibronectin and vitronectin adsorption and lower fibrinogen adsorption was observed on CE surface 110 (CE) samples as compared to as received (AR), mechanically polished (MP) and electrochemically polished (EP) specimens. Since most of the plasma proteins as mentioned earlier are highly electronegatively charged, and a net negatively charged protein should be repelled by an electronegative surface, high positive charge on chemically etched specimens, specifically on the grain boundaries, is responsible for higher adhesion of plasma proteins onto CE specimens with the exception of fibrinogen. Different fibrinogen binding on these surfaces can be due to molecular organization (i.e., distribution, orientation, and conformation) of its constituents. Most plasma proteins are a distinct mix of cationic, anionic, and nonpolar, hydrophobic regions. Therefore, the charge distribution and arrangement of polar and non-polar areas on the protein molecule at the time of interaction with the surface is also a key factor determining the type of interaction between the protein molecule and the surface and ultimately the protein adsorption and retention. In general, the 316L SS CE surface 110 samples showed more adsorption of proteins (albumin, fibronectin and vitronectin) responsible for tissue integration, endothelial cell adhesion, spreading, proliferation and migration and low levels of adsorption of protein (fibrinogen) which provides the ligands for platelets and monocytes recognized as an important contributor of thrombosis, inflammation and arterial restenosis associated with intimal hyperplasia.

EXAMPLE V

GREDVY Peptide Adsorption and HAEC Attachment on the CE Surface

Currently used stent surfaces fail to endothelialize rapidly and therefore the proliferative phenomenon occurs in the absence of complete endothelialization. Gly-Arg-Glu-Asp-Val-Tyr (GREDVY) peptide, an adhesion peptide that selectively supports attachment and spreading of endothelial cells, is adsorbed on as-received (AR), mechanically polished (MP), electrochemically polished (EP) and CE surface 110 (CE) 316L stainless steel (SS) surfaces. Adhesion to and spreading of human aortic endothelial cells (HAECs) on these four surfaces were compared. HAEC density, spreading and number of activated focal adhesion contacts formed on CE surfaces 110 were significantly higher as compared to the other three surfaces, indicating a higher concentration of GREDVY peptide on CE surface 110 samples. This increased level of cell adherence and spreading on CE surfaces 110 was maintained even when HAEC seeding was delayed to 31 days after peptide adsorption, which is associated with high positive charge concentration at the grain boundaries 140 on CE surface 110 specimens; as observed by AFM, ToF SIMS and demonstrated by specific adsorption of anionic dye on the grain boundaries 140. The surface microstructure of CE surface 110 has important implications for development of surfaces to improve the rate of endothelialization on vascular prosthetic devices.

As-received (AR), mechanically polished (MP), electrochemically polished (EP) and chemically etched (CE) 316L SS samples were prepared for GREDVY peptide adsorption, as discussed previously.

AFM and ToF SIMS data showed the grains of the CE surface 110 (CE) exhibited positive charge concentration. The force curve on the grain boundaries 140 showed very high positive charge concentration. Total positive ion image as analyzed by ToF SIMS for CE samples reveals high concentration of positive ions on the grain boundaries as compared to that on grains and supports the data obtained from AFM force volume curves, which also indicate high positive charge concentration on grain boundaries. To further evaluate the distribution of positive and negative charges on the surface, anionic (Fluorescein-5-(and-6)-sulfonic acid) and cationic (Lissamine™ rhodamine B) dye adsorption on AR, MP, EP and 316L SS CE surface 110 samples was performed. One milliliter of dye solution was pipetted onto the samples placed in tissue culture wells. Tissue culture wells were placed in a sterile humidified incubator at 37° C. for 1 hr. After 60 min incubation time at 37° C. the samples were rinsed with PBS and qualitative and quantitative evaluation of the samples was done.

Anionic and Cationic dye adsorption was studied on AR, MP, EP and CE surface 316L SS samples. FIG. 44 and FIG. 45 represent the fluorescence images of the adsorbed anionic and cationic dye on the specimens on CE surface 110 (CE) samples, respectively. Anionic dye adsorption was specifically on the grain boundaries 140, as shown in FIG. 44 as all the bright areas are grain boundaries 140 and the rest of the image is dark; whereas, no such adsorption pattern was observed on AR, MP and EP substrates (not shown). The specificity of anionic dye adsorption on the grain boundaries 140 on CE surface 110 samples can be related to the higher adhesion force and higher concentration of positive ions on the grain boundary confirmed by AFM and ToF SIMS results, shown previously. There was no evidence of cationic dye adsorption on the grain boundaries 140 (FIG. 45) or grains on CE surface 110 samples, also comparatively more bright areas with adsorbed cationic dye were observed on AR specimens as compared to other sample types, confirming that the grain boundaries include positive charges, i.e. positive charges repel cationic dye adsorption.

Figure 46:
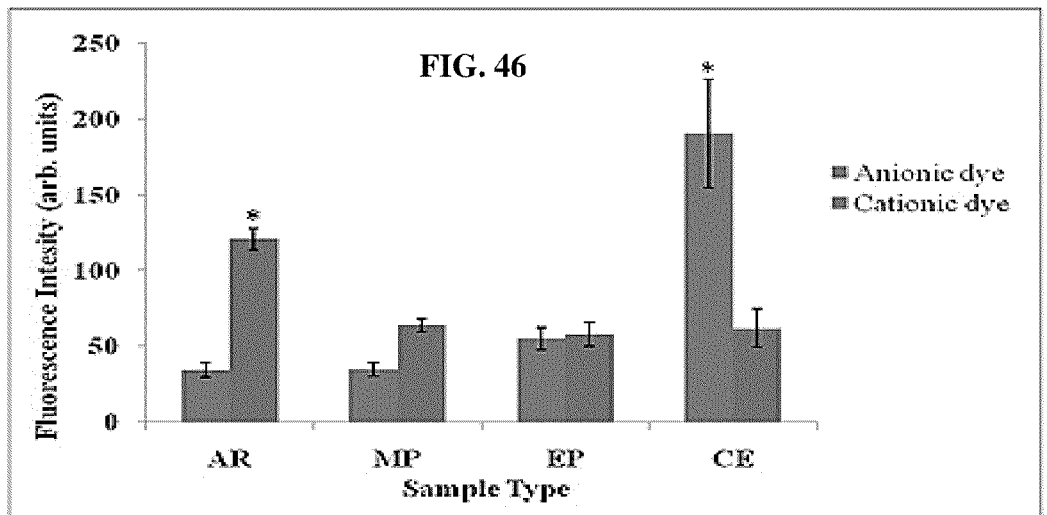
FIG. 46 is a bar graph showing fluorescence intensity of anionic and cationic dye adsorbed on (a) as received (AR), (b) mechanically polished (MP), (c) electrochemically polished (EP) and (d) CE surface 110 (CE) 316L stainless steel substrates (n=20,*p<0.01).

Quantification of the fluorescence intensity of the adsorbed dye on the samples is shown in FIG. 46. The CE surface 110 (CE) samples included a 185 fluorescence intensity a.u. (arbitrary units) for the anionic sample and 55 fluorescence intensity a.u. for the cationic sample. Statistical analysis suggests that anionic dye adsorption on CE samples was significantly higher ($p<0.01$) as compared to AR, MP and EP samples. In contrast, cationic dye adsorption was higher on as received (AR) samples in comparison to MP, EP and CE specimens. As a control for any contribution of non-specific adsorption, fluorescence intensity of the surfaces was observed which was negligible as compared to signal from specific dye, implying that non-specific binding makes typically less than 1% contribution in comparison to the specific signals observed in case of anionic and cationic dye adsorption.

Fluorescent images of the dye-adsorbed samples was obtained for all the samples under similar conditions (acquisition time, brightness, contrast) using a fluorescence microscope. NIH Image J 1.62 was be used to estimate the florescence intensity of the images. Particular attention was paid to keeping samples wet during the measurements since drying of the samples was found to deteriorate the image quality and reproducibility of the results. For each sample the average fluorescence signal in the two different pattern regions was measured over a minimum area of 0.01 mm$^2$. For a quantitative measurement of dye contrast, a common background intensity level was defined (dark signal).

Fibronectin sequence Gly-Arg-Glu-Asp-Val-Tyr (GREDVY) peptide was dissolved in phosphate buffer saline solution (PBS) in the ratio 1:100. Peptide solution (100 µl per sample) was pipetted onto the samples placed in tissue culture wells. Non specific peptide Gly-Arg-Ala-Asp-Ser-Pro (GRADSP) solution was also prepared and samples incubated in this solution and specimens with no peptides were used as controls. Tissue culture wells with samples were placed in a sterile humidified incubator at 37° C. for 2 hr. After 120 minutes of incubation at 37° C. the samples were rinsed with PBS.

Since Gly-Arg-Glu-Asp-Val-Tyr (GREDVY) peptide is known to promote endothelial cell adhesion, it is important to investigate the stability of this peptide after adsorption. Therefore, after adsorption of this peptide on AR, MP, EP and CE samples the specimens were stored dry in ambient conditions for 7 and 31 days and changes in endothelial cell density, spreading and number of focal adhesion contacts formed on the samples was studied at the end of each time period.

As-received, mechanically polished, electrochemically polished and CE surface 110 samples with no peptide and adsorbed non specific (GRADSP) and specific (GREDVY) peptides were sterilized in ultra violet light (UV) for 24 hrs. Human aortic endothelial cells were cultured as previously indicated. After the specified culture time, endothelial cells were rinsed with PBS for 1 min followed by fixing with 4% formaldehyde in PBS and again rinsed in PBS. Fixed cells were stained with 2% Giemsa. Endothelial cell density and spreading area on samples with no peptide, non specific peptide (GRADSP) and specific peptide (GREDVY) was compared. Cell counting was carried out using a stratified random sampling method. Numbers of cells were counted on 60 different fields using reflective light microscopy. For calculating the cell spreading area, representative images were captured with the use of a CCD camera coupled to a fluorescence/light microscope (Zeiss Axioplan 2 Imaging,). Images were than analyzed using NIH Image J 1.62.

Figure 47:
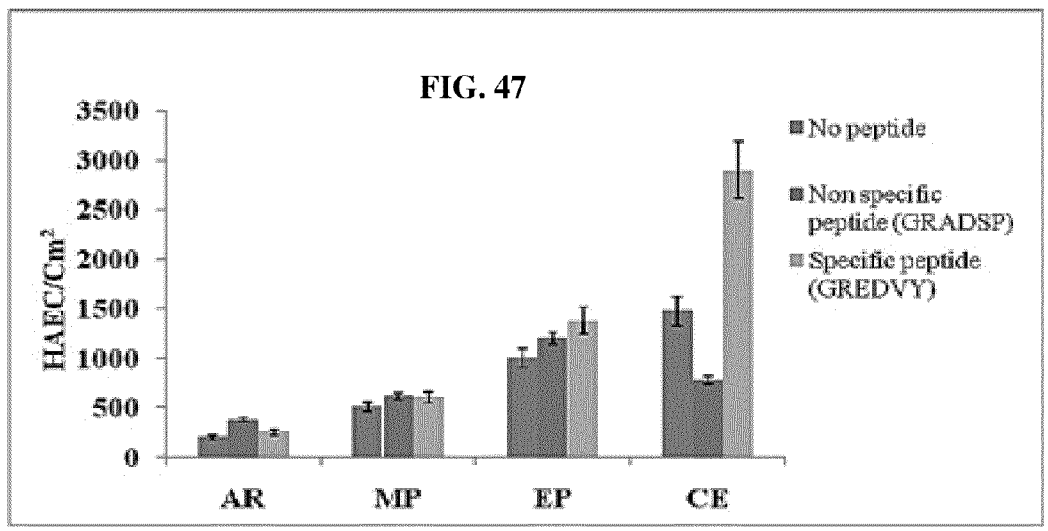
FIG. 47 is a bar graph showing endothelial cell density after 24 hrs on (a) as received (AR), (b) mechanically polished (MP), (c) electrochemically polished (EP) and (d) CE surface 110 (CE) 316L stainless steel substrates with no peptide and non specific (GRADSP) and specific (GREDVY) peptides adsorbed on the surfaces.

FIG. 47 represents endothelial cell density on AR, MP, EP and CE surface 110 (CE) with no peptide, non-specific peptide (GRADSP) and specific peptide (GREDVY) adsorbed. GRADSP was used as an inactive control for nonspecific peptide-induced cell adhesion. For the CE samples, no peptide was 1500 HAEC/cm$^2$; non Specific Peptide was 750 HAEC/cm$^2$; and the specific peptide was 2900 HAEC/cm$^2$. Statistically significant difference ($p<0.05$) in number of cells attached per cm$^2$ on AR samples were observed, and an increase in number of endothelial cells with non-specific peptide adsorption was noted, whereas, HAEC density was similar for the AR surface with no peptide and specific peptide (GREDVY) adsorbed. For CE surface 110 samples statistically significant difference in cell density was observed between no peptide/GRADSP ($p<0.0001$), no peptide/GREDVY ($p<0.001$), and GRADSP/GREDVY ($p<0.01$) adsorbed sample groups. Overall, the endothelial cell density on CE samples with GREDVY peptide was $\geqq 2$ times the HAEC density on other samples. The results also indicate that GREDVY peptide could be grafted on CE surface 110 (CE) samples and increased the HAEC density by two fold as compared to the CE specimen with no peptide adsorbed.

Human aortic endothelial cell spreading areas on AR, MP, EP and CE 316L SS specimens are shown in FIG. 48. On CE surface 110 (CE) samples, as compared to CE specimen with no peptide significantly lower ($p<0.05$) and higher ($p<0.001$) HAEC spreading area was observed for GRADSP and GREDVY adsorbed specimens, respectively. The CE samples included no peptide: 3900 HAEC spreading area ($\mu m^2$); non-specific peptide: 2990 HAEC spreading area ($\mu m^2$); and specific Peptide: 8980 HAEC spreading area ($\mu m^2$). In summary, HAEC spreading area on GREDVY adsorbed CE specimens was $\geqq 2$ times as compared to other samples.

Number of activated focal adhesion contacts formed by human aortic endothelial cells on GREDVY grafted as-received, mechanically polished, electrochemically polished and chemically etched samples were estimated using NIH Image J 1.62, as previously indicated. In cultured cells, Focal adhesion kinase (FAK) is localized to focal adhesion contacts and becomes phosphorylated and activated in response to integrin-mediated binding of cells to the extracellular matrix, suggesting an important role in cell adhesion and/or migration. FIG. 49 shows the number of activated focal adhesion contacts formed by HAECs on AR, MP, EP and CE surface 110 (CE) samples with no peptide, non-specific peptide (GRADSP) and specific peptide (GREDVY). For the CE samples, no Peptide: 2.5 Focal adhesion points/$\mu m^2$ of endothelial cells; Non Specific Peptide: 1.2 Focal adhesion points/$\mu m^2$ of endothelial cells; and specific peptide: 7.5 Focal adhesion points/$\mu m^2$ of endothelial cells. On CE surface 110 (CE) specimens significant increase ($p<0.001$) in number of focal adhesion contacts on samples with GREDVY peptide was noted as compared to samples with no peptide and non specific peptide (GRADSP). Overall, significantly higher ($p<0.001$) number of activated focal adhesion contacts were observed on CE specimens with GREDVY peptide adsorbed as compared to other samples, specifically, a 10 fold increase was noticed as compared to EP specimens.

Morphology of HAECs after 24 hrs of culture on CE 316L SS CE surface 110 samples with GREDVY peptide adsorbed is shown in FIG. 50. As-received and mechanically polished samples showed rounded endothelial cell morphology and there was no evidence of cell-cell interaction or extracellular matrix formation (not shown). CE surface 110 samples showed evidence of higher cell spreading area, formation of cell-cell junctions and cell dividing on the surface. Cell density of CE surface 110 samples was higher as compared to AR, MP and EP samples. HAECs on CE surfaces 110 had spread on the grains and bridged across the grain boundaries 140 and a very homogenous covering of cells without any special orientation was also noted. In contrast, on AR, MP and EP samples, irregular endothelial cell growth with large uncovered areas and cracks in cell cytoskeleton was observed. No evidence of FBGCs was observed on the samples, but relatively more fields on AR, MP and some on EP samples showed signs of dead endothelial cells and debris.

GREDVY peptide was adsorbed on AR, MP, EP and CE 316L SS samples and stored in ambient conditions for 7 days and 31 days. HAECs were seeded on the samples for 24 hrs and results were compared with samples having cells seeded immediately after the adsorption of the peptide. Change in cell density, spreading area and number of focal adhesion contacts were estimated. As shown in FIG. 51, the EP and CE surface 110 (CE) specimens the HAEC density decreased significantly ($p<0.01$) on samples with cell seeded after with 31 days of GREDVY adsorption. The CE surface 110 samples include GREDVY: 2900 HAEC/$cm^2$; GREDVY (7 days): 2750 HAEC/$cm^2$; GREDVY (31 Days): 1900 HAEC/$cm^2$. HAEC density on CE surface 110 samples with cells seeded after 31 days of GREDVY shelf life was still significantly higher ($p<0.01$) as compared to other sample types. This indicates that even 31 days after adsorption, GREDVY peptides are stable on the CE surface 110 and can recruit endothelial cells in much higher number in contrast to EP, MP, and AR specimens. HAEC density of the CE surface 110 sample with cell seeded after 7 days of GREDVY adsorption showed no significant difference as compared to CE samples with cells seeded immediately after GREDVY adsorption.

HAEC spreading area decreased significantly ($p<0.01$) on EP and CE surface 110 (CE) specimens with cell seeded after 31 days of GREDVY adsorption (FIG. 52) compared to specimens seeded with cells immediately, or 7 days of GREDVY adsorption. The CE surface 110 samples include GREDVY: 8900 HAEC spreading area ($\mu m^2$); GREDVY (7 days): 8870 HAEC spreading area ($\mu m^2$); and GREDVY (31 Days): 6885 HAEC spreading area ($\mu m^2$). Endothelial cell spreading on CE surface 110 specimens with cells seeded after 7 days and even 31 days of GREDVY adsorption was still significantly higher ($p<0.001$) as compared to other samples studied.

As shown in FIG. 53, the CE surface 110 (CE) samples include GREDVY: 7.5 Focal adhesion points/$\mu m^2$ of endothelial cells; GREDVY (7 days): 7.3 Focal adhesion points/$\mu m^2$ of endothelial cells; and GREDVY (31 Days): 5.2 Focal adhesion points/$\mu m^2$ of endothelial cells. On CE surface 110 (CE) specimens no significant decrease in number of focal adhesion contacts was noted on samples with cell seeded after day 7, but significant decrease ($p<0.05$) was observed on specimens with cell seeded after 31 days of GREDVY shelf life. Significantly higher ($p<0.001$) number of activated focal adhesion contacts were observed on CE specimens as compared to other samples.

Another embodiment involves modifying the material surface to interact selectively with a specific cell type through biomolecular recognition events. The cell surface has a variety of receptors that bind with other cells or specific proteins, which compose the environment (known as the extracellular matrix "ECM") surrounding the cells. Biomimetic modification of the material in which peptides (a sequence of two or more amino acids joined by a chemical bond between the carbonyl group of the first amino acid and the amino group of the second amino acid) containing the adhesion domains of the ECM proteins are attached to the base material.

The biomimetic surface modification includes peptides that mimic part of the ECM affect cell attachment to the material, and those surfaces or three-dimensional matrices modified with these active peptides can induce tissue formation conforming to the cell type seeded on the material. One embodiment involves the incorporation of adhesion promoting oligopeptides into biomaterial surfaces. Since identification of the RGD peptide sequence as mediating the attachment of cells to several plasma and ECM proteins, including fibronectin, vitronectin, type I collagen, osteopontin and bone sialoprotein (BSP), it has been found that depositing RGD-containing peptides on biomaterials may promote cell attachment. Its ability to bind a variety of cells through ligand-receptor interactions makes RGD an exceptionally useful sequence for incorporating onto biomaterial surfaces.

RGD peptides that have not been designed to bind certain integrins (adhesion receptors on the cell surface with two subunits, designated α (alpha) and β (beta)) mimic a number of adhesion proteins and bind more than one receptor. In one embodiment, biomimetic surface modification increases integrin specificity by the chemical synthesis of cyclic peptides to provide conformational constrain and selected sequences flanking the RGD to give increasing affinity and selectivity. The affinity of these peptides is relatively low compared to the ECM proteins. The GRGDSP (gly-arg-gly-asp-ser-pro) which is derived from the cell attachment site of fibronectin is 1000 times less effective in cell attachment assays than fibronectin itself. An advantage of employing short bioactive peptides rather than the complete parent glycoprotein is selectivity for targeted cell types. GRGDSP, for example, is quite specific in its activity for the fibronectin receptor and changes as small as the replacement of the aspartic acid (D) with a glutamic acid (E) reduces the activity 100-fold or more.

The biomimetic surface modification can display specificity and binding affinity. The biomimetic surface modification may include the parameter of the surface conformation of the amino acids. Human melanoma (cancer) cells spread on looped RGD biomimetic surfaces in a concentration dependent manner, spread indiscriminately on carboxyl-coupled RGD, and did not spread on amino-coupled RGD surfaces. The surface density of RGD peptides may elicit different cellular responses. A surface density of $10^{-15}$ mol/cm$^2$ for GRGDY (gly-arg-gly-asp-tyr) covalently grafted to the surface of otherwise poorly adhesive glass substrate is sufficient to promote fibroblast cell (common cell type found in connective tissue) spreading, but focal contact formation (small region on the surface of the fibroblast that is anchored to the substrate and is mediated by clusters of integrin receptors) may be observed only at concentrations of $10 \times 10^{15}$ mol/cm$^2$ and higher. These measurements provide threshold for the design of practical peptide biomimetic biomaterials, as they indicate a minimum RGD density of $10 \times 10^{-15}$ mol/cm$^2$, corresponding to a spacing of about 140 nm between peptide ligands. The clustering of GREDVY at grain boundaries 140 includes promoting EC adherence and spreading. Another parameter that can influence cell adhesion is peptide clustering at the nanoscale level. Clustering of YGRGD (tyr-gly-arg-gly-asp) ligand significantly reduced the average ligand density required to support fibroblast cell migration whereas non-clustered ligands supported cell attachment but did not promote full spreading. Even though the most common cell-binding domain which has been used extensively as a candidate peptide to enhance cell adhesion onto biomaterial surfaces is the RGD sequence, other non-RGD-containing cell-binding domains exist, such as YIGSR (tyr-lle-gly-ser-arg) and IKVAV (lle-lys-val-ala-val) in laminin, REDV (arg-glu-asp-val) and LDV (leu-asp-val) in fibronectin, DGEA (asp-gly-glu-ala) in collagen I, and various heparin-binding domains. Certain studies have demonstrated that a more "complete" cell response (e.g. cell attachment, spreading, focal contact formation and organized cytoskeletal assembly) was obtained by providing the cell with both the cell-binding (RGD containing) and heparin-binding domains of fibronectin or BSP.

The luminal surface of the blood vessel consists of a continuous monolayer of endothelial cells and is normally maintained in a nonthrombogenic and anticoagulatory status by the surface expression and/or secretion of several regulatory factors by the vascular endothelium. The abluminal surfaces of vascular endothelial cells are in intimate contact with and anchored to the basement membrane extracellular matrix (ECM). Basement membrane ECM contains protein components such as type IV collagen, laminin, entactin, heparin sulfate proteoglycan, vitronectin (VN), and fibronectin (FN), providing a substrate for the attachment of endothelial cells to the vascular wall. Cultured endothelial cells have been shown to attach and spread on many ECM proteins, including FN, laminin, VN, fibrinogen, collagen, and von Willebrand factor. Cell adhesion and spreading to these adhesive ECM proteins proceeds primarily via the interaction of the integrin class of cell adhesion receptors with the RGD ligand sequence located within cell-binding domains of many cell adhesion ECM proteins. Substrates containing covalently immobilized REDV (arg-glu-asp-val) containing peptides selectively supported the attachment and spreading of human umbilical vein endothelial cells (HUVECs) over that of fibroblasts, vascular smooth muscle cells, and blood platelets. REDV peptide was immobilized to silane-modified glass via the N-terminal primary amine, using an N-terminal glycyl residue as a spacer and a C-terminal tyrosyl residue as a site for radioiodination.

Atomic force microscope (AFM) and time of flight secondary ion mass spectroscopy (ToF SIMS) where used to characterized the surfaces of as-received (AR), mechanically polished (MP), electrochemically polished (EP) and CE surface 110 (CE) 316L SS samples with no peptide, non-specific peptide (GRADSP) and specific peptide (GREDVY). Adsorption of cationic and anionic dye on samples complimented these analyses by identifying surface charge distribution, previously mentioned. AR samples had a small net negative charge on the surface and low concentration of positive ions; whereas, in contrast, on the other end of the spectrum chemically etched specimens showed a very high concentration of positive ions on the grain boundaries. The overall concentration of positive ions on the CE surfaces 110 was much higher as compared to other specimens. AFM force volume data also confirms that CE surfaces 110 samples had a net positive charge (higher force of adhesion), which was much higher as compared to AR, MP and EP specimens.

Inherent electrostatic properties of AR, MP, EP and CE 316L SS specimens were utilized to graft GREDVY peptide on the surface and observe its effects on HAECs. Higher adsorption of anionic dye and lower adsorption of cationic dye was included on CE surfaces 110 (CE) samples as compared to AR, MP, and EP specimens, supporting the AFM and ToF SIMS results. Since most of the peptides and plasma proteins as mentioned previously are highly electronegatively charged, high positive charge on CE surfaces 110 specimens, specifically on the grain boundaries 140, is responsible for higher adhesion of GREDVY peptides onto CE surface 110 specimens and subsequent higher attachment and spreading of HAECs as compared to other samples studied. The increased adsorption of GREDVY peptides at the grain boundaries 140 of CE surfaces 110 is responsible for the increased endothelial cell adhesion and spreading observed on CE surfaces 110 relative to the other three 316L SS surfaces evaluated.

EXAMPLE VI

Human Endothelial Cell Culture on the CE Surface

High mass resolution spectra were acquired with ToF SIMS on CE surfaces 110. At least ten spectra were recorded on each sample. Positive and negative ion spectra and images were separately acquired and analyzed. The Ni/Cr ratio in the tissues adjacent to metal implants is greater in infected cases than in non-infected. Therefore, Ni/Cr ratio could have value as a predictor of biocompatibility. Ni/Cr ion intensity ratios based on ToF SIMS data were calculated for differently finished 316L SS CE surfaces 110, as shown in FIG. 54. CE surface 110 samples (CE-grain and CE grain boundary 140) revealed very low Ni/Cr ratio as compared AR, MP and EP specimens, where the CE-Grain included a Ni/Cr ratio between about 0.04 to 0.05 and the CE-Grain boundary included a Ni/Cr ratio between about 0.025 to 0.03. The order of decreasing Ni/Cr ratios or increasing biocompatibility of the surface is: AR>MP>EP>CE.

FIG. 55 represents endothelial cell density on AR, MP, EP and CE surface 110 (CE) samples after 8 hrs, 3 days and 7 days, showing CE-8 hr: 1990 cells/$\mu m^2$; CE-3 days: 1650 cells/$\mu m^2$; and CE-7 days: 1410 cells/$\mu m^2$. Statistically significant differences ($p<0.05$) in number of cells attached per $cm^2$ on AR samples were observed after 7 days compared to 8 hrs and 3 days, and a decrease in number of endothelial cells between 8 hrs to 7 days was noted. For CE samples, statistically significant difference in cell density was observed within 8 hrs/3days ($p<0.05$), 8 hrs/7 days ($p<0.001$), and 3 days/7days ($p<0.001$) sample groups. Overall, the endothelial cell density on CE samples was higher after all time periods as compared to AR, MP and EP samples.

Endothelial cell spreading area on AR, MP, EP and CE surface 110 (CE) 316L SS specimens are shown in FIG. 56 where CE-8 hr: 4350 cell spreading area ($\mu m^2$); CE-3 days: 7250 cell spreading area ($\mu m^2$); and CE-7 days: 19990 cell spreading area ($\mu m^2$). Statistically significant difference in cell spreading area was observed within MP ($p<0.01$), EP ($p<0.01$) and CE ($p<0.001$) sample groups. After 7 days the endothelial cell spreading area on CE surface 110 samples was 2.3 times higher than that on EP and 4 times higher than that on MP samples.

Figure 57:
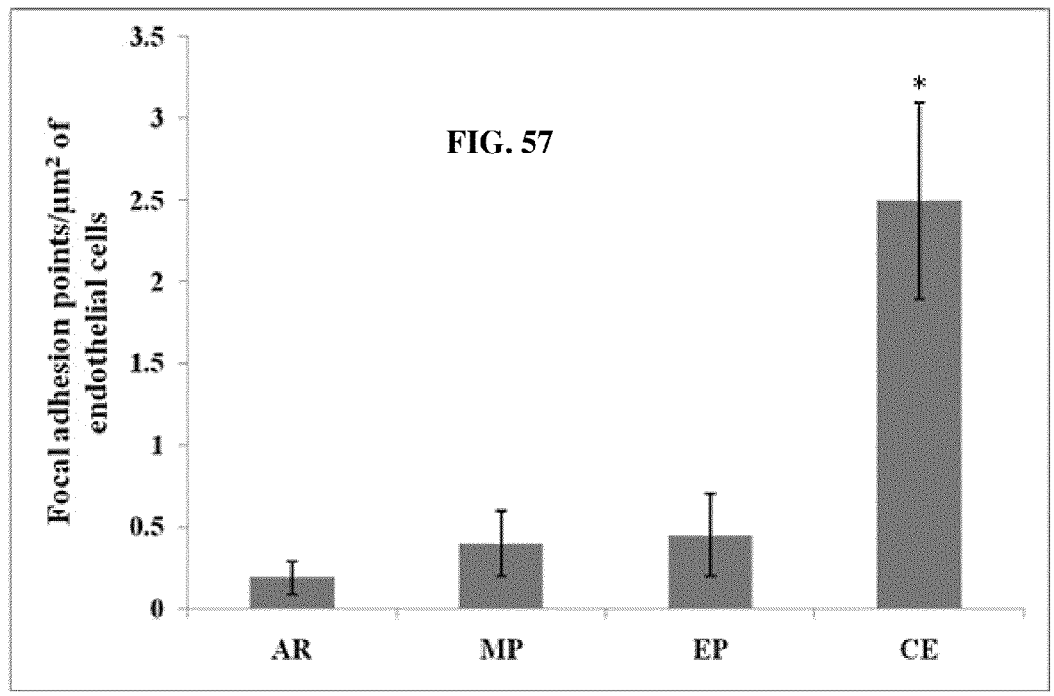
FIG. 57 is a bar graph showing the number of focal adhesion points per μm of endothelial cell on differently finished 316L stainless steel substrates (n=40,*p<0.001).

FIG. 57 shows the number of focal adhesion contacts formed by ECs on AR, MP, EP and CE samples, where the CE samples included 2.47 focal adhesion points/$\mu m$ of endothelial cells. Significantly higher ($p<0.001$) number of activated focal adhesion points were observed for CE samples as compared to AR, MP and EP specimens after 7 days culture period.

EXAMPLE VIII

Drug Loading and Eluting on the CE Surface

Drug-eluting stents (DES) have dramatically reduced restenosis rates following percutaneous coronary interventions (PCI) and now represent the treatment of choice in many cases. The release system 200 comprises a polymer-free approach involving a novel microstructuring technique, which includes selective three dimensional structuring with the chemical etching method described previously. The release system 200 is based on chemical etching, including an intrinsic material property and geometric feature of the CE surface 110, which is used in loading and release of a drug. EP and CE surfaces 110 may be prepared by the method described previously, and incubated in a drug solution for 48 hrs and subsequently cleaned in double distilled water and dried at 40° C. The extent of drug loading and pattern of elution from EP and CE surfaces 110 may be analyzed using fluorescence microscopy, HPLC and XPS.

Fluorescence microscopy indicated dexamethasone accumulation along the CE grain boundaries 140 with little or no drug detected on EP surfaces. Drug release kinetics indicated a sustained gradual release of the drug from CE surfaces 110 over a period of three weeks. This gradual release can be attributed to positively charged CE surface 110, predominantly high concentration of positive ions at the grain boundaries 140 and micro architecture of the grain boundaries, which stores drugs within the CE surface 110 and considerably decelerates the drug release. No evidence of drug release was observed from EP substrates. Material surfaces can be modified by chemical etching to create CE surfaces 110 where the grain structure acts as a reservoir for the attachment and slow release of negatively charged drugs agents.

The sample preparation of CE surfaces 110 (CE) specimen was prepared as described previously. Also electrochemically polished (EP) specimens were used as reference; the surface treatment of these specimens, as described previously. Roughness measurement AFM was used, as previously indicated.

Dexamethasone was selected as a model anti-inflammatory agent, because it is a steroid that prevents restenosis in animal models and has a therapeutic performance comparable to sirolimus and paclitaxel; furthermore, dexamethasone-eluting stents have shown low restenosis rates in early human trials. Dexamethasone has a molecular weight of 392.464 amu and a chemical formula $C_{22}H_{29}FO_5$. It is a rough prolate ellipsoid, with a van der Waals molecular surface area of 34.633 $nm^2$ and a volume of 38.951 $nm^3$. It is bounded by an ellipsoid with axes lengths of 1.2945 nm, 0.6708 nm and 0.3785 nm, respectively.

The drug solution preparation involved the dissolution of 1 mg of dexamethasone in 1 ml of ethanol at room temperature and atmospheric pressure. The electrochemically polished and chemically etched surfaces were immersed in 1 ml of drug solution for 48 h which was considered sufficient for attaching or loading the drug on the 316L SS surfaces. Upon completion of the drug-loading step, and in order to preclude the presence of undesirable clusters of drug on the surface, the samples were immersed in double distilled water (which is not a solvent for dexamethasone), while manually agitating the samples during a 2 min period; this step was repeated three times. Subsequently, the solvent remaining on the samples was removed by a mild evaporation at 40° C. for an hour.

Primary dexamethasone antibody solution was injected (200 μl per sample) on the samples. After 60 min incubation time at 37° C. the samples were rinsed with PBS and the secondary antibody (fluorochrome, 200 μl per sample) solution was introduced in the ratio of 1:200 for 60 min at 37° C. followed by rinsing with PBS. Fluorescent images of the drug-adsorbed samples, labeled with the appropriate fluorescent antibody, were obtained under similar conditions (acquisition time, brightness, contrast) using a fluorescence microscope. Particular attention was paid to keeping samples wet during the measurements since drying of the samples was found to deteriorate the image quality and reproducibility of the results. As a control for non specific adsorption of dexamethasone primary antibody and secondary fluorochrome, samples without drugs were exposed to primary and secondary antibody.

Figure 58:
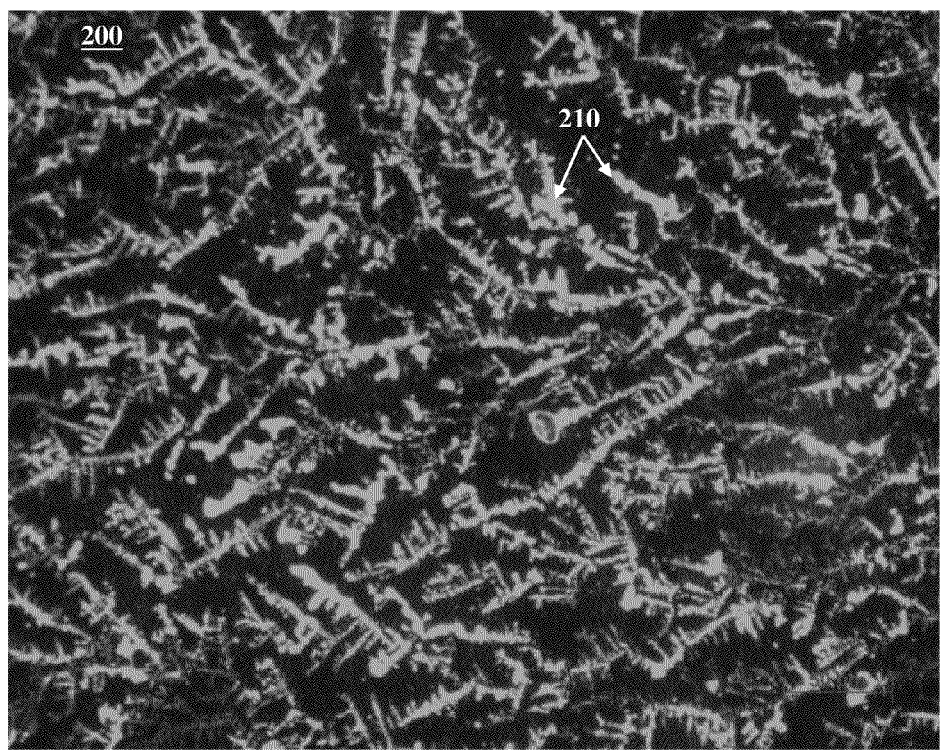
FIG. 58 is a representative fluorescence micrograph showing dexamethasone drug adsorbed on CE surface 110 (CE) 316L stainless steel substrates, where the bright areas indicate higher concentration of the drug showing the relatively high drug concentration on the grain boundaries on chemically etched sample.

FIG. 58 illustrates fluorescence micrographs of dexamethasone drug 210 adsorbed on electrochemically polished (EP) and CE surfaces 110 (CE) 316L SS substrates as detected by specific anti-dexamethasone antibodies. As a control, samples were also exposed to anti dexamethasone primary antibody and secondary antibody (fluorochrome). The observed fluorescence intensities were very small compared to signal from specific antibody against the adsorbed drug, implying that non-specific binding makes typically less than 5% contribution in comparison to the specific signals observed in case of the drug. On CE surfaces 110 (CE) samples, dexamethasone drug adsorption was higher, specifically on the grain boundaries 140; whereas, no such adsorption pattern was noted on EP substrates. The specificity of drug adsorption on the grain boundaries for chemically etched samples can be related to the higher adhesion force and more concentration of positive ions. Quantification of the fluorescence intensity of adsorbed drug on the samples was also done. Statistical analysis suggests that the drug attachment on CE samples was significantly higher (p<0.0001) as compared to EP samples. Average roughness (Ra)

Figure 59:
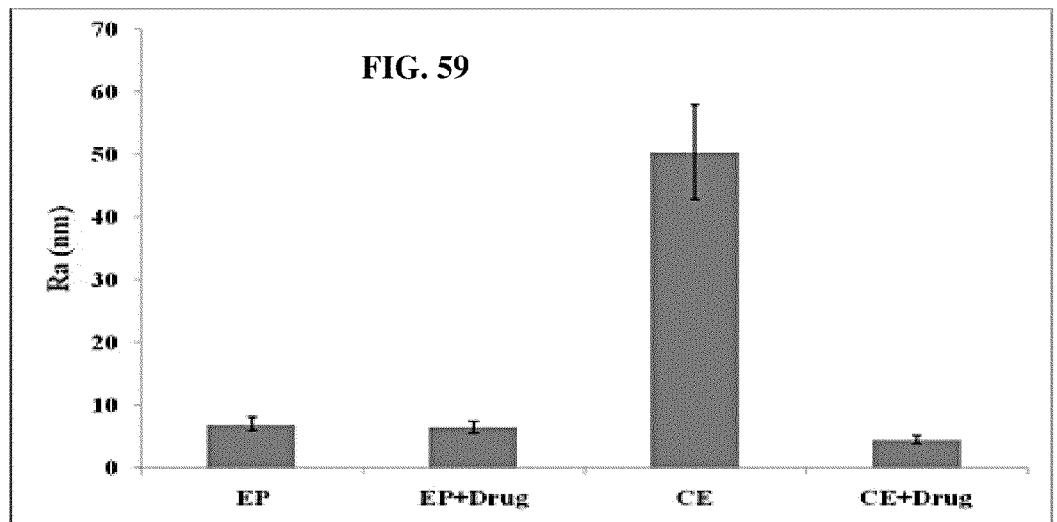
FIG. 59 is a bar graph of the average roughness values (Ra) measured on EP, EP with drug, CE surface 110 (CE) and CE with drug using atomic force microscope (n=25,*p<0.0001).

A comparison of average roughness values for EP, EP with adsorbed drug, CE surface 110 and CE surface 110 with drug adsorbed on the surface is shown in FIG. 59. For CE surface 110 samples, the roughness value decreased drastically after drug adsorption indicating that the grain boundary 140 had been filled with the drug agent 210. The roughness values measured on samples were: 7.0±1.05 nm (EP), 6.5±0.975 nm (EP+drug), 50.5±7.56 nm (CE), 4.48±0.67 nm (CE+drug). A decrease in roughness value by 11 times is noted for CE surface 110 samples with adsorbed drug, whereas, no significant change in roughness values was observed on EP specimens due to drug adsorption. This confirms the fluorescence microscopy findings which also indicated that the dexamethasone drug adsorption on EP samples was negligible.

AFM phase images can be performed at the same time as topographic imaging with tapping mode in single scan. The phase imaging mode takes advantage of the fact that the tip-sample interactions do not only depend on the sample's topography but also on different sample characteristics for example sample hardness and elasticity or adhesion. Variation in material properties lead to a phase lag of the cantilever oscillation, relative to the signal sent to the cantilever's piezooscillation driver. This phase lag is simultaneously monitored by the AFM control electronics, recorded and transformed into AFM images. Phase imaging also acts as a real time contrast enhancement technique because phase imaging highlights edges. Fine features, such as surface steps or edges, which can be obscured by a rough topography, are revealed more clearly through phase imaging. Therefore, to assess the change in CE surface 110 microstructural features of 316L SS samples before and after drug loading, phase images were recorded in addition to the topographic images. The scan rate ranged from 0.5 to 1 Hz and the tip velocity was maintained between 25 and 50 µm/sec in a scan area of 50 µm×50 µm. Phase images were acquired using non-functionalized silicon nitride probes.

Figure 60A:
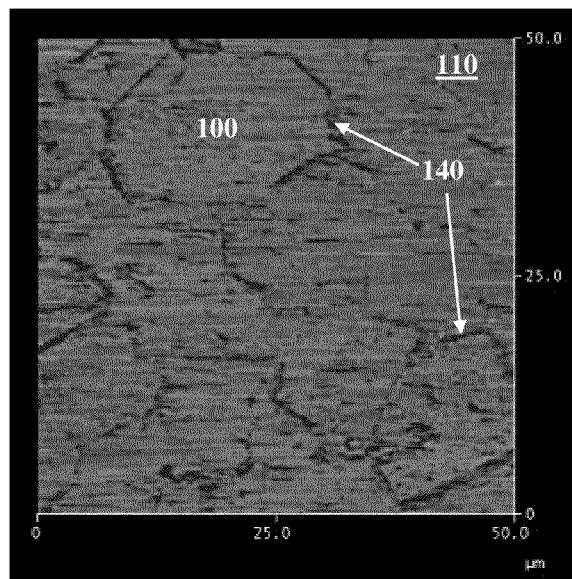
FIGS. 60A-B are atomic force microscopy phase images of (60A) the CE surface 110 (CE) sample and (60B) CE surface 110 sample with drug, where the grain boundaries are clearly visible on CE surface 110 specimen, whereas, on CE surface 110 sample with drug the contrast between grain and grain boundary has remarkably decreased.
Figure 60B:
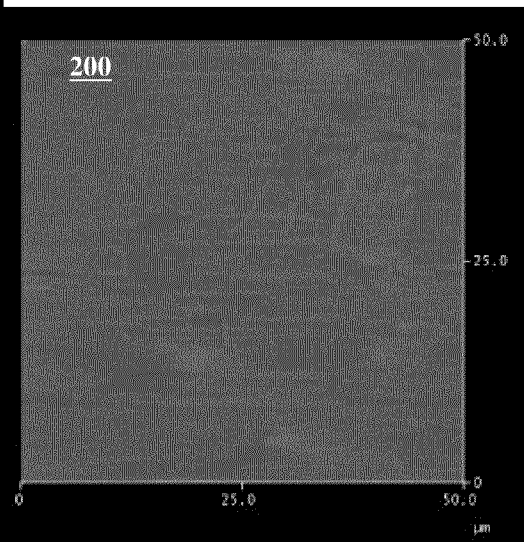

AFM phase images AFM phase images provide a better resolution of the finer microstructural details and also provide insight regarding interactions between the surface and the tips. As mentioned earlier, the phase image is generated by mapping the phase lag of the cantilever oscillation resulting from local tip surface interaction, relative to the phase of the drive oscillation. Since it is energy dissipation that directly impacts the phase signal, variations in adhesion, elasticity, viscoelasticity, and long-range forces between the sample and the tip, which all impact the energy dissipation, can be mapped in the phase image. Therefore, AFM phase images for EP, EP with drug, CE and CE samples with adsorbed drug were recorded. No difference in the AFM phase image before and after drug adsorption could be noted for EP specimens. For CE surface 110 samples, phase image of the samples before drug adsorption exhibited the presence of grain boundaries 140 and grains 100, as shown in FIG. 60A. This observation confirmed the findings of AFM and ToF SIMS spectra and image that indicated that there is a difference in concentration of positive and negative charge and subsequently the force of adhesion between grain 100 and grain boundaries 140 on CE surface 110 samples. After dexamethasone adsorption on the CE surface substrate 200, as shown in FIG. 60B, the contrast between grains and grain boundaries 140 decreased considerably and a relatively homogeneous surface was revealed, which indicates that the drug was adsorbed both on the grains and the grain boundaries. The grain boundaries 140 acted as micro depots that were filled with dexamethasone drug molecules. Since the surface microstructure is completely invisible on AFM phase image after drug adsorption, then at least one monolayer of the drug is adsorbed on the surface.

For release rates, the drug-loaded samples were immersed in 2 ml of PBS and placed on an orbital shaker operating at 190 rpm to remove the incorporated drug prior to high-performance liquid chromatography (HPLC) analysis. The elution media were continuously agitated to maintain a uniform dexamethasone distribution. Individual specimens were immersed in 2 ml elution medium for a total duration of 30 days. The elution medium was renewed at periodic intervals, in order to avoid a saturation of the medium with the drug. Thus, the drug release curves result from the accumulation of the measured values per sampling time. The Dexamethasone amounts in buffer solutions was determined by HPLC (Waters 2695 module) equipped with Waters 2487 dual wavelength UV detector, a Nova-Pak C18 column (3.9 mm×150 mm, 4 um) and Empower2 processing software. The injection volume was 20 µl for each testing sample. A mixture of 60% methanol: 40% water at a flow rate of 1 ml/min was used as eluent and UV detection at 254 nm. Drug eluted solution was analyzed in HPLC for the amount (ng) of drug eluted after 1, 5, 7, 9, 11, 13, 15, 17, 19, 21, 23, 25, 27 and 29 days of elution time. Fifty different samples were taken at each time point. Calibration curves were obtained by plotting peak area ratios versus concentration of dexamethasone. Dexamethasone showed linearity in the range of 0.1-6.75 ng/µL. Cumulative drug elution profile was also plotted.

Figure 61:
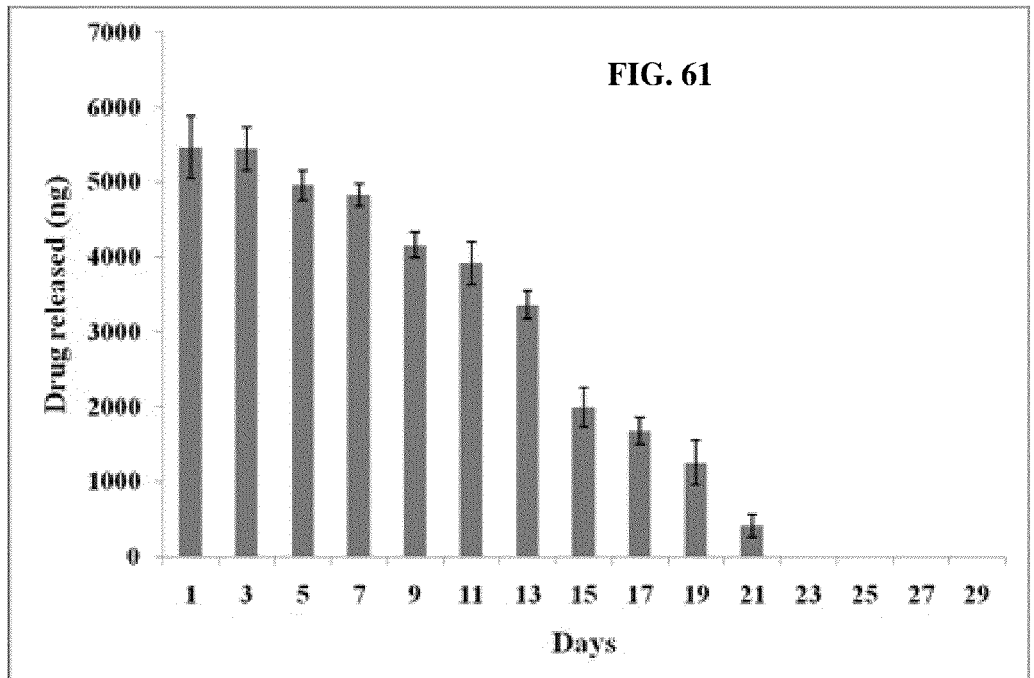
FIG. 61 is a bar graph representing the amount (ng) of dexamethasone drug released from chemically etched 316L SS CE surface 110 over a period of 29 days (n=50).
Figure 62:
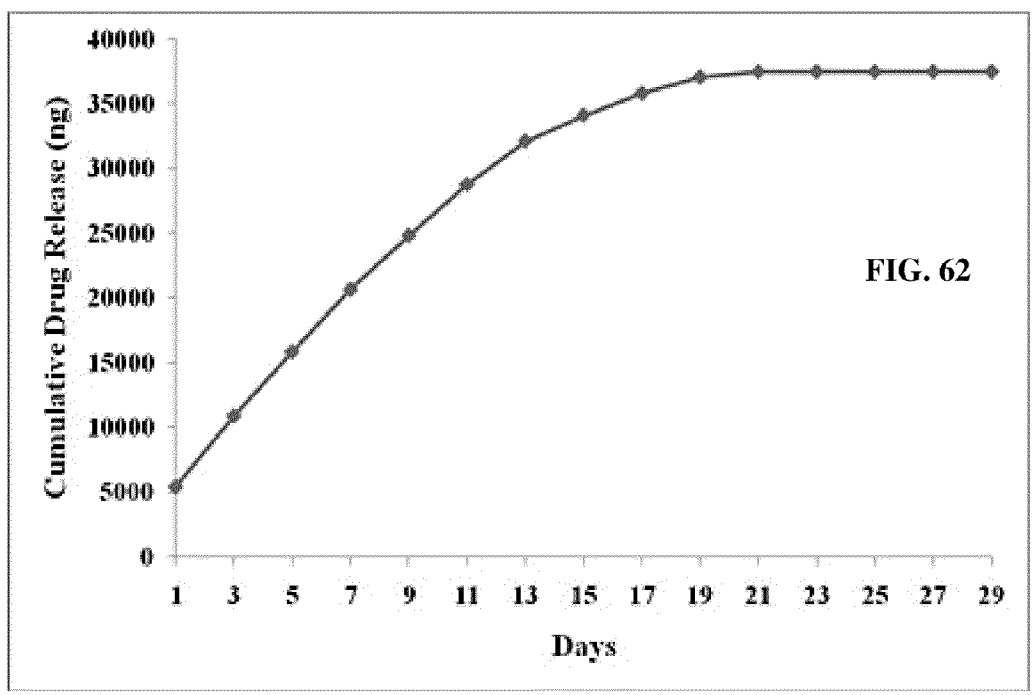
FIG. 62 is a bar graph representing cumulative dexamethasone drug release profile from chemically etched 316L SS CE surface 110 over 29 days.

FIG. 61 shows the amount of dexamethasone released from CE surface 110 etched 316L SS surfaces after 1, 3, 5, 7, 9, 11, 13, 15, 17, 19, 21, 23, 25, 27 and 29 days, which include a drug release of 5450, 5450, 4990, 4800, 4225, 3970, 3350, 1990, 1625, 1100, 475, 0, 0, 0, and 0 ng, respectively for each day. At each time point, the release media was analyzed for the level of dexamethasone. No drug release was observed after 23 days. For 1-3 days, the drug release rate is approximately 2750 ng/day for the initial drug release, and a slow release is for 11-13 days, which is approximately 2000 ng/day. FIG. 62 shows the cumulative drug release profile for CE surface 110 specimens, where no burst release of drug from the surface was noticed. Initially dexamethasone drug released from CE surface 110 is the loosely bound drug attached on the grain 100 and grain boundaries 140, and in later stages the release kinetics was slowed due the slow release of drug from the grain boundaries 140. Therefore, two phases of drug release were observed on chemically etched surfaces: a nearly linear release of the drug from the substrate within the first 7 days, followed by a gradual slowing release of the drug up to 21 days. The slow drug release is related with the time required for the drug to detach from the grains 100 and in case of drug molecules adsorbed on the grain boundaries 140; the drug molecules detach and pass through the grain boundaries 140 that act as microdepots, into the bulk solution. As derived from the cumulative drug release profile, 90% of the drug was eluted during first two weeks and the remaining 10% during the third week.

This cumulative release profile presented in FIG. 62 from CE surface 110 etched 316L SS sample is significant. Generally, drug release from polymer based matrices and polymer coated substrates begins with an initial bursting. But in the CE surfaces 110, the bond between electronegative dexamethasone drug molecule and positively charged CE surfaces 110, combined with micro architecture of the surface prevents drug loss by initial bursting, thus allowing for sustained release of the drug, prolonging the period of treatment. As a result, toxic side-effects caused by the high dose initial drug release are effectively decreased.

To have a qualitative estimate of drug present on the specimens and mechanism of drug release from the samples after 1, 5, 10, 15, 20, and 25 days of elution time, dexamethasone antibody solution was pipetted on the samples. After 60 min incubation time at 37° C. the samples were rinsed with PBS and incubated in secondary antibody (fluorochrome) solution for 60 min at 37° C. followed by rinsing with PBS. Fluorescent images of the drug-adsorbed samples, labeled with the appropriate fluorescent antibody, was obtained under similar conditions (acquisition time, brightness, contrast) using a fluorescence microscope. X-ray photoelectron spectroscopy (XPS)

Figure 63A:
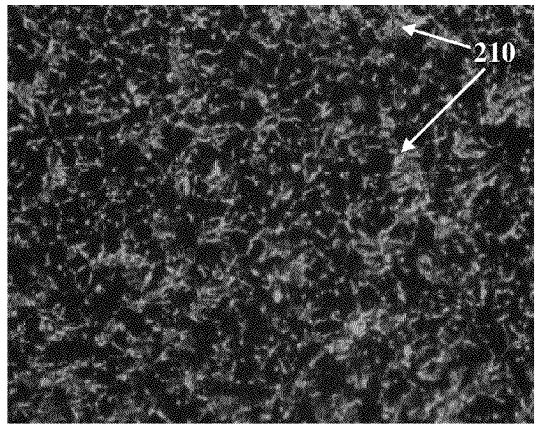
FIGS. 63A-F represents fluorescence micrographs showing dexamethasone drug on CE surface 110 (CE) 316L stainless steel substrates after (63A) day 1 (63B) day 5 (63C) day 10 and (63D) day 15 (63E) day 20 and (63F) day 25 of drug release in phosphate buffer saline solution (PBS), where the bright areas indicate more concentration of the drug (bar-50 μm).
Figure 63B:
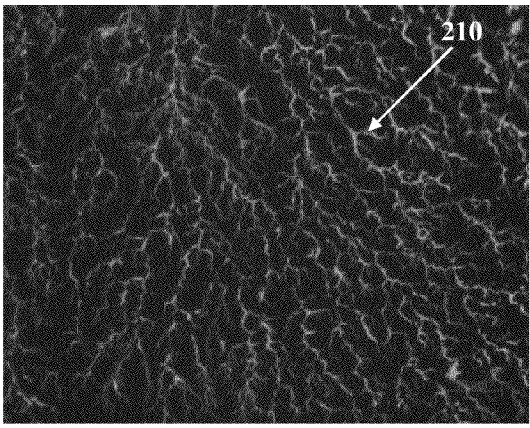
Figure 63C:
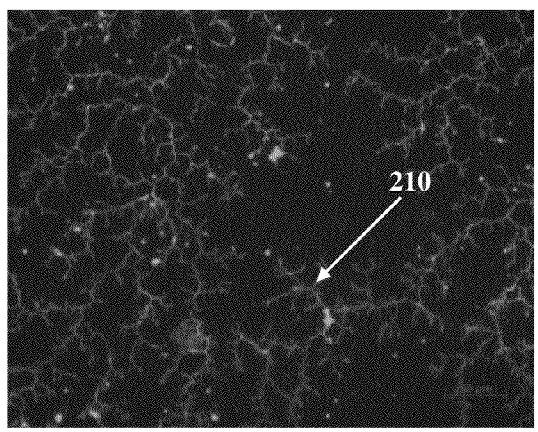
Figure 63D:
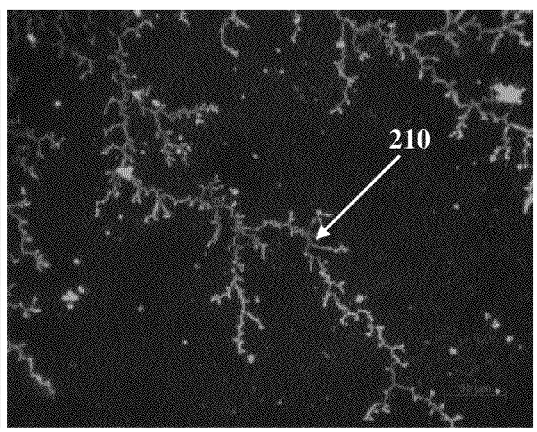
Figure 63E:
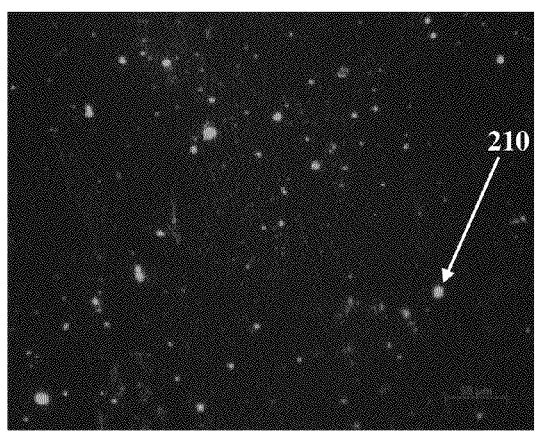
Figure 63F:
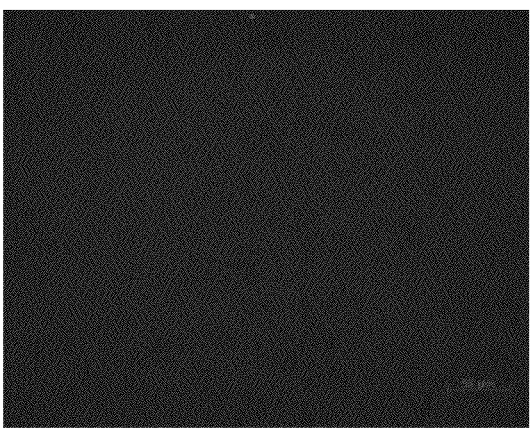

As shown in FIG. 58, which represents the fluorescence micrograph of CE surface 110 samples after drug loading 200, clusters of loosely bound drug 210 are clearly visible apart from the adsorbed drug on the grains 100 and grain boundaries 140. FIGS. 63A-D represents fluorescence micrographs of samples after different drug elution times. Loosely bound clusters of the drug are eluted after day 1 but the micrograph shows that drug is still adsorbed on the grains 100 and more on grain boundaries 140 (FIG. 63A). After 5 days of drug elution, no drug 210 was observed on the grains, whereas, bright fluorescence from the grain boundaries 140 indicated the presence of the drug (FIG. 63B). After day 10 (FIG. 63C), the drug 210 has started to elute from the grain boundaries 140, and after 15 days (FIG. 63D) of elution small amount of drug 210 is left on the grain boundaries 140. FIG. 63E shows the fluorescence micrograph of CE surface 110 specimen after 20 days of drug elution, which indicates that most of the drug 210 is eluted from the CE surface 110. After day 25 no fluorescence is observed on the CE surface 110 sample which indicates complete elution of dexamethasone from CE surface 110 samples. Since the grains have less adhesion force as observed by AFM and confirmed by less concentration of positive ions from ToF SIMS, dexamethasone is first eluted by desorbing from the grains 100 as noted between day 1 and day 5 of drug release. The high adhesion force and architecture of grain boundaries 140 causes the drug molecules 210 to remain bound for a longer period of time thereby slowing down the release kinetics of the drug.

Figure 64:
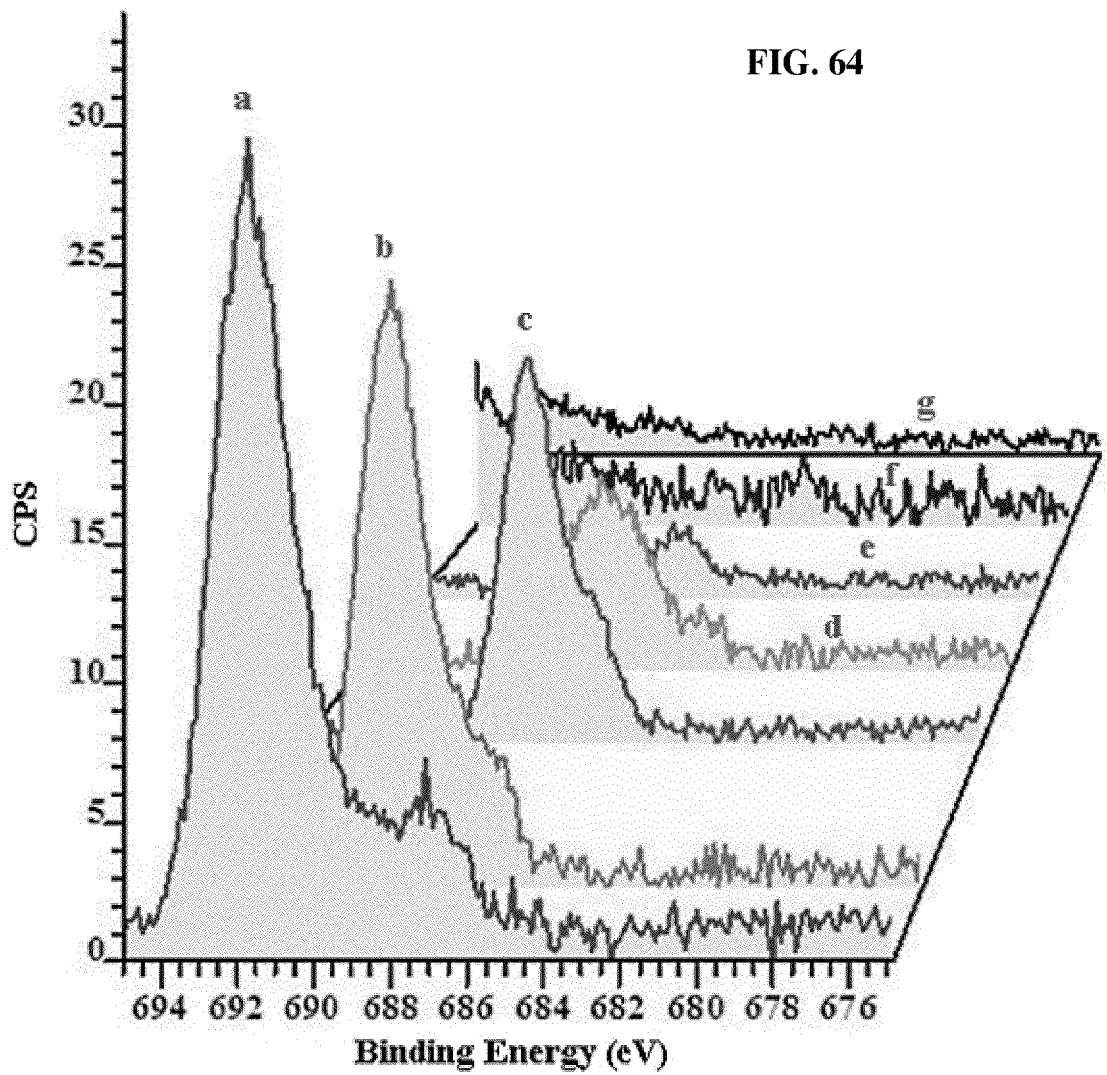
FIG. 64 is an XPS intensity plot showing the presence of fluorine peak on drug loaded CE surface 110 (CE) 316L stainless steel substrates after (a) 0 day; (b) 1 day; (c) 5 days; (d) 10 days; (e) 15 days; (f) 20 days; and (g) 25 days of drug release in PBS, showing a gradual decrease in intensity of fluorine peak from day 0 to 25, indicating a slow release of drug from the sample.

XPS was used to identify the fluorine peak so as to confirm the presence of dexamethasone drug on 316L SS CE surface 110 samples after drug loading and after 1, 5, 10, 15, 20 and 25 days of drug release from the specimens, as previously indicated. To further probe the presence of drug before and after release, the decrease in intensity of fluorine peak (from the drug) was observed. Strong fluorine peak after drug adsorption can be seen in FIG. 64 curve a. A gradual decrease in intensity of the fluorine peak is noted after day 1 of release till day 20 (Curves b, c, e and f); whereas, no fluorine peak was detected on CE surface 110 samples after 25 days of dexamethasone elution (FIG. 64 curve g). Electrochemically polished samples showed no fluorine peak. Hence, the XPS data corroborates the results obtained from high performance liquid chromatography (HPLC) and fluorescence microscopy.

The procedure of stenting with drug eluting stents can be separated into three stages, with each one having different requirements on the surface properties. The first stage addresses the implantation of the stent. During the implantation process, the drug coating is subjected to friction forces due to contact with the arteries, mechanical stresses due to stent deformation at turnings and shear stresses induced by the blood flow. The basic requirement in order to assure a protection of the drug during the first phase is sufficient adhesion of the drug, which can be accomplished by a high surface adhesion and micro roughness and by a mechanical interlocking of the drug layer and the surface.

Once the stent is placed within the stenosed artery, the process of drug release or delivery begins. In this second stage a controlled, gradual release is required in order to assure a maximum efficiency of the drug and in order to avoid harmful effect of initial drug overdose. The porcine coronary injury model using immunocytochemical methods showed that after injury to the artery, smooth muscle cells (SMCs) begin to proliferate ~24 hrs later and migrate from adventitia through media to neointima; within 2 weeks the cellular proliferation is largely completed. Based on this mechanism, the 2 weeks until proliferation is completed is very important to prevent restenosis. For this reason, the release system 200 includes the release of dexamethasone for more than two weeks, which would be beneficial in preventing restenosis. The release system 200 randomly distributed microdepots on the CE surface 110 in the form of etched grain boundaries 140 on 316L SS surface, which stores part of the drug loaded, in order to achieve a controlled release without an additional barrier layer. The grain structure 100 was controlled in a way to yield a depth and width ratio in the range of 0.5 to 1. The depth of the grain boundaries 140 is limited due to mechanical aspects, since the grain boundaries 140 act as notches and thus might weaken the integrity of the material. When assuming depots with a rounded base, a depot of 10 µm depth and 5 µm width, includes a notch radius of 2.5 µm and a ratio of depth to notch radius of 4. The diminished effective load bearing area in this case can be compensated for by an adaptation of the stent design.

The third stage of the stenting procedure is the bare stent phase. After release of the drug, which previously formed a barrier between stent and tissue, the stent is in direct contact with the tissue. In order to assure a long term fixation of the stent within the tissue and to prevent chronic inflammation processes, an optimal surface has to be biocompatible after release of the drug and should provide a suitable basis for cell ingrowth. The latter can be achieved by the geometric features, which support the ingrowth of cells. The geometric features in the range of the size of cells (about 10-20 µm) can promote coordinated cell growth. Human aortic endothelial cell (HAEC) adhesion and migration on chemically etched 316L SS surfaces suggests that higher HAEC migration distance, rate and percentage coverage on chemically etched surfaces relative to EP samples.

The CE surface 110 specimens include very high concentration of positive ions on the grain boundaries 140. AFM force volume data also confirmed that CE surface 110 samples had a net positive charge which was significantly higher as compared to EP specimens. The release system 200 for electrostatic deposition of drug onto a stent may include ionizing a drug within a chamber so that the drug is attracted to and deposited on the charged stent. The CE surfaces 110 provided a surface with sufficient adhesion of the drug. The CE surfaces 110 included microdepots in the form of grain boundaries 140 on the surfaces, which have the capacity of storing a certain amount of drug and decelerate release of the drug. The CE surface 110 approach uses the intrinsic material structures in order to create randomly distributed geometric features. The geometric features are worked out of the material structures by chemically etching using 1 ml HCl+1 ml HNO₃+1 ml Glycerol. Hydrochloric acid selectively removes the crystal planes within the grain 100 by etching, which produces an increased roughness without creating grain boundaries 140 and the selective material removal at grain boundaries 140 is caused by nitric acid etching. Glycerol controls the strength of the etchant without which the microstructures were found to be not suitable for the use on stents as the surfaces were very rough and evidence of pit formation was observed. Therefore, the combination of HCl, HNO₃ and Glycerol exposed the positively charged 316L SS material microstructure, particularly created a grid of highly positively charged grain boundaries 140 suitable for electrostatic attachment and storage of dexamethasone drug molecules.

EXAMPLE IX

Prophetic Examples

The surface etching can also lead to a change in mechanical properties through various effects. Etching of the surface means a material removal, which causes the load bearing cross sectional area to diminish for implantable devices. This effect can be compensated by a proper adaption of the stent design, namely an allowance for the expected material removal. One problem is the high cycle fatigue behavior of the modified surface. The grain boundaries 140 generated through the etching process may work as notches and may represent initial points for crack propagation during the cyclic strain of the heart beat. Therefore, mechanical property evaluation should be carried out in future, which might include testing radial strength, flexibility and fatigue behavior of the etched surfaces.

The etching process changes the surface morphology and eventually the surface chemistry and both these factors may influence the corrosion behavior of the substrate. Therefore, in-vitro corrosion experiments may be performed in simulated body solution (e.g. Ringer's physiological solution). In order to study the electrochemical behavior of the etched substrates in a simulated physiological electrolyte, tafel, potentiodynamic and cyclic voltammetry measurements may be performed. With this method, the corrosion current density could be determined, breakdown potential and the passivity range of the etched substrates could be determined, and subsequently their susceptibility to pitting corrosion could be determined. Release of nickel, chromium and iron ions can be assessed after the experiments by analyzing the collected electrolyte with atomic adsorption spectrometry (AAS). Corrosion property evaluation will then lead to further optimization of the etching process.

In-vivo tests can be planned in order to validate the clinical applicability. If the in-vivo results are positive the microstructures could be further optimized in order to yield an optimum release and an optimum distribution of the drug. This optimization could be achieved by a modulation of the etching parameters in terms of the release kinetics. The distribution, on the other hand could be adjusted to a certain degree by slight variations in the heat treatment of the stents, i.e. by generating uniform grains of a certain size. In one aspect, the adaption of the inner (luminal) side of the stent in order to yield targeted promotion of endothelialization. The luminal side does not contain drugs, since in the initial stage it is in direct contact with the blood stream. However, after the initial stage this side is quickly covered with tissue as well, so that it is prone for a microstructuring specifically tailored for endothelialization. In one embodiment, a stent could receive two different CE surface 110 treatments, a first one that comprises a microstructuring of the inner side or abluminal sides, followed by a second step to create grain boundaries for drug release on the outer sides or luminal sides.

While the present invention has been described with reference to its preferred embodiments, those of ordinary skill in the art will understand and appreciate that variations in structural materials, bioactive agents, etching methods, device configuration or device indication and use may be made without departing from the invention, which is limited in scope only by the claims appended hereto.

We claim:

1. An implantable, biocompatible metal material, comprising at least one surface of the biocompatible metal material, wherein the at least one surface has an array of geometric features on the at least one surface thereof, wherein each of the geometric features has a chemically etched surface having a grain structure and a plurality of grain boundaries surrounding the grain structure, wherein the plurality of grain boundaries have a higher amount of positive charge as compared to the grain structure to promote the formation of an endothelial cell layer.

2. The implantable, biocompatible metal material according to claim 1, wherein the plurality of grain boundaries is the dividing structure between two adjacent grain structures that have different crystallographic orientations.

3. The implantable, biocompatible metal material according to claim 2, wherein the grain surface and the grain boundaries have an average roughness of about 10-160 μm.

4. The implantable, biocompatible metal material according to claim 2, wherein the grain structure has a positive charge concentration of about −0.2 to −0.3 nN and the grain boundaries have positive charge concentration between about −0.80 to −1.0 nN.

5. The implantable, biocompatible metal material according to claim 4, wherein the grain boundaries have a width and depth between about 1 μm to about 2 μm.

6. The implantable, biocompatible metal material according to claim 2, wherein each of the geometric features has a structural feature selected from at least one of: deep and narrow crevices, protrusions, and a smooth surface on the grains.

7. The implantable, biocompatible metal material according to claim 2, wherein the grain structure has a surface area of about 10-150 μm².

8. The implantable, biocompatible metal material according to claim 5, wherein at least one of the geometric features further comprises a drug coating along the grain boundaries and within the grain structure.

9. The implantable, biocompatible metal material according to claim 8, wherein the drug coating comprises negatively charged molecules.

10. The implantable, biocompatible metal material according to claim 2, wherein the biocompatible metal material is stainless steel.

11. The implantable, biocompatible metal material according to claim 2, wherein the biocompatible metal is nitinol.

\* \* \* \* \*